United States Patent
Scharenberg

(10) Patent No.: US 11,753,460 B2
(45) Date of Patent: Sep. 12, 2023

(54) METHODS OF EXOGENOUS DRUG ACTIVATION OF CHEMICAL-INDUCED SIGNALING COMPLEXES EXPRESSED IN ENGINEERED CELLS IN VITRO AND IN VIVO

(71) Applicant: Seattle Children's Hospital, Seattle, WA (US)

(72) Inventor: Andrew M. Scharenberg, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 671 days.

(21) Appl. No.: 16/467,013

(22) PCT Filed: Dec. 12, 2017

(86) PCT No.: PCT/US2017/065746
§ 371 (c)(1),
(2) Date: Jun. 5, 2019

(87) PCT Pub. No.: WO2018/111834
PCT Pub. Date: Jun. 21, 2018

(65) Prior Publication Data
US 2020/0123224 A1  Apr. 23, 2020

Related U.S. Application Data

(60) Provisional application No. 62/433,540, filed on Dec. 13, 2016.

(51) Int. Cl.
C12N 15/62 (2006.01)
C07K 14/715 (2006.01)

(52) U.S. Cl.
CPC .......... *C07K 14/7155* (2013.01); *C12N 15/62* (2013.01); *C07K 2317/53* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,173,414 A | 12/1992 | Lebkowski et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren et al. |
| 5,258,506 A | 11/1993 | Urdea et al. |
| 5,262,536 A | 11/1993 | Homes et al. |

(Continued)

FOREIGN PATENT DOCUMENTS

| | | |
|---|---|---|
| WO | WO 93/07883 | 4/1993 |
| WO | WO 94/018317 | 8/1994 |

(Continued)

OTHER PUBLICATIONS

Banaszynski et al., Apr. 2005, Characterization of the FKBP-rapamycin-FRB ternary complex, Journal of the American Chemical Society, 127(13):4715-4721.

Banaszynski et al., Sep. 8, 2006, A rapid, reversible, and tunable method to regulate protein function in living cells using synthetic small molecules, Cell, 126(5):995-1004.

DeRose et al., Mar. 2013, Manipulating signaling at will: chemically-inducible dimerization (CID) techniques resolve problems in cell biology, Pflugers Arch. 465(3):409-417.

Graef et al., 1997, Proximity and orientation underlie signaling by the non-receptor tyrosine kinase ZAP70, EMBO J. 16(18):5618-5628.

(Continued)

*Primary Examiner* — Christine J Saoud
*Assistant Examiner* — Jon M Lockard
(74) *Attorney, Agent, or Firm* — Knobbe, Martens, Olson & Bear LLP

(57) ABSTRACT

The present application relates to compositions comprising fusion proteins and cells expressing the proteins. The application further relates to methods of using the fusion proteins, cells, and compositions for modulating cell signaling and for selective expansion of cells.

26 Claims, 30 Drawing Sheets

Specification includes a Sequence Listing.

(56) References Cited

U.S. PATENT DOCUMENTS

| | | |
|---|---|---|
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger et al. |
| 5,432,272 A | 7/1995 | Benner et al. |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr et al. |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,658,776 A | 8/1997 | Flotte et al. |
| 5,663,312 A | 9/1997 | Chaturvedula et al. |
| 5,677,437 A | 10/1997 | Teng et al. |
| 5,677,439 A | 10/1997 | Weis et al. |
| 5,688,941 A | 11/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,786,211 A | 7/1998 | Johnson et al. |
| 5,830,653 A | 11/1998 | Froehler et al. |
| 5,871,982 A | 2/1999 | Wilson et al. |
| 6,005,096 A | 12/1999 | Matteucci et al. |
| 6,165,787 A † | 12/2000 | Crabtree |
| 6,258,595 B1 | 7/2001 | Gao et al. |
| 6,287,860 B1 | 9/2001 | Monia et al. |
| 2003/0158403 A1 | 8/2003 | Manoharan |
| 2010/0034777 A1 | 2/2010 | Wandless et al. |
| 2014/0068797 A1 | 3/2014 | Doudna |
| 2016/0311901 A1 | 10/2016 | Jarjour |
| 2017/0166877 A1 | 6/2017 | Bayle et al. |
| 2017/0175128 A1 | 6/2017 | McPherson |
| 2017/0176128 A1 | 6/2017 | McPherson |
| 2021/0340573 A1 | 11/2021 | Scharenberg et al. |

FOREIGN PATENT DOCUMENTS

| | | |
|---|---|---|
| WO | WO 95/13365 | 5/1995 |
| WO | WO 95/13392 | 5/1995 |
| WO | WO 96/17947 | 6/1996 |
| WO | 96/23881 A1 † | 8/1996 |
| WO | 96/24671 A1 † | 8/1996 |
| WO | WO 97/06243 | 2/1997 |
| WO | WO 97/08298 | 3/1997 |
| WO | WO 97/09441 | 3/1997 |
| WO | WO 97/21825 | 6/1997 |
| WO | WO 99/11764 | 3/1999 |
| WO | WO 99/36553 | 7/1999 |
| WO | WO 08/006588 | 1/2008 |
| WO | 2008/097875 A1 † | 8/2008 |
| WO | WO 13/123061 | 8/2013 |
| WO | WO 13/176772 | 11/2013 |
| WO | 2014/127261 A1 † | 8/2014 |
| WO | WO 2014/127261 A1 | 8/2014 |
| WO | 2015/017214 A1 † | 2/2015 |
| WO | WO 15/017214 | 2/2015 |
| WO | WO 15/090229 | 6/2015 |
| WO | 2016/098078 A2 † | 6/2016 |
| WO | WO 2016/098078 A2 | 6/2016 |
| WO | 2016/127257 A1 † | 8/2016 |
| WO | WO 16/201047 | 12/2016 |
| WO | 2017/029512 A1 † | 2/2017 |
| WO | WO 17/029512 | 2/2017 |
| WO | 2017/068360 A1 † | 4/2017 |
| WO | WO 18/111834 | 6/2018 |
| WO | WO 18/161038 | 9/2018 |
| WO | WO 19/210281 | 10/2019 |
| WO | WO 20/097582 | 5/2020 |

OTHER PUBLICATIONS

Kanamori et al., Nov. 2016, Induced regulatory T cells; their development, stability, and applications, Trends in Immunology, 37(11):803-811.

Li et al., 2002, A novel conditional Akt 'survival switch' reversibly protects cells from apoptosis, Gene Therapy. 9(4):233-244.

Ogawa et al., Aug. 29, 2013, Construction of unnatural heterodimeric receptor based on IL-2 and IL-t receptor subunits, Biotechnol Prog. 29(6):1512-1518, 2013.

Schlessinger et al., Sep. 20, 2002, Ligand-induced, receptor-mediated dimerization and activation of EGF receptor, Cell, 110(6):669-672.

Sogo et al., 2008, Selective expansion of genetically modified T cells using an antibody/interleukin-2 receptor chimera, J Immunol Methods. 337(1):16-23.

Vivien et al., Mar. 31, 1995, Signaling activity of homologous and heterologous transforming growth factor-β receptor kinase complexes, J Biol Chem. 270(13):7134-7141.

(56) References Cited

OTHER PUBLICATIONS

Wells et al., Feb. 26, 1999, Transforming growth factor-β induces formation of dithiothreitol-resistant type I/type II receptor complex in live cells, J Biol Chem. 274(9):5716-5722.
Wrana et al. Dec. 11, 1992, TGFβ signals through a heteromeric protein kinase receptor complex, Cell. 71(6):1003-1014.
Altschul et al., 1996, [27] Local alignment statistics, Methods in Enzymology, 266:460-480.
Angart et al., 2013, Design of siNRA therapeutics from the molecular scale, Pharmaceuticals, 6(4):440-468.
Ausubel et al., ed., 1987, Current Protocols in Molecular Biology New York, NY: Wiley (TOC).
Ayuso et al., 2010, Production, purification and characterization of adeno-associated vectors, Curr. Gene Ther., 10(6):423-436.
Bayle et al., 2006, Rapamycin analogs with differential binding specificity permit orthogonal control of protein activity, Chem. Biol., 13(1):99-107.
Behike, 2008, Chemical modification of siRNAs for in vivo use, Oligonucleotides, 18(4):305-319.
Braasch et al., Apr. 9, 2002, Novel antisense and peptide nucleic acid strategies for controlling gene expression, Biochemistry, 41(14):4503-4510.
Bramsen et al., Aug. 2012, Development of therapeutic-grade small interfering RNAs by chemical engineering, Front. Genet., 3(154):1-22.
Burnett et al., Sep. 2011, Current progress of siRNA/shRNA therapeutics in clinical trials, Biotechnol. J., 6(9):1130-1146.
Chen et al., May 1995, Identification of an 11-kDa FKBP12-rapamycin-binding domain within the 289-kDa FKBP12-rapamycin-associated protein and characterization of a critical serine residue, Proc. Natl. Acad. Sci. U.S.A., 92(11):4947-4951.
Chernolovskaya et al., 2010, Chemical modification of siRNA, Curr. Opin. Mol Ther., 12(2):158-167.
Choi et al., 1996, Structure of the FKBP12-rapamycin complex interacting with the binding domain of the human FRAP, Science, 273(5272):239-242.
Fonfara et al., 2014, Phylogeny of Cas9 determines functional exchangeability of dual-RNA and Cas9 among orthologous type II CRISPR-Cas systems, Nucl. Acids Res., 42(4):2577-2590.
Fucini et al., 2012, Adenosine modification may be preferred for reducing siRNA immune stimulation, Nucleic Acid Ther., 22(3):205-210.
Gaglione et al., 2010, Recent progress in chemically modified siRNAs, Mini Rev. Med. Chem., 10(7):578-595.
Gebeyehu et al., 1987, Novel biotinylated nucleotide—analogs for labeling and colorimetric detection of DNA, Nucl Acids Res., 15(11):4513-4534.
Genesis, 2001, 30(3), TOC.
Grupp et al., 2013. Chimeric antigen receptor-modified T cells for acute lymphoid leukemia. N Engl J Med 368:1509-1518.
Heasman, 2002, Morpholine oligos: making sense of antisense? Dev. Biol., 243(2):209-214.
Hermonat et al., Oct. 1984, Use of adeno-associated virus as a mammalian DNA cloning vector: transduction of neomycin resistance into mammalian tissue culture cells, Proc. Natl. Acad. Sci. U.S.A., 81(2):6466-6470.
Jinek et al., Aug. 17, 2012, A programmable dual-RNA-guided DNA endonuclease in adaptive bacterial immunity, Science, 337(6096):816-821.
Judge et al., 2006, Design of noninflammatory synthetic siRNA medicating potent gene silencing in vivo, Mol. Ther., 13:494-505.
Judge et al., Feb. 2008, Hum. Gene Ther., Overcoming the innate immune response to small interfering RNA, 19(2):111-124.
Kabanov et al., Jan. 1990, A new class of antivirals: antisense oligonucleotides combined with a hydrophobic substituent effectively inhibit influenza virus reproduction and synthesis of virus-specific proteins in MDCK cells, FEBS Lett., 259(2):327-330.
Kalos et al., 2011, T cells with chimeric antigen receptors have potent antitumor effects and can establish memory in patients with advanced leukemia, Sci. Transl. Med. 3(95):95ra73.

Kanasty et al., 2012, Action and reaction: the biological response to siRNA And its delivery vehicles, Mol. Ther., 20(3):513-524.
Kariko et al., Aug. 2005, Suppression of RNA recognition by toll-like receptors; the impact of nucleoside modification and the evolutionary origin of NRA, Immunity, 23(2):165-175.
Kim, et al., May 11, 2007, NMR Structural Studies of Interaction of a Small, Nonpeptidyl Tpo Mimic with the Thrombopoietin Receptor Extracellular Juxtamembrane and Transmembrane Domains, J Biol Chem, 282(19):14253-14261.
Kole et al., 2012, RNA therapeutics: beyond RNA interference and antisense oligonucleotides, Nat. Rev. Drug Disc., 11(2):125-140.
Kormann et al., 2011, Expression of therapeutic proteins after delivery of chemically modified mRNA in mice, Nat. Biotechnol., 29:154-157.
Lacerra et al., Aug. 15, 2000, Restoration of hemoglobin A synthesis in erythroid cells from peripheral blood of thalassemic patients, Proc. Natl. Acad. Sci. U.S.A., 97(17):9591-9596.
Lebkowski, et al., Oct. 1988, Adeno-associated virus: a vector system for efficient introduction and integration of DNA into a variety of mammalian cell types, Mol. Cell. Biol., 8(10):3988-3996.
Letsinger et al., Sep. 1989, Cholesteryl-conjugated oligonucleotides: synthesis, properties, and activity as inhibitors of replication of human immunodeficiency virus in cell culture, Proc. Natl. Acad. Sci. U.S.A., 86(17):6553-6556.
Love et al., 2010, Lipid-like materials for low-dose, in vivo gene silencing, Proc. Nat. Acad. Sci. U.S.A., 107(5):1864-1869.
Ma et al., 2014, Pol III promoters to express small RNAs: delineation of transcription initiation, Mol. Ther.—Nucleic Acids 3:e161, doi:10.1038/mtna.2014.12.
McLaughlin et al., Jun. 1988, Adeno-associated virus general transduction vectors: analysis of proviral structures, J. Virol., 62(6):1963-1973.
Mietzsch et al., 2014, OneBac: platform for scalable and high-titer production of adeno-associated virus serotype 1-12 vectors for gene therapy, Hum. Gene Ther., 25(3):212-222.
Mietzsch et al., 2015, OncBac 2.0: Sf9 cell lines for production f AAV5 vectors with enhanced infectivity and minimal encapsidation of foreign DNA, Hum. Gene Ther., 26(10):688-697.
Mietzsch et al., 2017, OneBac 2.0: Sf9 cell lines for production of AAV1, AAV2, and AAV8 vectors with minimal encapsidation of foreign DNA, Hum. Gene Ther. Method, 28(1):15-22.
Nasevicius et al., Oct. 2000, Effective targeted gene 'knockdown' in zebrafish. Nat. Genet., 26(2):216-220.
Nielsen et al., 1991, Sequence-selective recognition of DNA by strand displacement with a thymine-substitute polyamide, Science, 254(5037):1497-1500.
Oberhauser et al., 1992, Effective incorporation of 2'-O-methyl-oligoribonucelotides into liposomes and enhanced cell association through modification with thiochoiesterol, Nucl. Acids Res., 20(3):533-538.
Peer et al., 2011, Special delivery: targeted therapy with small RNAs, Gene Ther., 18:1127-1133.
Restifo et al., 2012, Adoptive immunotherapy for cancer: harnessing the T cell response, Nat. Rev. Immunol. 12(4):269-281.
Sambrook et al., 2012, Molecular Cloning: A Laboratory Manual (4$^{th}$ ed.), Cold Spring Harbor, NY: Cold Spring Harbor Laboratory (TOC).
Samulski et al., 1982, Cloning of adeno-associated virus into pBR322: rescue of intact virus from the recombinant plasmid in human ceils, Proc. Natl. Acad. Sci. U.S.A., 79(6):2077-2081.
Samulski et al., 1989, Helper-free stocks of recombinant adeno-associated viruses: normal integration does not require viral gene expression, J. Virol., 63(9):3822-3828.
Sander et al., Apr. 2014, CRPSPR-Cas systems for genome editing, regulation and targeting, Nat. Biotechnol., 32(4):347-355.
Sapranauskas et al., 2011, The streptococcus thermophilus CRISPR/Cas system provides immunity in Escherichia coli, Nucl. Acids Res., 39(21):9275-9282.
Senapathy et al., Apr. 10, 1984, Molecular cloning of adeno-associate virus variant genomes and generation of infectious virus by recombination in mammalian cells, J. Biol. Chem., 259(7):4661-4666.

(56) References Cited

OTHER PUBLICATIONS

Shea et al., 1990, Synthesis, hybridization properties and antiviral activity of lipid-oligodeoxynucleotide conjugates, Nucl. Acids Res., 18(13):3777-3783.

Soutschek et al., Nov. 11, 2004, Therapeutic silencing of an endogenous gene by systemic administration of modified siRNAs, Nature, 432:173-178.

Stankunas et al., Dec. 2003, Conditional protein alleles using knockin mice and a chemical inducer of dimerization, Mol. Cell., 12(6):1615-1624.

Tratschin et al., 1984, A human parvovirus, adeno-associated virus, as a eucaryotic vector: transient expression and encapsidation of the procaryotic gene for chloramphenicol acetyltransferase, Mol. Cell. Biol., 4(10):2072-2081.

Tratschin et ai., Nov. 1985, Adeno-associated virus vector for high-frequency integration, expression, and rescue of genes in mammalian ceils, Mol. Cell. Biol., 5(11):3251-3260.

Vilella-Bach et al., Feb. 12, 1999, The FKBP12-reapamycin-binding domain is required for FSBP12-rapamycin-associated protein kinase activity and $G_1$ progression, J. Biol. Chem., 274(7):4266-4272.

Volkov et al., 2099, Selective protection of nuclease-sensitive sites in siRNA prolongs silencing effect, Oligonucleotides, 19(2):191-202.

Warren et al., 2010, Highly efficient reprogramming to pluripotency and directed differentiation of human cells with synthetic modified mRNA, Cell Stem Cell, 7(5):618-630.

Winkler, 2013, Oligonucleotide conjugates for therapeutic applications, Ther. Deliv., 4(7):791-809.

International Search Report for PCT/US2017/065746 dated May 23, 2018.

Veverka et al., Structural Characterization of the interaction of mTOR with phosphatidic acid and a novel class of inhibitor: compelling evidence for a central role of the FRB domain in small molecule-mediated regulation of mTOR, Oncogene, 27(5):585-595.

Choi et al., "Structure of the FKBP12-rapamycin complex interacting with the binding domain of human FRAP" *Science*. 1996. 273(5272):239-242.

Kapp et al., Post-Targeting Functions of Signal Peptides. In: Madame Curie BioScience Database. Landes Bioscience (Austin, TX 2000-2013).

Liang et al., "1NSG. The Structure of the Immunophilin-Immunosuppressant FKBP12-Rapamycin Complex Interacting With Human Frap", PDB DOI: 10.2210/pdb1NSG/pdb, Mar. 18, 1998.

Liang et al., "Refined structure of the FKBP12-rapamycin-FRB ternary complex at 2.2 A resolution" *Acta Crystallogr D Biol Crystallogr*. 1999. 55(4):736-744.

Ruiz-Medina et al., Interleukin-2 Receptor B Thr-450 Phosphorylation Is a Positive Regulator for Receptor Complex Stability and Activation of Signaling Molecules, *J Biol Chem*. 2015. 290(34):20972-20983.

† cited by third party

METHODS OF EXOGENOUS DRUG ACTIVATION OF CHEMICAL-INDUCED SIGNALING COMPLEXES EXPRESSED IN ENGINEERED CELLS IN VITRO AND IN VIVO

INCORPORATION BY REFERENCE TO A PRIORITY APPLICATION

This application is a U.S. National Phase Application of PCT International Application Number PCT/US2017/065746, filed on Dec. 12, 2017, designating the United States of America and published in the English language, which is an International Application of and claims the benefit of priority to U.S. Provisional Application No. 62/433,540, filed on Dec. 13, 2016. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SubSeqListingSCRI130NP, created Nov. 13, 2019, which is approximately 80,311 bytes in size. The information is the electronic format of the Sequence Listing and is hereby expressly incorporated by reference in its entirety.

FIELD

The present disclosure relates to compositions and methods for synthetic chemical-induced signaling. In particular, the compositions include a general architecture for generating physiologically functional synthetic chemical-induced signaling complexes, as well as, functional chemical-induced signaling complexes. Some embodiments provide a chemical-induced signaling complex that includes a multi-component protein, in which two components, normally existing as monomers, are brought together in the presence of a ligand to generate an active signaling complex, which activates signaling pathways in the cytoplasm of the cell. Further provided are methods of using such compositions for activating a cellular signaling pathway in a cell. Also provided are methods of using the compositions for selectively expanding a population of cells.

BACKGROUND

Chimeric antigen receptors (CARs) are engineered receptors used to genetically engineer T cells for use in adoptive cellular immunotherapy (see Pule et al., *Cytother.* 5:3, 2003; Restifo et al., Nat. Rev. Immunol. 12:269, 2012). Antigen binding stimulates the signaling domains on the intracellular segment of the CAR, thereby activating signaling pathways. CAR-based adoptive cellular immunotherapy has been used to treat cancer patients with tumors refractory to conventional standard-of-care treatments (see Grupp et al., *N. Engl. J. Med.* 368:1509, 2013; Kalos et al., *Sci. Transl. Med.* 3:95ra73, 2011).

Cells have various receptors on their surface for responding to extracellular signals that involve intercellular communication. Signal transduction of receptors has been studied extensively and receptors are involved in numerous signaling pathways. There remains a need for new compositions and methods that allow for one to transduce a desired signal through a synthetic complex that cannot be activated through a normal physiological pathway, thus providing a mechanism for activating signaling only within in a desired and specifically engineered population of cells.

SUMMARY

A dimerization activated receptor initiation complex (DARIC) has been developed, which provides a binding component and a signaling component that are each expressed as separate fusion proteins but contain an extracellular multimerization mechanism (bridging factor) for recoupling of the two functional components on a cell surface (see U.S. Pat. Appl. No. 2016/0311901, hereby expressly incorporated by reference in its entirety). Importantly, the bridging factor in the DARIC system forms a heterodimeric receptor complex, which does not produce significant signaling on its own. The described DARIC complexes only initiate physiologically relevant signals following further co-localization with other DARIC complexes. Thus, they do not allow for the selective expansion of desired cell types without a mechanism for further multimerization of DARIC complexes (such as by e.g., contact with a tumor cell that expresses a ligand bound by a binding domain incorporated into one of the DARIC components).

Accordingly, several aspects described herein relate to compositions and methods including a chemical-induced signaling complex (CISC). In some aspects, the compositions and methods may be used for the selective expansion of a desired population of cells.

Some embodiments described herein relate to a protein sequence encoding a chemical-induced signaling complex (CISC). In some embodiments, the protein sequence comprises a first sequence, wherein the first sequence encodes a first CISC component. In some embodiments, the first CISC component comprises a first extracellular binding domain or a portion thereof, a hinge domain, a transmembrane domain, and a signaling domain or a portion thereof. In some embodiments, the protein sequence comprises a second sequence. In some embodiments, the second sequence encodes a second CISC component. In some embodiments, the second CISC component comprises a second extracellular binding domain or portion thereof, a hinge domain, a transmembrane domain, and a signaling domain or portion thereof. In some embodiments, the first CISC component and the second CISC component are positioned such that when expressed, they dimerize in the presence of a ligand. In some embodiments, the first and second CISC components dimerize to form a heterodimer or a homodimer. In some embodiments, the dimeric CISC is a synthetic CISC. In some embodiments, the first and second extracellular domains are N-terminal to the transmembrane domain. In some embodiments, the first extracellular binding domain or a portion thereof comprises an FK506 binding protein (FKBP) domain. In some embodiments, the second extracellular binding domain or portion thereof comprises an FKBP rapamycin binding (FRB) domain or a portion thereof.

In some embodiments, the transmembrane domain of the first and second CISC components comprises a natural transmembrane domain. In some embodiments, the transmembrane domain of the first and second CISC components comprises an IL-2 receptor transmembrane domain. In some embodiments, the signaling domain or a portion thereof of the first and second CISC components comprises one or more concatenated cytoplasmic signaling domains. In some embodiments, the signaling domain or a portion thereof of the first and second CISC components comprises a cytokine signaling domain or an antigen receptor signaling domain. In some embodiments, the signaling domain of the first CISC component comprises an interleukin-2 receptor subunit gamma (IL2Rg) domain. In some embodiments, the signaling domain of the second CISC component comprises an interleukin-2 receptor subunit beta (IL2Rb) domain.

In some embodiments, one of the extracellular binding domains comprises an FKBP domain and the other extracellular binding domain comprises an FRB domain. In some embodiments, the extracellular binding domains are configured to simultaneously bind to a ligand.

In some embodiments, one extracellular binding domain comprises a cereblon thalidomide binding domain and the other extracellular binding domain comprises a domain that interacts with the cereblon thalidomide binding domain when it is bound to an IMID-class drug (e.g. thalidomide, pomalidomide, lenalidomide or related analogues). In some embodiments, the extracellular binding domains are configured to simultaneously bind to the IMID ligand.

In some embodiments, one of the extracellular binding domain comprises one member of a heterodimerizing protein domain pair, and the other extracellular binding domain comprises the other component of a heterodimerization domain pair, and the domains are configured to bind to a ligand e.g., by simultaneous binding.

In some embodiments, the ligand is an antibody or a portion thereof, such as a binding fragment, a protein, a small molecule, or a drug. In some embodiments, the ligand is rapamycin or a rapalog, such as everolimus, CCI-779, C20-methallylrapamycin, C16-(S)-3-methylindolerapamycin, C16-iRap, AP21967, sodium mycophenolic acid, benidipine hydrochloride, AP23573, AP1903, or metabolites, derivatives, and/or combinations thereof. In some embodiments, the ligand is an IMID-class drug (e.g. thalidomide, pomalidomide, lenalidomide or related analogues). In some embodiments, the ligand is present or provided in an amount from 0.05 nM to 100 nM such as e.g., 0.05 nM, 0.1 nM, 0.5. nM, 1.0 nM, 5.0 nM, 10.0 nM, 15.0 nM, 20.0 nM, 25.0 nM, 30.0 nM, 35.0 nM, 40.0 nM, 45.0 nM, 50.0 nM, 55.0 nM, 60.0 nM, 65.0 nM, 70.0 nM, 75.0 nM, 80.0 nM, 90.0 nM, 95.0 nM, or 100 nM or an amount that is within a range defined by any two of the aforementioned amounts.

In some embodiments, the first sequence comprises an amino acid sequence set forth in SEQ ID NO: 1. In some embodiments, the first sequence comprises an amino acid sequence set forth in SEQ ID NO: 3, 5, or 7. In some embodiments, the second sequence comprises an amino acid sequence set forth in SEQ ID NO: 2. In some embodiments, the second sequence comprises an amino acid sequence set forth in SEQ ID NO: 4, 6, 8, or 9. Some embodiments concern nucleic acids encoding the amino acid sequences of SEQ ID NOs: 1, 2, 3, 4, 5, 6, 7, 8 and 9.

Some embodiments provided herein relate to an expression vector. In some embodiments, the expression vector comprises a nucleic acid encoding a protein sequence encoding a dimeric chemical-induced signaling complex (CISC). In some embodiments, the expression vector comprises a nucleic acid encoding a protein sequence comprising a first protein sequence, wherein the first protein sequence encodes a first CISC component. In some embodiments, the nucleic acid encoding the first sequence comprises a sequence encoding a first extracellular binding domain or a portion thereof, a hinge domain, a transmembrane domain, and a signaling domain or portions thereof. In some embodiments, the expression vector comprises a nucleic acid encoding a protein sequence comprising a second protein sequence, wherein the second protein sequence encodes a second CISC component. In some embodiments, the nucleic acid encoding the second sequence comprises a sequence encoding a second extracellular binding domain or a portion thereof, a hinge domain, a transmembrane domain, and a signaling domain or portions thereof. In some embodiments, the expression vector comprises a nucleic acid encoding the first protein sequence or the second protein sequence. In some embodiments, the expression vector comprises nucleic acid encoding the first sequence and the second protein sequence. In some embodiments, the vector is RNA or DNA. In some embodiments, the vector is a lentiviral vector or an adeno-associated viral (AAV) vector. In some embodiments, the expression vector is a nucleic acid sequence set forth in SEQ ID NO: 6, SEQ ID NO: 7, or SEQ ID NO: 8.

In some embodiments, the expression vector comprises a nucleic acid sequence that further comprises a promoter. In some embodiments, the promoter is an inducible promoter or a constitutive promoter.

Some embodiments provided herein relate to a cell, such as a mammalian cell, for chemical-induced signaling complex expression. In some embodiments, the cell, such as a mammalian cell, comprises a protein sequence as described herein or an expression vector described herein. Thus, in some embodiments, the cell, such as a mammalian cell, comprises a protein sequence encoding the components of a chemical-induced signaling complex (CISC). In some embodiments, the protein sequence comprises a first sequence, wherein the first sequence encodes a first component of a CISC. In some embodiments, the first component of a CISC comprises a first extracellular binding domain or portion thereof, a hinge domain, a transmembrane domain, and a signaling domain or portions thereof. In some embodiments, the protein sequence comprises a second sequence. In some embodiments, the second sequence encodes a second component of a CISC. In some embodiments, the second CISC component comprises a second extracellular binding domain or a portion thereof, a hinge domain, a transmembrane domain, and a signaling domain or portions thereof. In some embodiments, the cell, such as a mammalian cell, comprises an expression vector comprising a nucleic acid encoding a protein sequence encoding a component of a CISC. In some embodiments, the expression vector comprises a nucleic acid encoding a protein sequence comprising a first protein sequence, wherein the first protein sequence encodes a first component of a CISC. In some embodiments, the nucleic acid encoding the first sequence comprises a sequence encoding a first extracellular binding domain or a portion thereof, a hinge domain, a transmembrane domain, and a signaling domain or portions thereof. In some embodiments, the expression vector comprises a nucleic acid encoding a protein sequence comprising a second protein sequence, wherein the second protein sequence encodes a second component of a CISC. In some embodiments, the nucleic acid encoding the second sequence comprises a sequence encoding a second extracellular binding domain or a portion thereof, a hinge domain, a transmembrane domain, and a signaling domain or portions thereof. In some embodiments, the expression vector comprises a nucleic acid encoding the first protein sequence or the second protein sequence. In some embodiments, the expression vector comprises nucleic acid encoding the first sequence and the second protein sequence. In some embodiments, the vector is RNA or DNA. In some embodiments, the vector is a lentiviral vector or an adeno-associated viral (AAV) vector.

In some embodiments, the cell, such as a mammalian cell, is a precursor T cell or a T regulatory cell. In some embodiments, the cell, such as a mammalian cell, is a hematopoietic stem cell. In some embodiments, the cell is a CD34+, CD8+, or a CD4+ cell. In some embodiments, the cell is a CD8+T cytotoxic lymphocyte cell selected from the group consisting of naïve CD8+ T cells, central memory CD8+ T cells, effector memory CD8+ T cells, and bulk CD8+ T cells or any combination thereof. In some embodiments, the cell is a CD4+T helper lymphocyte cell selected from the group consisting of naïve CD4+ T cells, central memory CD4+ T cells, effector memory CD4+ T cells, and bulk CD4+ T cells or any combination thereof.

Some embodiments provided herein relate to a method of activating a signal into the interior of a cell, such as a mammalian cell, In some embodiments, the method comprises providing a cell, such as a mammalian cell, as described herein, expressing the protein sequence encoding the components of the synthetic CISC as described herein, or expressing the expression vector as described herein in the cell, and contacting the cell with a ligand, thereby causing the first and second CISC components to dimerize, which transduces a signal into the interior of the cell.

Accordingly, in some embodiments, the method of activating a signal into an interior of a cell, such as a mammalian cell, comprises providing a cell, such as a mammalian cell, that comprises one or more protein sequences encoding components of a CISC. In some embodiments, the protein sequence comprises a first sequence, wherein the first sequence encodes a first component of a CISC. In some embodiments, the first component of a CISC comprises a first extracellular binding domain or a portion thereof, a hinge domain, a transmembrane domain, and a signaling domain or portions thereof. In some embodiments, the protein sequence comprises a second sequence. In some embodiments, the second sequence encodes a second component of a CISC. In some embodiments, the second component of a CISC comprises a second extracellular binding domain or a portion thereof, a hinge domain, a transmembrane domain, and a signaling domain or portions thereof. In some embodiments, the method of activating a signal into an interior of a cell, such as a mammalian cell, comprises providing a cell, such as a mammalian cell, that comprises an expression vector comprising a nucleic acid encoding a protein sequence encoding a dimeric CISC. In some embodiments, the expression vector comprises a nucleic acid encoding a protein sequence comprising a first protein sequence, wherein the first protein sequence encodes a first component of a CISC. In some embodiments, the nucleic acid encoding the first sequence comprises a sequence encoding a first extracellular binding domain or a portion thereof, a hinge domain, a transmembrane domain, and a signaling domain or portions thereof. In some embodiments, the expression vector comprises a nucleic acid encoding a protein sequence comprising a second protein sequence, wherein the second protein sequence encodes a second component of a CISC. In some embodiments, the nucleic acid encoding the second sequence comprises a sequence encoding a second extracellular binding domain or a portion thereof, a hinge domain, a transmembrane domain, and a signaling domain or portions thereof. In some embodiments, the expression vector comprises a nucleic acid encoding the first protein sequence or the second protein sequence. In some embodiments, the expression vector comprises nucleic acid encoding the first sequence and the second protein sequence. In some embodiments, the vector is RNA or DNA. In some embodiments, the vector is a lentiviral vector or an adeno-associated viral (AAV) vector. In some embodiments, whether the cell, such as a mammalian cell, comprises the protein sequence or the expression vector, the method further comprises expressing the protein sequence encoding a heterodimeric CISC, or expressing the expression vector, and contacting the cell with a ligand, thereby causing the first and second components of a CISC to dimerize, which transduces a signal into the interior of the cell.

In some embodiments, the ligand comprises an antibody or a binding portion thereof, a protein, a small molecule, or a drug. In some embodiments, the ligand is rapamycin or a rapalog, such as everolimus, CCI-779, C20-methallylrapamycin, C16-(S)-3-methylindolerapamycin, C16-iRap, AP21967, sodium mycophenolic acid, benidipine hydrochloride, AP23573, or AP1903, or metabolites, derivatives, and/or combinations thereof. In some embodiments, the ligand is an immunomodulatory imide drug (IMID)-class drug (e.g. thalidomide, pomalidomide, lenalidomide or related analogues). In some embodiments, the ligand is present or provided in an amount of 0.05 nM to 100 nM such as e.g., 0.05 nM, 0.1 nM, 0.5. nM, 1.0 nM, 5.0 nM, 10.0 nM, 15.0 nM, 20.0 nM, 25.0 nM, 30.0 nM, 35.0 nM, 40.0 nM, 45.0 nM, 50.0 nM, 55.0 nM, 60.0 nM, 65.0 nM, 70.0 nM, 75.0 nM, 80.0 nM, 90.0 nM, 95.0 nM, or 100 nM or an amount that is within a range defined by any two of the aforementioned amounts. In some embodiments, the transduction of the signal affects cytokine signaling. In some embodiments, the transduction of the signal results in a signal that phenocopies interleukin-2 receptor (IL2R) signaling. In some embodiments, the transduction of the signal affects phosphorylation of a downstream target of a cytokine receptor. In some embodiments, following contact with the ligand, cells, such as mammalian cells, expressing the chemical-induced signaling complex are selectively expanded from a heterogeneous population of cells. In some embodiments, the ligand comprises rapamycin, and the cells, such as a mammalian cell, expressing the chemical-induced signaling complex are selectively expanded in vitro or in vivo by selectively inducing proliferation in chemical-induced signaling complex-expressing cells, while the rapamycin, preferably simultaneously, causes an anti-proliferative effect in non-chemical-induced signaling complex expressing cells, such as mammalian cells. In some embodiments, the selectively expanding cells, such as mammalian cells, have undergone two distinct gene targeting events. In some embodiments, each gene targeting event endows the cell, such as a mammalian cell, with one component of a chemical-induced signaling complex pair, such that only cells that have undergone both gene targeting events are able to expand following contact with the ligand.

Some embodiments provided herein relate to a protein sequence encoding components of a chemical-induced signaling complex component for homodimerization. In some embodiments, the protein sequence comprises a first sequence. In some embodiments, the first sequence encodes a first chemical-induced signaling complex component comprising a homodimerizing domain or a portion thereof, a hinge domain, a transmembrane domain, and an interleukin-2 receptor subunit gamma (IL2Rg) signaling domain or portions thereof. In some embodiments, the protein sequence comprises second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the first chemical-induced signaling complex component and the second chemical-induced signaling complex component are positioned such that when expressed, they form a population of 25% first chemical-induced signaling complex homodimers, 25% second chemical-induced signaling complex homodimers, and 50% of first/second chemical-induced signaling complex heterodimers in the presence of a ligand configured to bridge the homodimerizing domain.

In some embodiments, the first sequence comprises an amino acid sequence set forth in SEQ ID NO: 11. In some embodiments, the second sequence comprises an amino acid sequence set forth in SEQ ID NOs: 10 or 12. Some embodiments concern nucleic acids encoding the amino acid sequences of SEQ ID NOs: 10, 11, and 12.

In some embodiments, the signaling domain or a portion thereof of the first and second chemical-induced signaling complex components comprises one or more concatenated cytoplasmic signaling domains. In some embodiments, the homodimerizing domain comprises an FKBP domain or a mutant thereof or portions thereof, configured to bind a ligand, preferably simultaneously, such as AP1903 or a related rapalog, sodium mycophenolic acid, benidipine hydrochloride, or AP23573, or metabolites, derivatives, and/or combinations thereof. In some embodiments, the ligand is an IMID-class drug (e.g. thalidomide, pomalidomide, lenalidomide or related analogues).

Some embodiments provided herein relate to an expression vector for homodimeric CISC component expression comprising a nucleic acid encoding the first and/or second sequence of the protein sequence as provided herein. Accordingly, in some embodiments, the expression vector comprises a nucleic acid encoding a protein sequence encoding a chemical-induced signaling complex as set forth in SEQ ID NOs: 10, 11, and 12. In some embodiments, the expression vector encodes a first sequence. In some embodiments, the first sequence encodes a first chemical-induced signaling complex component comprising a homodimerizing domain or a portion thereof, a hinge domain, a transmembrane domain, and an interleukin-2 receptor subunit gamma (IL2Rg) signaling domain or portions thereof. In some embodiments, the expression vector encodes a second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the vector is RNA or DNA. In some embodiments, the vector is a lentiviral vector or an adeno-associated viral (AAV) vector. In some embodiments, the expression vector further comprises a promoter. In some embodiments, the promoter is an inducible promoter or a constitutive promoter.

Some embodiments provided herein relate to a cell, such as a mammalian cell, for homodimeric chemical-induced signaling complex expression. In some embodiments, the cell, such as a mammalian cell, comprises the protein sequence as described herein for homodimerizing component expression or the expression vector as described herein for homodimerizing component expression. Thus, in some embodiments a cell, such as a mammalian cell, is provided, which comprises a protein sequence encoding chemical-induced signaling complex components for homodimerization. In some embodiments, the protein sequence comprises a first sequence. In some embodiments, the first sequence encodes a first chemical-induced signaling complex comprising a homodimerizing domain or a portion thereof, a hinge domain, a transmembrane domain, and an interleukin-2 receptor subunit gamma (IL2Rg) signaling domain or portions thereof. In some embodiments, the protein sequence comprises second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the first chemical-induced signaling complex component and the second chemical-induced signaling complex component are positioned such that when expressed, they form a population of approximately 25% first chemical-induced signaling complex homodimers, 25% second chemical-induced signaling complex homodimers, and 50% of first/second chemical-induced signaling complex heterodimers in the presence of a ligand configured to bridge the homodimerizing domain. In some embodiments a cell, such as a mammalian cell, is provided, which comprises an expression vector for homodimeric chemical-induced signaling complex expression comprising a nucleic acid encoding the first and/or second sequence of the protein sequence as provided herein. Accordingly, in some embodiments, the expression vector comprises a nucleic acid encoding a protein sequence encoding a chemical-induced signaling complex. In some embodiments, the expression vector encodes a first sequence. In some embodiments, the first sequence encodes a first chemical-induced signaling complex component comprising a homodimerizing domain or a portion thereof, a hinge domain, a transmembrane domain, and an interleukin-2 receptor subunit gamma (IL2Rg) signaling domain or portions thereof. In some embodiments, the expression vector encodes a second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the vector is RNA or DNA. In some embodiments, the vector is a lentiviral vector or an adeno-associated viral (AAV) vector.

In some embodiments, the protein sequence for the homodimeric chemical-induced signaling complex comprises an amino acid sequence set forth in SEQ ID NO: 13 or SEQ ID NO: 14. Some embodiments concern nucleic acids encoding the amino acid sequences of SEQ ID NO: 13 and SEQ ID NO: 14.

In some embodiments, the chemical-induced signaling complex cell, such as a mammalian cell, is a precursor T cell or a T regulatory cell. In some embodiments, the cell, such as a mammalian cell, is a hematopoietic stem cell. In some embodiments, the cell is a CD34+, CD8+, or a CD4+ cell. In some embodiments, the cell is a CD8+T cytotoxic lymphocyte cell selected from the group consisting of naïve CD8+ T cells, central memory CD8+ T cells, effector memory CD8+ T cells, and bulk CD8+ T cells. In some embodiments, the cell is a CD4+T helper lymphocyte cell selected from the group consisting of naïve CD4+ T cells, central memory CD4+ T cells, effector memory CD4+ T cells, and bulk CD4+ T cells.

Some embodiments provided herein relate to a method of activating a signal into an interior of a cell, such as a mammalian cell, with a homodimerization chemical-induced signaling complex. In some embodiments, the method comprises providing the cell, such as a mammalian cell, as provided herein, expressing a protein sequence encoding a homodimeric chemical-induced signaling complex as provided herein or expressing the expression vector for the homodimeric chemical-induced signaling complex as provided herein, and contacting the cell with a dimerizing agent, thereby causing the first and second chemical-induced signaling complexes to dimerize, which transduces a signal into the interior of the cell. Accordingly, in some embodiments, the method comprises providing a cell, such as a mammalian cell, comprising the protein sequence as described herein for homodimeric CISC component expression or the expression vector as described herein for homodimeric CISC component expression. Thus, in some embodiments a cell, such as a mammalian cell, is provided, wherein the cell comprises a protein sequence encoding a chemical-induced signaling complex for homodimerization. In some embodiments, the protein sequence comprises a first sequence. In some embodiments, the first sequence encodes a first chemical-induced signaling complex component comprising a homodimerizing domain or a portion thereof, a hinge domain, a transmembrane domain, and an interleukin-2 receptor subunit gamma (IL2Rg) signaling domain or portions thereof. In some embodiments, the protein sequence comprises second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the first chemical-induced signaling complex component and the second chemical-induced signaling complex component are positioned such that when expressed, they form a population of approximately 25% first chemical-induced signaling complex homodimers, 25% second chemical-induced signaling complex homodimers, and 50% of first/second chemical-induced signaling complex heterodimers in the presence of a ligand configured to bridge the homodimerizing domain. In some embodiments a cell, such as a mammalian cell, is provided, wherein the cell comprises an expression vector for homodimeric CISC component expression comprising a nucleic acid encoding the first and/or second sequence of the protein sequence as provided herein. Accordingly, in some embodiments, the expression vector comprises a nucleic acid encoding a protein sequence encoding a chemical-induced signaling complex or components thereof. In some embodiments, the expression vector encodes a first sequence. In some embodiments, the first sequence encodes a first chemical-induced signaling complex component comprising a homodimerizing domain or a portion thereof, a hinge domain, a transmembrane domain, and an interleukin-2 receptor subunit gamma (IL2Rg) signaling domain or portions thereof. In some embodiments, the expression vector encodes a second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the vector is RNA or DNA. In some embodiments, the vector is a lentiviral vector or an adeno-associated viral (AAV) vector. In some embodiments, after providing said cell, such as a mammalian cell, the method further comprises expressing a protein sequence encoding the homodimeric chemical-induced signaling complex components as provided herein or expressing the expression vector for the homodimeric chemical-induced signaling complex components as provided herein, and contacting the cell with a dimerizing agent, thereby causing the first and second chemical-induced signaling complex components to dimerize, which transduces a signal into the interior of the cell.

In some embodiments, the dimerizing agent used is a ligand, such as rapamycin or a rapalog, such as everolimus, CCI-779, C20-methallylrapamycin, C16-(S)-3-methylindolerapamycin, C16-iRap, AP21967, sodium mycophenolic acid, benidipine hydrochloride, or AP23573, AP1903, or metabolites, derivatives, and/or combinations thereof. In some embodiments, the ligand is an IMID-class drug (e.g. thalidomide, pomalidomide, lenalidomide or related analogues). In some embodiments, the transduction of the signal affects cytokine signaling. In some embodiments, the transduction of the signal phenocopies interleukin-2 receptor (IL2R) signaling. In some embodiments, following contact with the dimerizing agent, cells, such as mammalian cells, expressing the chemical-induced signaling complex are selectively expanded from a heterogeneous population of cells. In some embodiments, rapamycin is the dimerizing agent, and is used to selectively expand a cell, such as a mammalian cell, population in vitro or in vivo by selectively inducing proliferation in chemical-induced signaling complex-expressing cells, while causing an anti-proliferative effect in non-chemical-induced signaling complex expressing cells.

Some embodiments provided herein relate to a protein sequence encoding a chemical-induced signaling complex component. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex component is positioned such that when expressed, it forms a population of homodimeric CISCs in the presence of a ligand configured to bridge the homodimerizing domains. In some embodiments, the signaling domain or a portion thereof of comprises one or more concatenated cytoplasmic signaling domain. In some embodiments, the homodimerizing domain comprises an FKBP domain or an FRB or a portion thereof configured to bind to a ligand, preferably simultaneously, such as rapamycin.

Some embodiments provided herein relate to an expression vector comprising the nucleic acid encoding the protein sequence, as provided herein. Accordingly, in some embodiments, the expression vector comprises a nucleic acid encoding a protein sequence encoding a chemical-induced signaling complex. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex component is positioned such that when expressed, it forms a population of homodimers in the presence of a ligand configured to bridge the homodimerizing domains. In some embodiments, the signaling domain or a portion thereof of comprises one or more concatenated cytoplasmic signaling domain. In some embodiments, the homodimerizing domain comprises an FKBP domain or an FRB or a portion thereof configured to bind to a ligand, preferably simultaneously, such as AP1903. In some embodiments, the expression vector further comprises a promoter. In some embodiments, the promoter is an inducible promoter or a constitutive promoter. In some embodiments, the vector is RNA or DNA. In some embodiments, the vector is a lentiviral vector or an adeno-associated viral (AAV) vector.

Some embodiments provided herein relate to a cell, such as a mammalian cell, for homodimeric chemical-induced signaling complex expression. In some embodiments, the cell, such as a mammalian cell, comprises the homodimerizing CISC component protein sequence as described herein or the expression vector encoding the nucleic acid sequence of the homodimeric protein sequence as described herein. Accordingly, in some embodiments, the cell, such as a mammalian cell, for homodimeric chemical-induced signaling complex expression comprises a protein sequence encoding a chemical-induced signaling complex. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex is positioned such that when expressed, it forms a population of homodimers in the presence of a ligand configured to bridge the homodimerizing domains. In some embodiments, the signaling domain or a portion thereof of comprises one or more concatenated cytoplasmic signaling domains. In some embodiments, the homodimerizing domain comprises an FKBP domain or an FRB or a portion thereof configured to bind to a ligand, preferably simultaneously, such as AP1903. In some embodiments, the cell, such as a mammalian cell, for homodimeric chemical-induced signaling complex expression comprises an expression vector comprises a nucleic acid encoding a protein sequence encoding a chemical-induced signaling complex component. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex component is positioned such that when expressed, it forms a population of homodimers in the presence of a ligand configured to bridge the homodimerizing domains. In some embodiments, the signaling domain or a portion thereof of comprises one or more concatenated cytoplasmic signaling domains. In some embodiments, the homodimerizing domain comprises an FKBP domain or an FRB or a portion thereof configured to bind to a ligand, preferably simultaneously, such as AP1903. In some embodiments, the expression vector further comprises a promoter. In some embodiments, the promoter is an inducible promoter or a constitutive promoter. In some embodiments, the vector is RNA or DNA. In some embodiments, the vector is a lentiviral vector or an adeno-associated viral (AAV) vector.

In some embodiments, the cell, such as a mammalian cell, is a precursor T cell or a T regulatory cell. In some embodiments, the cell, such as a mammalian cell, is a hematopoietic stem cell. In some embodiments, the cell is a CD34+, CD8+, or a CD4+ cell. In some embodiments, the cell is a CD8+T cytotoxic lymphocyte cell selected from the group consisting of naïve CD8+ T cells, central memory CD8+ T cells, effector memory CD8+ T cells, and bulk CD8+ T cells. In some embodiments, the cell is a CD4+T helper lymphocyte cell selected from the group consisting of naïve CD4+ T cells, central memory CD4+ T cells, effector memory CD4+ T cells, and bulk CD4+ T cells.

Some embodiments provided herein relate to a method of activating a signal into an interior of a cell, such as a mammalian cell. In some embodiments, the method comprises providing the cell, such as a mammalian cell, for homodimeric chemical-induced signaling complex components as provided herein, expressing a protein sequence encoding a homodimeric chemical-induced signaling complex component as provided herein or expressing the expression vector encoding a nucleic acid for homodimeric chemical-induced signaling complex component expression as provided herein, and contacting the cell with a dimerizing agent, thereby causing the first and second chemical-induced signaling complex components to dimerize, which transduces a signal into the interior of the cell. Accordingly, in some embodiments, the method comprises providing a cell, such as a mammalian cell, which comprises the homodimerizing CISC component protein sequences, as described herein or the expression vector encoding the nucleic acid sequence of the homodimeric CISC component protein sequences as described herein. Accordingly, in some embodiments, the cell for homodimeric chemical-induced signaling complex component expression comprises a protein sequence encoding a chemical-induced signaling complex component. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex component is positioned such that when expressed, it forms a population of homodimers in the presence of a ligand configured to bridge the homodimerizing domains. In some embodiments, the signaling domain or portion thereof of comprises one or more concatenated cytoplasmic signaling domains. In some embodiments, the homodimerizing domain comprises an FKBP domain or an FRB or a portion thereof configured to bind to a ligand, preferably simultaneously, such as AP1903. In some embodiments, the protein sequence further comprises a second sequence. In some embodiments, the cell, such as a mammalian cell, for homodimeric component expression comprises an expression vector comprises a nucleic acid encoding a protein sequence encoding a chemical-induced signaling complex component. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex component is positioned such that when expressed, it forms a population of homodimers in the presence of a ligand configured to bridge the homodimerizing domains. In some embodiments, the signaling domain or portion thereof of comprises one or more concatenated cytoplasmic signaling domains. In some embodiments, the homodimerizing domain comprises an FKBP domain or an FRB or a portion thereof configured to bind to a ligand, preferably simultaneously, such as AP1903. In some embodiments, the expression vector encodes a promoter. In some embodiments, the promoter is an inducible promoter or a constitutive promoter. In some embodiments, the vector is RNA or DNA. In some embodiments, the vector is a lentiviral vector or an adeno-associated viral (AAV) vector. In some embodiments, after providing the cell, such as a mammalian cell, the method further comprises expressing a protein sequence encoding a homodimeric CISC as provided herein or expressing the expression vector encoding a nucleic acid for homodimeric CISC expression as provided herein, and contacting the cell with a dimerizing agent, thereby causing the first and second CISC to dimerize, which transduces a signal into the interior of the cell.

In some embodiments, the dimerizing agent used is a ligand, such as rapamycin or a rapalog, such as everolimus, CCI-779, C20-methallylrapamycin, C16-(S) methylindolerapamycin, C16-iRap, AP21967, sodium mycophenolic acid, benidipine hydrochloride, AP23573, or AP1903, or metabolites, derivatives, and/or combinations thereof. In some embodiments, the ligand is an IMID-class drug (e.g. thalidomide, pomalidomide, lenalidomide or related analogues). In some embodiments, the transduction of the signal affects cytokine signaling. In some embodiments, the transduction of the signal affects interleukin-2 receptor (IL2R) signaling. In some embodiments, following contact with the dimerizing agent, cells expressing CISC are selectively expanded from a heterogeneous population of cells, such as mammalian cells.

Some embodiments provided herein relate to a kit or a system including the components described herein. Thus, in some embodiments is provided a kit comprising one or more of: a protein sequence as described herein; an expression vector as described herein; and/or a cell as described herein. Some embodiments include a system for selectively activating a signal into an interior of a cell, comprising: a cell as described herein, wherein the cell comprises an expression vector as described herein comprising a nucleic acid encoding a protein sequence as described herein.

BRIEF DESCRIPTION OF THE DRAWINGS

FIG. 4B shows Western blots for the respective IL2R-CISC, comprising 1210, 1211, and 1233. Arrows indicate the detection of CISC component expression. Importantly, the 1233 architecture appears to express at the highest level.

FIG. 12 shows that only the cells expressing the IL2R-CISC V3 exhibited significant rapamycin-induced expansion over the course of the 25 days of the experiment.

FIG. 13 shows that cells expressing the IL2R-CISC V3 exhibited significant rapamycin-induced expansion over the course of the experiment, and that 1 nM rapamycin induced the most robust cell expansion.

FIG. 16 demonstrates that cells expressing the IL2R-CISC V3 exhibited significant AP21967-induced expansion over the course of the experiment, and that 100 nM AP21967 induced the most robust cell expansion.

DETAILED DESCRIPTION

Figure 1:
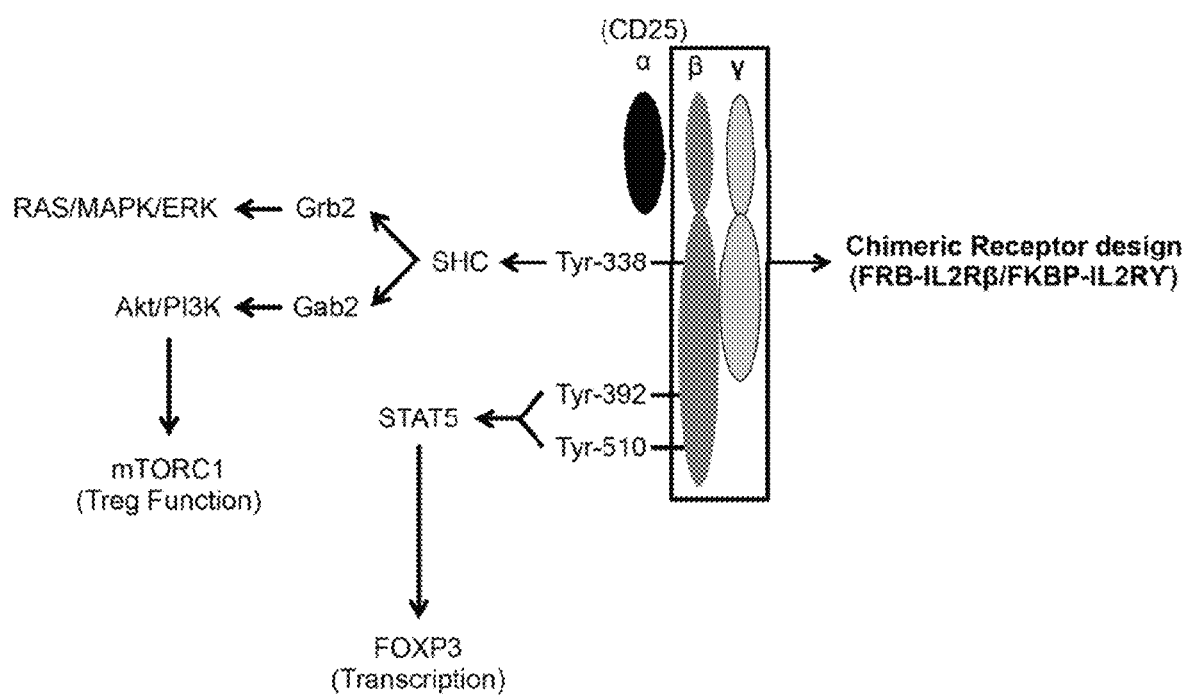
FIG. 1 is a schematic diagram illustrating IL-2 signaling in T-cell expansion. The diagram depicts chimeric dimerization of IL-2 chains comprising FRB-CD25β (transmembrane (TM) and cytoplasmic domains) (IL2Rβ) and FKBP-CD25γ (TM and cytoplasmic domains) (IL2Rγ), resulting in downstream signaling pathways. Importantly, removal of most or all of the extracellular domains prevents binding of IL2 to these chemical-induced signaling complex components, thus they are not responsive to endogenous IL2.

Described herein are compositions of chemical-induced signaling complex (CISC), and methods of making and using the same. The CISC can be used for activating a signal through a signaling pathway in a cell and for the selective expansion of cells.

Definitions

Unless defined otherwise, all technical and scientific terms used herein have the same meaning as commonly understood by one of ordinary skill in the art to which the disclosure pertains. All patents, applications, published applications and other publications referenced herein are expressly incorporated by reference in their entireties unless stated otherwise. In the event that there are a plurality of definitions for a term herein, those in this section prevail unless stated otherwise.

As used herein, "a" or "an" may mean one or more than one.

"About" has its plain and ordinary meaning when read in light of the specification, and may be used, for example, when referring to a measurable value and may be meant to encompass variations of ±20% or ±10%, more preferably ±5%, even more preferably ±1%, and still more preferably ±0.1% from the specified value.

As used herein, "protein sequence" refers to a polypeptide sequence of amino acids that is the primary structure of a protein. As used herein "upstream" refers to positions 5' of a location on a polynucleotide, and positions toward the N-terminus of a location on a polypeptide. As used herein "downstream" refers to positions 3' of a location on a nucleotide, and positions toward the C-terminus of a location on a polypeptide. Thus, the term "N-terminal" refers to the position of an element or location on a polynucleotide toward the N-terminus of a location on a polypeptide.

"Nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also comprises so-called "peptide nucleic acids," which comprise naturally-occurring or modified nucleic acid bases attached to a polyamide backbone. Nucleic acids can be either single stranded or double stranded. In some embodiments, a nucleic acid sequence encoding a fusion protein is provided. In some embodiments, the nucleic acid is RNA or DNA.

"Coding for" or "encoding" are used herein, and refers to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system.

A "nucleic acid sequence coding for a polypeptide" comprises all nucleotide sequences that are degenerate versions of each other and that code for the same amino acid sequence. In some embodiments, a nucleic acid is provided, wherein the nucleic acid encodes a fusion protein.

"Vector," "expression vector," or "construct" is a nucleic acid used to introduce heterologous nucleic acids into a cell that has regulatory elements to provide expression of the heterologous nucleic acids in the cell. Vectors include but are not limited to plasmid, minicircles, yeast, and viral genomes. In some embodiments, the vectors are plasmid, minicircles, yeast, or viral genomes. In some embodiments, the vector is a viral vector. In some embodiments, the viral vector is a lentivirus. In some embodiments, the vector is an adeno-associated viral (AAV) vector. In some embodiments, the vector is for protein expression in a bacterial system such as E. coli. As used herein, the term "expression," or "protein expression" refers to refers to the translation of a transcribed RNA molecule into a protein molecule. Protein expression may be characterized by its temporal, spatial, developmental, or morphological qualities as well as by quantitative or qualitative indications. In some embodiments, the protein or proteins are expressed such that the proteins are positioned for dimerization in the presence of a ligand.

As used herein, "fusion proteins" or "chimeric proteins" are proteins created through the joining of two or more genes that originally coded for separate proteins or portions of proteins. The fusion proteins can also be made up of specific protein domains from two or more separate proteins. Translation of this fusion gene can result in a single or multiple polypeptides with functional properties derived from each of the original proteins. Recombinant fusion proteins can be created artificially by recombinant DNA technology for use in biological research or therapeutics. Such methods for creating fusion proteins are known to those skilled in the art. Some fusion proteins combine whole peptides and therefore can contain all domains, especially functional domains, of the original proteins. However, other fusion proteins, especially those that are non-naturally occurring, combine only portions of coding sequences and therefore do not maintain the original functions of the parental genes that formed them. In some embodiments, a fusion protein is provided, wherein the fusion protein comprises an interferon and a PD-1 protein.

As used herein, the term "regulatory element" refers to a DNA molecule having gene regulatory activity, e.g., one that has the ability to affect the transcription and/or translation of an operably linked transcribable DNA molecule. Regulatory elements such as promoters, leaders, introns, and transcription termination regions are DNA molecules that have gene regulatory activity and play an integral part in the overall expression of genes in living cells. Isolated regulatory elements, such as promoters, that function in plants are therefore useful for modifying plant phenotypes through the methods of genetic engineering.

As used herein, the term "operably linked" refers to a first molecule joined to a second molecule, wherein the molecules are so arranged that the first molecule affects the function of the second molecule. The two molecules may be part of a single contiguous molecule and may be adjacent. For example, a promoter is operably linked to a transcribable DNA molecule if the promoter modulates transcription of the transcribable DNA molecule of interest in a cell.

A "promoter" is a region of DNA that initiates transcription of a specific gene. The promoters can be located near the transcription start site of a gene, on the same strand and upstream on the DNA (the 5'region of the sense strand). The promoter can be a conditional, inducible or a constitutive promoter. The promoter can be specific for bacterial, mammalian or insect cell protein expression. In some embodiments, wherein a nucleic acid encoding a fusion protein is provided, the nucleic acid further comprises a promoter sequence. In some embodiments, the promoter is specific for bacterial, mammalian or insect cell protein expression. In some embodiments, the promoter is a conditional, inducible or a constitutive promoter "Conditional" or "inducible" as used herein refers to a nucleic acid construct that comprises a promoter that provides for gene expression in the presence of an inducer and does not substantially provide for gene expression in the absence of the inducer.

"Constitutive" as used herein refer to the nucleic acid construct that comprises a promoter that is constitutive, and thus provides for expression of a polypeptide that is continuously produced.

In some embodiments, the inducible promoter has a low level of basal activity. In some embodiments, wherein a lentiviral vector is used, the level of basal activity in uninduced cells is 20%, 15%, 10%, 5%, 4%, 3%, 2%, 1% or less (but not zero) or within a range defined by any two of the aforementioned values, as compared to when cells are induced to express the gene. The level of basal activity can be determined by measuring the amount of the expression of the transgene (e.g. marker gene) in the absence of the inducer (e.g. drug) using flow cytometry. In some embodiments described herein a marker protein such as Akt is used for determination of expression.

In some embodiments, the inducible promoter provides for a high level of induced activity, as compared to uninduced or basal activity. In some embodiments, the level of activity in the induced state is 2, 4, 6, 8, 9 or 10 fold or greater than the activity level in the uninduced state or within a range defined by any two of the aforementioned values. In some embodiments, transgene expression under control of the inducible promoter is turned off in the absence of a transactivator in less than 10, 8, 6, 4, 2, or 1 days excluding 0 days or within a range defined by any two of the aforementioned time periods.

In some embodiments, an inducible promoter is designed and/or modified to provide for a low level of basal activity, a high level of inducibility, and/or a short time for reversibility.

"Dimeric chemical-induced signaling complex," "dimeric CISC," or "dimer" as used herein refers to two components of a CISC, which may or may not be fusion protein complexes that join together. "Dimerization" refers to the process of the joining together of two separate entities into a single entity. In some embodiments, a ligand or agent stimulates dimerization. In some embodiments, dimerization refers to homodimerization, or the joining of two identical entities, such as two identical CISC components. In some embodiments, dimerization refers to heterodimerization, of the joining of two different entities, such as two different and distinct CISC components. In some embodiments, the dimerization of the CISC components results in a cellular signaling pathway. In some embodiments, the dimerization of the CISC components allows for the selective expansion of a cell or a population of cells. Additional CISC systems can include a CISC gibberellin CISC dimerization system, or a SLF-TMP CISC dimerization system. Other chemically inducible dimerization (CID) systems and component parts may be used.

As used herein, "chemical-induced signaling complex" or "CISC" refers to an engineered complex that initiates a signal into the interior of a cell as a direct outcome of ligand-induced dimerization. A CISC may be a homodimer (dimerization of two identical components) or a heterodimer (dimerization of two distinct components). Thus, as used herein the term "homodimer" refers to a dimer of two protein components described herein with identical amino acid sequences. The term "heterodimer" refers to a dimer of two protein components described herein with non-identical amino acid sequences.

The CISC may be a synthetic complex as described herein in greater detail. "Synthetic" as used herein refers to a complex, protein, dimer, or composition, as described herein, which is not natural, or that is not found in nature. In some embodiments, an IL2R-CISC refers to a signaling complex that involves interleukin-2 receptor components. In some embodiments, an IL2/15-CISC refers to a signaling complex that involves receptor signaling subunits that are shared by interleukin-2 and interleukin-15. In some embodiments, an IL7-CISC refers to a signaling complex that involves an interleukin-7 receptor components. A CISC may thus be termed according to the component parts that make up the components of a given CISC. One of skill in the art will recognize that the component parts of the chemical-induced signaling complex may be composed of a natural or a synthetic component useful for incorporation into a CISC. Thus, the examples provided herein are not intended to be limiting.

As used herein, "cytokine receptor" refers to receptor molecules that recognize and bind to cytokines. In some embodiments, cytokine receptor encompasses modified cytokine receptor molecules (e.g., "variant cytokine receptors"), comprising those with substitutions, deletions, and/or additions to the cytokine receptor amino acid and/or nucleic acid sequence. Thus, it is intended that the term encompass wild-type, as well as, recombinant, synthetically-produced, and variant cytokine receptors. In some embodiments, the cytokine receptor is a fusion protein, comprising an extracellular binding domain, a hinge domain, a transmembrane domain, and a signaling domain. In some embodiments, the components of the receptor (that is, the domains of the receptor) are natural or synthetic. In some embodiments, the domains are human derived domains.

"FKBP" as used herein, is a FK506 binding protein domain. FKBP refers to a family of proteins that have prolyl isomerase activity and are related to the cyclophilins in function, though not in amino acid sequence. FKBPs have been identified in many eukaryotes from yeast to humans and function as protein folding chaperones for proteins containing proline residues. Along with cyclophilin, FKBPs belong to the immunophilin family. The term FKBP comprises, for example, FKBP12 as well as, proteins encoded by the genes AIP; AIPL1; FKBP1A; FKBP1B; FKBP2; FKBP3; FKBP5; FKBP6; FKBP7; FKBP8; FKBP9; FKBP9L; FKBP10; FKBP11; FKBP14; FKBP15; FKBP52; and/or LOC541473; comprising homologs thereof and functional protein fragments thereof.

"FRB" as used herein, as a FKBP rapamycin binding domain. FRB domains are polypeptide regions (protein "domains") that are configured to form a tripartite complex with an FKBP protein and rapamycin or rapalog thereof. FRB domains are present in a number of naturally occurring proteins, comprising mTOR proteins (also referred to in the literature as FRAP, RAPT 1, or RAFT) from human and other species; yeast proteins comprising Tor1 and/or Tor2; and a *Candida* FRAP homolog. Both FKBP and FRB are major constituents in the mammalian target of rapamycin (mTOR) signaling.

Cereblon interacts with damaged DNA binding protein 1 and forms an E3 ubiquitin ligase complex with Cullin 4 where it functions as a substrate receptor in which the proteins recognized by cereblon may be ubiquitinated and degraded by proteasomes. Proteasome-mediated degradation of unneeded or damaged proteins plays a very important role in maintaining regular function of a cell, such as cell survival, proliferation and/or growth. The binding of immunomodulatory imide drugs (IMIDs), e.g. thalidomide, to cereblon has been associated with teratogenicity and also the cytotoxicity of IMIDs, including lenalidomide. Cereblon is a key player in the binding, ubiquitination, and degradation of factors involved in maintaining function of myeloma cells.

"Cereblon thalidomide binding domain" refers to a binding domain that is an extracellular binding domain that interacts with an IMID, comprising, for example, thalidomide, pomalidomide, lenalidomide, apremilast, or related analogues. Some embodiments provided herein utilize cereblon thalidomide binding domain analogues or mutants thereof. In some embodiments, these extracellular binding domains are configured to simultaneously bind to an IMID ligand.

In some embodiments, the immunomodulatory imide drug used in the approaches described herein may comprise:

thalidomide (including analogues, derivatives, and including pharmaceutically acceptable salts thereof. Thalidomide may include Immunoprin, Thalomid, Talidex, Talizer, Neurosedyn, α-(N-Phthalimido)glutarimide, 2-(2,6-dioxopiperidin-3-yl)-2,3-dihydro-1H-isoindole-1,3-dione);

pomalidomide (including analogues, derivatives, and including pharmaceutically acceptable salts thereof. Pomalidomide may include Pomalyst, Imnovid, (RS)-4-Amino-2-(2,6-dioxopiperidin-3-yl)isoindole-1,3-dione);

lenalidomide (including analogues, derivatives, and including pharmaceutically acceptable salts thereof. Lenalidomide may include Revlimid, (RS)-3-(4-Amino-1-oxo-1,3-dihydro-2H-isoindol-2-yl)piperidine-2,6-dione); or apremilast (including analogues, derivatives, and including pharmaceutically acceptable salts thereof. Apremilast may include Otezla, CC-10004, N-{2-[(1S)-1-(3-Ethoxy-4-methoxyphenyl)-2-(methylsulfonyl)ethyl]-1,3-dioxo-2,3-dihydro-1H-isoindol-4-yl}acetamide);

or any combinations thereof.

As used herein, the term "extracellular binding domain" refers to a domain of a complex that is outside of the cell, and which is configured to bind to a specific atom or molecule. In some embodiments, the extracellular binding domain of a CISC is a FKBP domain or a portion thereof. In some embodiments, the extracellular binding domain is an FRB domain or a portion thereof. In some embodiments, the extracellular binding domain is configured to bind a ligand or agent, thereby stimulating dimerization of two CISC components. In some embodiments, the extracellular binding domain is configured to bind to a cytokine receptor modulator.

As used herein, the term "cytokine receptor modulator" refers to an agent, which modulates the phosphorylation of a downstream target of a cytokine receptor, the activation of a signal transduction pathway associated with a cytokine receptor, and/or the expression of a particular protein such as a cytokine. Such an agent may directly or indirectly modulate the phosphorylation of a downstream target of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins and/or antibodies or binding portions thereof that immunospecifically bind to a cytokine receptor or a fragment thereof. Further, examples of cytokine receptor modulators include, but are not limited to, peptides, polypeptides (e.g., soluble cytokine receptors), fusion proteins and/or antibodies or binding portions thereof that immunospecifically bind to a cytokine or a fragment thereof.

As used herein, the term "activate" refers to an increase in at least one biological activity of a protein of interest. Similarly, the term "activation" refers to a state of a protein of interest being in a state of increased activity. The term "activatable" refers to the ability of a protein of interest to become activated in the presence of a signal, an agent, a ligand, a compound, or a stimulus. In some embodiments, a dimer, as described herein, is activated in the presence of a signal, an agent, a ligand, a compound, or a stimulus, and becomes a signaling competent dimer. As used herein, the term "signaling competent" refers to the ability or configuration of the dimer so as to be capable of initiating or sustaining a downstream signaling pathway.

As used herein, the term "hinge domain" refers to a domain that links the extracellular binding domain to the transmembrane domain, and may confer flexibility to the extracellular binding domain. In some embodiments, the hinge domain positions the extracellular domain close to the plasma membrane to minimize the potential for recognition by antibodies or binding fragments thereof. In some embodiments, the extracellular binding domain is located N-terminal to the hinge domain. In some embodiments, the hinge domain may be natural or synthetic.

As used herein, the term "transmembrane domain" or "TM domain" refers to a domain that is stable in a membrane, such as in a cell membrane. The terms "transmembrane span," "integral protein," and "integral domain" are also used herein. In some embodiments, the hinge domain and the extracellular domain is located N-terminal to the transmembrane domain. In some embodiments, the transmembrane domain is a natural or a synthetic domain. In some embodiments, the transmembrane domain is an IL-2 transmembrane domain.

As used herein, the term "signaling domain" refers to a domain of the fusion protein or CISC component that is involved in a signaling cascade inside the cell, such as a mammalian cell. A signaling domain refers to a signaling moiety that provides to cells, such as T-cells, a signal which, in addition to the primary signal provided by for instance the CD3 zeta chain of the TCR/CD3 complex, mediates a cellular response, such as a T-cell response, comprising, but not limited to, activation, proliferation, differentiation, and/or cytokine secretion. In some embodiments, the signaling domain is N-terminal to the transmembrane domain, the hinge domain, and the extracellular domain. In some embodiments, the signaling domain is a synthetic or a natural domain. In some embodiments, the signaling domain is a concatenated cytoplasmic signaling domain. In some embodiments, the signaling domain is a cytokine signaling domain. In some embodiments, the signaling domain is an antigen signaling domain. In some embodiments, the signaling domain is an interleukin-2 receptor subunit gamma (IL2Rγ or IL2Rg) domain. In some embodiments, the signaling domain is an interleukin-2 receptor subunit beta (IL2Rβ or IL2Rb) domain. In some embodiments, binding of an agent or ligand to the extracellular binding domain causes a signal transduction through the signaling domain by the activation of a signaling pathway, as a result of dimerization of the CISC components. As used herein, the term "signal transduction" refers to the activation of a signaling pathway by a ligand or an agent binding to the extracellular domain. Activation of a signal is a result of the binding of the extracellular domain to the ligand or agent, resulting in CISC dimerization.

As used herein, the term "IL2Rb" or "IL2Rβ" refers to an interleukin-2 receptor subunit beta. Similarly, the term "IL2Rg" or "IL2Rγ" refers to an interleukin-2 receptor subunit gamma, and the term "IL2Ra" or "IL2Rα" refers to an interleukin-2 receptor subunit alpha. The IL-2 receptor has three forms, or chains, alpha, beta, and gamma, which are also subunits for receptors for other cytokines. IL2Rβ and IL2Rγ are members of the type I cytokine receptor family. "IL2R" as used herein refers to interleukin-2 receptor, which is involved in T cell-mediated immune responses. IL2R is involved in receptor-mediated endocytosis and transduction of mitogenic signals from interleukin 2. Similarly, the term "IL-2/15R" refers to a receptor signaling subunit that is shared by IL-2 and IL-15, and may include a subunit alpha (IL2/15Ra or IL2/15Rα), beta (IL2/15Rb or IL2/15R β, or gamma (IL2/15Rg or IL2/15Rγ).

In some embodiments, a chemical-induced signaling complex is a heterodimerization activated signaling complex comprising two components. In some embodiments, the first component comprises an extracellular binding domain that is one part of a heterodimerization pair, an optional hinge domain, a transmembrane domain, and one or more concatenated cytoplasmic signaling domains. In some embodiments, the second component comprises an extracellular binding domain that is the other part of a heterodimerization pair, an optional hinge domain, a transmembrane domain, and one or more concatenated cytoplasmic signaling domains. Thus, in some embodiments, there are two distinct modification events. In some embodiments, the two CISC components are expressed in a cell, such as a mammalian cell. In some embodiments, the cell, such as a mammalian cell, or a population of cells, such as a population of mammalian cells, is contacted with a ligand or agent that causes heterodimerization, thereby initiating a signal. In some embodiments, a homodimerization pair dimerize, whereby a single CISC component is expressed in a cell, such as a mammalian cell, and the CISC components homodimerize to initiate a signal.

As used herein, the term "ligand" or "agent" refers to a molecule that has a desired biological effect. In some embodiments, a ligand is recognized by and bound by an extracellular binding domain, forming a tripartite complex comprising the ligand and two binding CISC components. Ligands include, but are not limited to, proteinaceous molecules, comprising, but not limited to, peptides, polypeptides, proteins, post-translationally modified proteins, antibodies, binding portions thereof; small molecules (less than 1000 Daltons), inorganic or organic compounds; and nucleic acid molecules comprising, but not limited to, double-stranded or single-stranded DNA, or double-stranded or single-stranded RNA (e.g., antisense, RNAi, etc.), aptamers, as well as, triple helix nucleic acid molecules. Ligands can be derived or obtained from any known organism (comprising, but not limited to, animals (e.g., mammals (human and non-human mammals)), plants, bacteria, fungi, and protista, or viruses) or from a library of synthetic molecules. In some embodiments, the ligand is a protein, an antibody or portion thereof, a small molecule, or a drug. In some embodiments, the ligand is rapamycin or a rapamycin analog (rapalogs). In some embodiments, the rapalog comprises variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Thus, in some embodiments, the rapalog is everolimus, merilimus, novolimus, pimecrolimus, ridaforolimus, tacrolimus, temsirolimus, umirolimus, zotarolimus, CCI-779, C20-methallylrapamycin, C16-(S)-3-methylindolerapamycin, C16-iRap, AP21967, sodium mycophenolic acid, benidipine hydrochloride, AP23573, or AP1903, or metabolites, derivatives, and/or combinations thereof. In some embodiments, the ligand is an IMID-class drug (e.g. thalidomide, pomalidomide, lenalidomide or related analogues).

Accordingly, in some embodiments, the ligand or agent used in the approaches described herein for chemical induction of the signaling complex may comprise:

rapamycin (including analogues, derivatives, and including pharmaceutically acceptable salts thereof. Rapamycin may include Sirolimus, Rapamune, (3S,6R,7E,9R,10R,12R, 14S,15E,17E,19E,21S,23S,26R,27R,34aS)-9,10,12,13,14, 21,22,23,24,25,26,27,32,33,34,34α-hexadecahydro-9,27-dihydroxy-3-[(1R)-2-[(1S,3R,4R)-4-hydroxy-3-methoxycyclohexyl]-1-methylethyl]-10,21-dimethoxy-6,8, 12,14,20,26-hexamethyl-23,27-epoxy-3H-pyrido[2,1-c][1, 4]oxaazacyclohentriacontine-1,5,11,28,29 (4H,6H,31H)-pentone);

everolimus (including analogues, derivatives, and including pharmaceutically acceptable salts thereof. Everolimus may include RAD001, Zortress, Certican, Afinitor, Votubia, 42-O-(2-hydroxyethyl)rapamycin, (1R,9S,12S,15R,16E, 18R,19R,21R,23S,24E,26E,28E,30S,32S,35R)-1,18-dihydroxy-12-[(2R)-1-[(1S,3R,4R)-4-(2-hydroxyethoxy)-3-methoxycyclohexyl]propan-2-yl]-19,30-dimethoxy-15,17, 21,23,29,35-hexamethyl-11,36-dioxa-4-azatricyclo [30.3.1.0$^{4,9}$]hexatriaconta-16,24,26,28-tetraene-2,3,10,14, 20-pentone);

merilimus (including analogues, derivatives, and including pharmaceutically acceptable salts thereof. Merilimus may include SAR943, 42-O-(tetrahydrofuran-3-yl)rapamycin (Merilimus-1); 42-O-(oxetan-3-yl)rapamycin (Merilimus-2), 42-O-(tetrahydropyran-3-yl)rapamycin (Merilimus-3), 42-O-(4-methyl, tetrahydrofuran-3-yl)rapamycin, 42-O-(2,5,5-trimethyl, tetrahydrofuran-3-yl) rapamycin, 42-O-(2, 5-diethyl-2-methyl, tetrahydrofuran-3-yl)rapamycin, 42-O-(2H-Pyran-3-yl, tetrahydro-6-methoxy-2-methyl) rapamycin, or 42-O-(2H-Pyran-3-yl, tetrahydro-2,2-dimethyl-6-phenyl)rapamycin);

novolimus (including analogues, derivatives, and including pharmaceutically acceptable salts thereof. Novolimus may include 16-O-Demethyl Rapamycin);

pimecrolimus (including analogues, derivatives, and including pharmaceutically acceptable salts thereof. Pimecrolimus may include Elidel, (3S,4R,5S,8R,9E,12S,14S, 15R,16S,18R,19R,26aS)-3-((E)-2-((1R,3R,4S)-4-chloro-3 methoxycyclohexyl)-1-methylvinyl)-8-ethyl 5,6,8,11,12,13, 14,15,16,17,18,19,24,26,26ahexadecahydro-5,19-epoxy-3H-pyrido(2,1-c)(1,4)oxaazacyclotricosine-1,17,20,21(4H, 23H)-tetrone 33-epi-Chloro desoxyascomycin);

ridaforolimus (including analogues, derivatives, and including pharmaceutically acceptable salts thereof. Ridaforolimus may include AP23573, MK-8669, deforolimus, (1R,9S,12S,15R,16E,18R,19R,21R,23S,24E,26E,28E, 30S,32S,35R)-12-((1R)-24(1S,3R,4R)-4-((Dimethylphosphinoyl)oxy)-3-methoxycyclohexyl)-1-methylethyl)-1,18-dihydroxy-19,30-dimethoxyl5,17,21,23,29,35-hexamethyl-11,36-dioxa-4-azatricyclo(30.3.1.04,9)hexatriaconta-16,24, 26,28-tetraene-2,3,10,14,20-pentone);

tacrolimus (including analogues, derivatives, and including pharmaceutically acceptable salts thereof. Tacrolimus may include FK-506, fujimycin, Prograf, Advagraf, protopic, 3S-[3R*[E(1S*,3S*,4S*)],4S*,5R*,8S*,9E,12R*, 14R*,15S*,16R*,18S*,19S*,26aR*5,6,8,11,12,13,14,15, 16,17,18,19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4] oxaazacyclotricosine-1, 7,20,21(4H,23H)-tetrone, monohydrate);

temsirolimus (including analogues, derivatives, and including pharmaceutically acceptable salts thereof. Temsirolimus may include CCI-779, CCL-779, Torisel, (1R,2R, 4S)-4-{(2R)-2-[(3S,6R,7E,9R,10R,12R,14S,15E,17E,19E, 21S,23S,26R,27R,34aS)-9,27-dihydroxy-10,21-dimethoxy-6,8,12,14,20,26-hexamethyl-1,5,11,28,29-pentaoxo-1,4,5,6, 9,10,11,12,13,14,21,22,23,24,25,26,27,28,29,31,32,33,34, 34a-tetracosahydro-3H-23,27-epoxypyrido[2,1-c][1,4] oxazacyclohentriacontin-3-yl]propyl}-2-methoxycyclohexyl 3-hydroxy-2-(hydroxymethyl)-2-methylpropanoate);

umirolimus (including analogues, derivatives, and including pharmaceutically acceptable salts thereof. Umirolimus may include Biolimus, Biolimus A9, BA9, TRM-986, 42-O-(2-ethoxyethyl)Rapamycin);

zotarolimus (including analogues, derivatives, and including pharmaceutically acceptable salts thereof. Zotarolimus may include ABT-578, (42S) Deoxy-42-(1H-tetrazol-1-yl)-rapamycin);

C20-methallylrapamycin (including analogues, derivatives, and including pharmaceutically acceptable salts thereof. C20-methallylrapamycin may include C20-Marap);

C16-(S)-3-methylindolerapamycin (including analogues, derivatives, and including pharmaceutically acceptable salts thereof. C16-(S)-3-methylindolerapamycin may include C16-iRap);

AP21967 (including analogues, derivatives, and including pharmaceutically acceptable salts thereof. AP21967 may include C-16-(S)-7-methylindolerapamycin);

sodium mycophenolic acid (including analogues, derivatives, and including pharmaceutically acceptable salts thereof. Sodium mycophenolic acid may include CellCept, Myfortic, (4E)-6-(4-Hydroxy-6-methoxy-7-methyl-3-oxo-1,3-dihydro-2-benzofuran-5-yl)-4-methylhex-4-enoic acid);

benidipine hydrochloride (including analogues, derivatives, and including pharmaceutically acceptable salts thereof. Benidipine hydrochloride may include Benidipinum, Coniel); or AP1903 (including analogues, derivatives, and including pharmaceutically acceptable salts thereof. AP1903 may include Rimiducid, [(1R)-3-(3,4-dimethoxyphenyl)-1-[3-[2-[2-[[2-[3-[(1R)-3-(3,4-dimethoxyphenyl)-1-[(2S)-1-[(2S)-2-(3,4,5-trimethoxyphenyl)butanoyl]piperidine-2-carbonyl] oxypropyl]phenoxy]acetyl]amino]ethylamino]-2-oxoethoxy]phenyl]propyl] (2S)-1-[(2S)-2-(3,4,5-trimethoxyphenyl)butanoyl]piperidine-2-carboxylate);

or any combinations thereof.

As used herein, the term "gibberellin" refers to a synthetic or naturally occurring form of the diterpenoid acids that are synthesized by the terpenoid pathway in plastids and then modified in the endoplasmic reticulum and cytosol until they reach their biologically-active form. Gibberellin may be a natural gibberellin or an analogue thereof, including, for example, gibberellins derived from the ent-gibberellane skeleton, or synthesized via ent-kauren, including gibberelling 1 (GA1), GA2, GA3 . . . GA136, and analogues and derivatives thereof. In some embodiments, gibberellin or an analogue or derivative thereof is utilized for CISC dimerization.

As used herein, "SLF-TMP" or "synthetic ligand of FKBP linked to trimethoprim" refers to a dimerizer for CISC dimerization. In some embodiments, the SLF moiety binds to a first CISC component and the TMP moiety binds to a second CISC component, causing CISC dimerization. In some embodiments, SLF can bind, for example, to FKBP and TMP can bind to E. coli dihydrofolate reductase (eDHFR).

As used herein, the term "simultaneous binding" refers to the binding of the ligand by two or more CISC components at the same time or, in some cases, at substantially the same time, to form a multicomponent complex, comprising the CISC components and the ligand component, and resulting in subsequent signal activation. Simultaneous binding requires that the CISC components are configured spatially to bind a single ligand, and also that both CISC components are configured to bind to the same ligand, including to different moieties on the same ligand.

As used herein, the term "selective expansion" refers to an ability of a desired cell, such as a mammalian cell, or a desired population of cells, such as a population of mammalian cells, to expand. In some embodiments, selective expansion refers to the generation or expansion of a pure population of cells, such as mammalian cells, that have undergone two genetic modification events. One component of a dimerization CISC is part of one modification and the other component is the other modification. Thus, one component of the heterodimerizing CISC is associated with each genetic modification. Exposure of the cells to a ligand allows for selective expansion of only the cells, such as mammalian cells, having both desired modifications. Thus, in some embodiments, the only cells, such as mammalian cells, that will be able to respond to contact with a ligand are those that express both components of the heterodimerization CISC.

As used herein, "host cell" comprises any cell type, such as a mammalian cell, that is susceptible to transformation, transfection, or transduction, with a nucleic acid construct or vector. In some embodiments, the host cell, such as a mammalian cell, is a T cell or a T regulatory cell (Treg). In some embodiments, the host cell, such as a mammalian cell, is a hematopoietic stem cell. In some embodiments, the host cell is a CD34+, CD8+, or a CD4+ cell. In some embodiments, the host cell is a CD8+T cytotoxic lymphocyte cell selected from the group consisting of naïve CD8+ T cells, central memory CD8+ T cells, effector memory CD8+ T cells, and bulk CD8+ T cells. In some embodiments, the host cell is a CD4+T helper lymphocyte cell selected from the group consisting of naïve CD4+ T cells, central memory CD4+ T cells, effector memory CD4+ T cells, and bulk CD4+ T cells. As used herein, the term "population of cells" refers to a group of cells, such as mammalian cells, comprising more than one cell. In some embodiments, a cell, such as a mammalian cell, is manufactured, wherein the cell comprises the protein sequence as described herein or an expression vector that encodes the protein sequence as described herein.

As used herein, the term "transformed" or "transfected" refers to a cell, such as a mammalian cell, tissue, organ, or organism into which a foreign polynucleotide molecule, such as a construct, has been introduced. The introduced polynucleotide molecule may be integrated into the genomic DNA of the recipient cell, such as a mammalian cell, tissue, organ, or organism such that the introduced polynucleotide molecule is inherited by subsequent progeny. A "transgenic" or "transfected" cell, such as a mammalian cell, or organism also comprises progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules. "Transduction" refers to virus-mediated gene transfer into cells, such as mammalian cells.

As used herein, a "subject" refers to an animal that is the object of treatment, observation or experiment. "Animal" comprises cold- and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternative, the subject is human.

In some embodiments, an effective amount of a ligand used for inducing dimerization is an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

A "marker sequence," as described herein, encodes a protein that is used for selecting or tracking a protein or cell, such as a mammalian cell, that has a protein of interest. In the embodiments described herein, the fusion protein provided can comprise a marker sequence that can be selected in experiments, such as flow cytometry.

"Chimeric receptor" or "chimeric antigen receptor," as used herein refers to a synthetically designed receptor comprising a ligand binding domain of an antibody or other protein sequence that binds to a molecule associated with the disease or disorder and is linked via a spacer domain to one or more intracellular signaling domains of a T-cell or other receptors, such as a costimulatory domain. In some embodiments, a cell, such as a mammalian cell, is manufactured wherein the cell comprises a nucleic acid encoding a fusion protein and wherein the cell comprises a chimeric antigen receptor.

"Cytotoxic T lymphocyte" (CTL), as used herein, refers to a T lymphocyte that expresses CD8 on the surface thereof (e.g., a $CD8^+$ T-cell). In some embodiments, such cells are preferably "memory" T-cells ($T_M$ cells) that are antigen-experienced. In some embodiments, a cell for fusion protein secretion is provided. In some embodiments, the cell is a cytotoxic T lymphocyte. "Central memory" T-cell (or "$T_{CM}$") as used herein, refers to an antigen experienced CTL that expresses CD62L, CCR-7 and/or CD45RO on the surface thereof, and does not express or has decreased expression of CD45RA, as compared to naive cells. In some embodiments, a cell for fusion protein secretion is provided. In some embodiments, the cell is a central memory T-cell ($T_{CM}$). In some embodiments, the central memory cells are positive for expression of CD62L, CCR7, CD28, CD127, CD45RO, and/or CD95, and may have decreased expression of CD54RA, as compared to naïve cells. "Effector memory" T-cell (or "$T_{EM}$") as used herein refers to an antigen experienced T-cell that does not express or has decreased expression of CD62L on the surface thereof, as compared to central memory cells, and does not express or has a decreased expression of CD45RA, as compared to naïve cell. In some embodiments, a cell for fusion protein secretion is provided. In some embodiments, the cell is an effector memory T-cell. In some embodiments, effector memory cells are negative for expression of CD62L and/or CCR7, as compared to naïve cells or central memory cells, and may have variable expression of CD28 and/or CD45RA.

"Naïve T-cells" as used herein, refers to a non-antigen experienced T lymphocyte that expresses CD62L and/or CD45RA, and does not express CD45RO−, as compared to central or effector memory cells. In some embodiments, a cell, such as a mammalian cell, for fusion protein secretion is provided. In some embodiments, the cell, such as a mammalian cell, is a naïve T-cell. In some embodiments, naïve CD8+T lymphocytes are characterized by the expression of phenotypic markers of naïve T-cells comprising CD62L, CCR7, CD28, CD127, and/or CD45RA.

"Effector" T-cells as used herein, refers to antigen experienced cytotoxic T lymphocyte cells that do not express or have decreased expression of CD62L, CCR7, and/or CD28, and are positive for granzyme B and/or perforin, as compared to central memory or naïve T-cells. In some embodiments, a cell, such as a mammalian cell, for fusion protein secretion is provided. In some embodiments, the cell, such as a mammalian cell, is an effector T-cell. In some embodiments, the cell, such as a mammalian cell, does not express or have decreased expression of CD62L, CCR7, and/or CD28, and are positive for granzyme B and/or perforin, as compared to central memory or naïve T-cells.

"Epitope" as used herein, refers to a part of an antigen or molecule that is recognized by the immune system comprising antibodies, T-cells, and/or B-cells. Epitopes usually have at least 7 amino acids and can be a linear or a conformational epitope. In some embodiments, a cell, such as a mammalian cell, expressing a fusion protein is provided, wherein the cell further comprises a chimeric antigen receptor. In some embodiments, the chimeric antigen receptor comprises a scFv that can recognize an epitope on a cancer cell. "Isolating," or "purifying" when used to describe the various polypeptides or nucleic acids disclosed herein, refers to a polypeptide or nucleic acid that has been identified and separated and/or recovered from a component of its natural environment. Preferably, the isolated polypeptide or nucleic acid is free of association with all components with which it is naturally associated. Contaminant components of its natural environment are materials that would typically interfere with diagnostic or therapeutic uses for the polypeptide or nucleic acid, and can include enzymes, hormones, and other proteinaceous or non-proteinaceous solutes. In some embodiments, a method is provided wherein the method comprises delivering the nucleic acid of anyone of the embodiments described herein or the expression vector of anyone of the embodiments described herein to a bacterial cell, mammalian cell or insect cell, growing the cell up in a culture, inducing expression of the fusion protein and purifying the fusion protein for treatment.

"Percent (%) amino acid sequence identity" with respect to the CISC sequences identified herein is defined as the percentage of amino acid residues in a candidate sequence that are identical with the amino acid residues in the reference sequence for each of the extracellular binding domain, hinge domain, transmembrane domain, and/or the signaling domain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, comprising any algorithms needed to achieve maximal alignment over the full-length of the sequences being compared. For example, % amino acid sequence identity values generated using the WU-BLAST-2 computer program (Altschul et al., Methods in Enzymology, 266:460-480 (1996)) uses several search parameters, most of which are set to the default values. Those that are not set to default values (e.g., the adjustable parameters) are set with the following values: overlap span=1, overlap fraction=0.125, word threshold (T)=11 and scoring matrix=BLOSUM62. In some embodiments of the CISC, the CISC comprises an extracellular binding domain, a hinge domain, a transmembrane domain, and a signaling domain, wherein each domain comprises a natural, synthetic, or a mutated or truncated form of the native domain. In some embodiments, a mutated or truncated form of any given domain comprises an amino acid sequence with 100%, 95%, 90%, 85% sequence identity, or a percent sequence identity that is within a range defined by any two of the aforementioned percentages to a sequence set forth in a sequence provided herein.

"CISC variant polypeptide sequence" or "CISC variant amino acid sequence" as used herein refers to a protein sequence as defined below having at least 80%, 85%, 90%, 95%, 98% or 99% amino acid sequence identity (or a percentage amino acid sequence identity within a range defined by any two of the aforementioned percentages) with the protein sequences provided herein, or a specifically derived fragment thereof, such as protein sequence for an extracellular binding domain, a hinge domain, a transmembrane domain and/or a signaling domain. Ordinarily, a CISC variant polypeptide or fragment thereof will have at least 80% amino acid sequence identity, more preferably at least 81% amino acid sequence identity, more preferably at least 82% amino acid sequence identity, more preferably at least 83% amino acid sequence identity, more preferably at least 84% amino acid sequence identity, more preferably at least 85% amino acid sequence identity, more preferably at least 86% amino acid sequence identity, more preferably at least 87% amino acid sequence identity, more preferably at least 88% amino acid sequence identity, more preferably at least 89% amino acid sequence identity, more preferably at least 90% amino acid sequence identity, more preferably at least 91% amino acid sequence identity, more preferably at least 92% amino acid sequence identity, more preferably at least 93% amino acid sequence identity, more preferably at least 94% amino acid sequence identity, more preferably at least 95% amino acid sequence identity, more preferably at least 96% amino acid sequence identity, more preferably at least 97% amino acid sequence identity, more preferably at least 98% amino acid sequence identity and yet more preferably at least 99% amino acid sequence identity with the amino acid sequence or a derived fragment thereof. Variants do not encompass the native protein sequence.

T-cells" or "T lymphocytes" as used herein can be from any mammalian, preferably primate, species, comprising monkeys, dogs, and humans. In some embodiments, the T-cells are allogeneic (from the same species but different donor) as the recipient subject; in some embodiments the T-cells are autologous (the donor and the recipient are the same); in some embodiments the T-cells arc syngeneic (the donor and the recipients are different but are identical twins).

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "comprising at least." When used in the context of a process, the term "comprising" means that the process comprises at least the recited steps, but may include additional steps. When used in the context of a compound, composition or device, the term "comprising" means that the compound, composition or device comprises at least the recited features or components, but may also include additional features or components.

Protein Sequences

Figure 2:
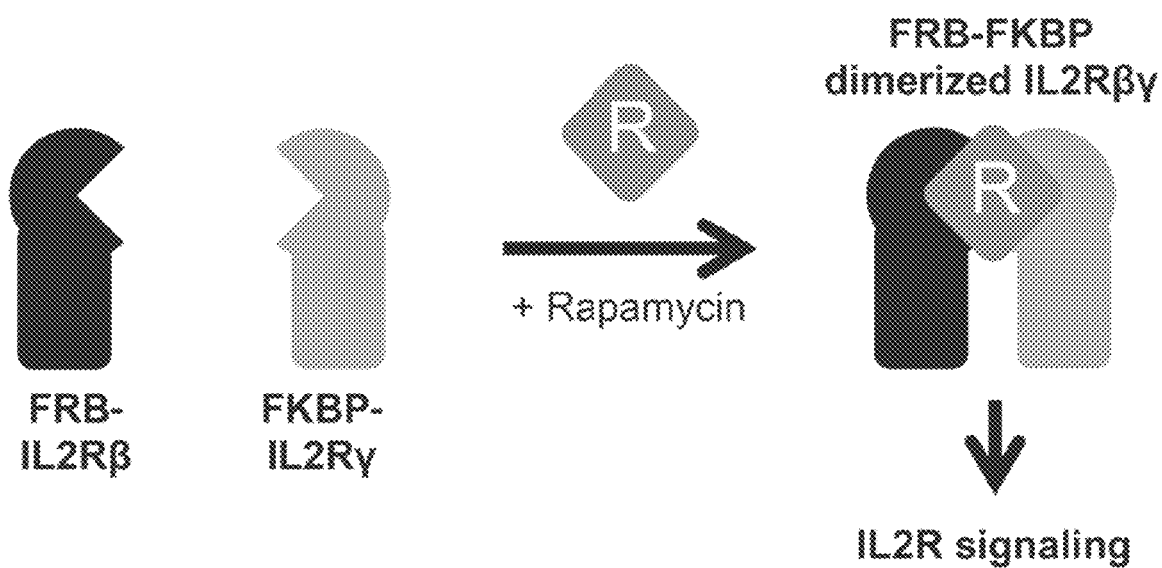
FIG. 2 schematically depicts the cell expansion strategy by a chemical-induced signaling complex (CISC). This strategy utilizes rapamycin's ability to bind two different protein motifs (FKBP and FRB) simultaneously, to induce protein dimerization and active downstream signaling events in an appropriately designed pair of CISC components. The use of a CISC in this manner allows for selective cellular expansion.

As described herein, one or more protein sequence encoding a dimeric CISC component is provided. The one or more protein sequence can have a first and a second sequence. In some embodiments, a first sequence encodes a first CISC component that can comprise a first extracellular binding domain or portion thereof, a hinge domain, a transmembrane domain, and a signaling domain or portion thereof. In some embodiments, a second sequence encodes a second CISC component that can comprise a second extracellular binding domain or a portion thereof, a hinge domain, a transmembrane domain, and a signaling domain or portions thereof. In some embodiments, the first and second CISC components may be positioned such that when expressed, they dimerize in the presence of a ligand, preferably simultaneously. Embodiments of the chemical induced signaling complex are schematically depicted in FIGS. 1-2, which also depict downstream signaling pathways as a result of activation of the CISC, which may include, for example, the RAS/MAPK/ERK signaling pathway, Akt/PI3K signaling pathway, the mTORC1 signaling pathway, or the FOXP3 signaling pathway. In addition, FIG. 2 schematically depicts IL2R signaling due to FRB-FKBP dimerized IL2Rbg in the presence of a ligand, such as rapamycin or an analogue thereof, as described herein.

Figure 3:
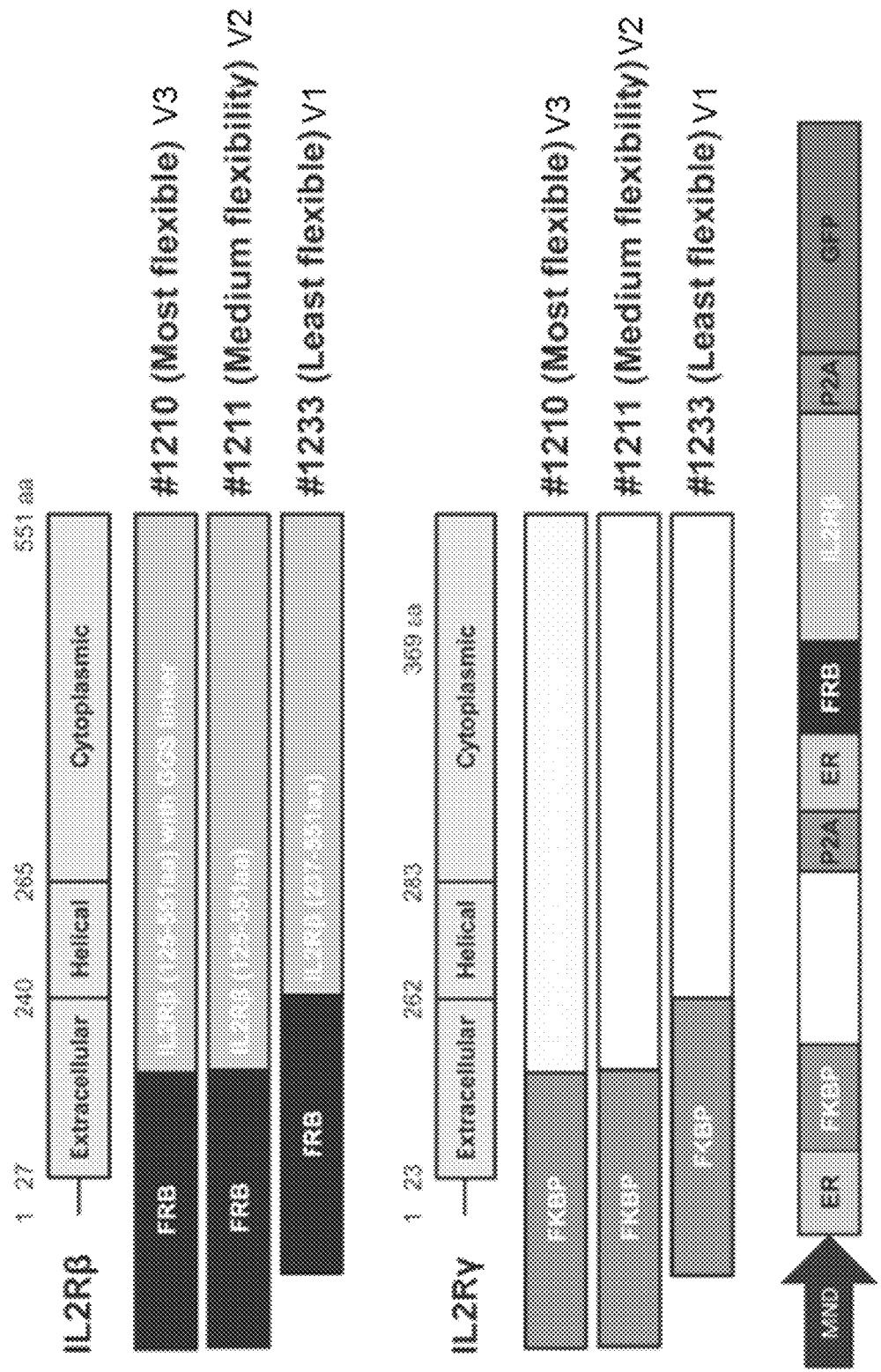
FIG. 3 depicts various embodiments of IL2R-CISC architectures. The embodiment shown in FIG. 3 shows an architecture for both FRB-IL2Rβ and for FKBP-IL2Rγ, providing schematics for various degrees of flexibility, comprising most flexible (1210—this embodiment incorporates a short linker sequence the entire first extracellular immunoglobulin superfamily (IgSF) domain of the IL2R and its TM and cytosolic tail regions), medium flexibility (1211—this embodiment incorporates the entire first extracellular IgSF domain of the IL2R and its TM and cytosolic tail regions), and least flexible (1233—this embodiment incorporates only the IL2R TM and cytosolic tail regions).

In some embodiments, a protein sequence or sequences for heterodimeric two component CISC are provided. In some embodiments, the first CISC component is an IL2Rγ-CISC complex. FIG. 3 schematically depicts the CISC construct design, including CISC having varying amino acid sequence lengths extending from the transmembrane spans. The varying amino acid sequence lengths may confer varied degrees of flexibility, as described herein, and as shown schematically in FIG. 3. The schematics depicted in FIG. 3 may be encompassed by the following sequences, which provide details of the schematic constructs by way of example, and are not intended to be limiting in scope.

In some embodiments, the IL2Rγ-CISC comprises an amino acid sequence as set forth in SEQ ID NO: 1 (MPLGLLWLGLALLGAL-HAQAGVQVETISPGDGRTFPKRGQTCVVHYTGMLE DGK KFDSSRDRNKPFKFMLGKQEVIR-GWEEGVAQMSVGQRAKLTISPDYAYGATGHPGI IPPHATLVFDVELLKLGEGSNTSKENPFLFALEAV-VISVGSMGLIISLLCVYFWLERT MPRIPTLKN-LEDLVTEYHGNFSAWSGVSKGLAESLQPDYSER-LCLVSEIPPKGGALG EGPGASPCNQHSPYWAPPCYTLKPET; SEQ ID NO: 1). Embodiments also comprise a nucleic acid sequence encoding the protein sequence of SEQ ID NO: 1.

In some embodiments, the IL2Rγ-CISC comprises an amino acid sequence as set forth in SEQ ID NO: 3 (MPLGLLWLGLALLGAL-HAQAGVQVETISPGDGRTFPKRGQTCVVHYTGMLE DGK KFDSSRDRNKPFKFMLGKQEVIR-GWEEGVAQMSVGQRAKLTISPDYAYGATGHPGI IPPHATLVFDVELLKLEGGGSQNLVIPWAP-ENLTLHKLSESQLELNWNNRFLNHCLE HLVQYRTDWDHSWTE-QSVDYRHKFSLPSVDGQKRYTFRVRSRFN-PLCGSAQHWSE WSHPIHWGSNTSKENPFLFALEAV-VISVGSMGLIISLLCVYFWLERTMPRIPTLKNLE DLVTEYHGNFSAWSGVSKGLAESLQPDYSERLCLV-SEIPPKGGALGEGPGASPCNQH SPYWAPPCYTLK-PET; SEQ ID NO: 3). Embodiments also comprise a nucleic acid sequence encoding the protein sequence of SEQ ID NO: 3.

In some embodiments, the IL2Rγ-CISC comprises an amino acid sequence as set forth in SEQ ID NO: 5 (MPLGLLWLGLALLGAL-HAQAGVQVETISPGDGRTFPKRGQTCVVHYTGMLED GK KFDSSRDRNKPFKFMLGKQEVIR-GWEEGVAQMSVGQRAKLTISPDYAYGATGHPGI IPPHATLVFDVELLKLEGQNLVIPWAPENLTLHKLS-ESQLELNWNNRFLNHCLEHLV QYRTDWDHSWTE-QSVDYRHKFSLPSVDGQKRYTFRVRSRFN-PLCGSAQHWSEWSH PIHWGSNTSKENPFLFALEAVVISVGSMGLIIS-LLCVYFWLERTMPRIPTLKNLEDLVT EYHGNF-SAWSGVSKGLAESLQPDYSERLCLVSEIPPKGGAL-GEGPGASPCNQHSPYW APPCYTLKPET; SEQ ID NO: 5). Embodiments also comprise a nucleic acid sequence encoding the protein sequence of SEQ ID NO: 5.

In some embodiments, the IL2Rγ-CISC comprises an amino acid sequence as set forth in SEQ ID NO: 7 (MPLGLLWLGLALLGAL-HAQAGVQVETISPGDGRTFPKRGQTCVVHYTGMLE DGK KFDSSRDRNKPFKFMLGKQEVIR-GWEEGVAQMSVGQRAKLTISPDYAYGATGHPGI IPPHATLVFDVELLKLEGGSNTSKENPFLFALEAV-VISVGSMGLIISLLCVYFWLERT MPRIPTLKN-LEDLVTEYHGNFSAWSGVSKGLAESLQPDYSER-LCLVSEIPPKGGALG EGPGASPCNQHSPYWAPPCYTLKPET; SEQ ID NO: 7). Embodiments also comprise a nucleic acid sequence encoding the protein sequence of SEQ ID NO: 7.

In some embodiments, the protein sequence for the first CISC component includes a protein sequence encoding an extracellular binding domain, a hinge domain, a transmembrane domain, or a signaling domain. Embodiments also comprise a nucleic acid sequence encoding the extracellular binding domain, the hinge domain, the transmembrane domain, or the signaling domain. In some embodiments, the protein sequence of the first CISC component, comprising the first extracellular binding domain, the hinge domain, the transmembrane domain, and/or the signaling domain comprises an amino acid sequence that comprises a 100%, 99%, 98%, 95%, 90%, 85%, or 80% sequence identity to the sequence set forth in SEQ ID NOs: 1, 3, 5, or 7, or has a sequence identity that is within a range defined by any two of the aforementioned percentages.

In some embodiments, the second CISC component is an IL2Rβ complex. In some embodiments, the IL2Rβ-CISC comprises an amino acid sequence as set forth in SEQ ID NO: 2 (MALPVTALLLPLALLL-HAARPILWHEMWHEGLEEASRLYFGERNVKGMFE-VLEPL HAMMERGPQTLKETSFNQAYGRDLMEA-QEWCRKYMKSGNVKDLLQAWDLYYHV FRRISKGKDTIPWLGHLLVGLSGAFGFIILV-YLLINCRNTGPWLKKVLKCNTPDPSKF FSQLSSEHGGDVQKWLSSPFPSSSFSPGGLAPEIS-PLEVLERDKVTQLLLQQDKVPEP ASLSSNHSLT-SCFTNQGYFFFHLPDALEIEACQVYFTYDPYSEEDP-DEGVAGAPTGSS PQPLQPLSGEDDAYCTFPSRDDLLLFSPSLLGGPSPP-STAPGGSGAGEERMPPSLQER VPRDWDPQPLGPPTPGVPDLVDFQPPPELVLREA-GEEVPDAGPREGVSFPWSRPPGQ GEFRAL-NARLPLNTDAYLSLQELQGQDPTHLV; SEQ ID NO: 2). Embodiments also comprise a nucleic acid sequence encoding the protein sequence of SEQ ID NO: 2.

In some embodiments, the IL2Rβ-CISC comprises an amino acid sequence as set forth in SEQ ID NO: 4 (MALPVTALLLPLALLLHAARPILWHEMWHEGLEE-ASRLYFGERNVKGMFEVLEPL HAM-MERGPQTLKETSFNQAYGRDLMEAQEWCR-KYMKSGNVKDLLQAWDLYYHV FRRISKGGSKPFENLRLMAPISLQVVHVETHRCNIS-WEISQASHYFERHLEFEARTLSP GHTWEE- APLLTLKQKQEWICLETLTPDTQYEFQVRVKPLQGEFTTWSPWSQPLAFRT KPAALGKDTIPWLGHLLVGLSGAFGFIILVYLLINCRNTGPWLKKVLKCNTPDPSKFF QLSSEHGGDVQKWLSSPFSSSFSPGGLAPEISPLEVLERDKVTQLLLQQDKVPEPAS LSSNHSLTSCFTNQGYFFFHLPDALEIEACQVYFTYDPYSEEDPDEGVAGAPTGSSPQ PLQPLSGEDDAYCTFPSRDDLLLFSPSLLGGPSPPSTAPGGSGAGEERMPPSLQERVPR DWDPQPLGPPTPGVPDLVDFQPPPELVLREAGEEVPDAGPREGVSFPWSRPPGQGEF RALNARLPLNTDAYLSLQELQGQDPTHLV; SEQ ID NO: 4). Embodiments also comprise a nucleic acid sequence encoding the protein sequence of SEQ ID NO: 4.

In some embodiments, the IL2Rβ-CISC comprises an amino acid sequence as set forth in SEQ ID NO: 6 (MALPVTALLLPLALLLHAARPILWHEMWHEGLEEASRLYFGERNVKGMFEVLEPL HAMMERGPQTLKETSFNQAYGRDLMEAQEWCRKYMKSGNVKDLLQAWDLYYHV FRRISKKPFENLRLMAPISLQVVHVETHRCNISWEISQASHYFERHLEFEARTLSPGHT WEEAPLLTLKQKQEWICLETLTPDTQYEFQVRVKPLQGEFTTWSPWSQPLA FRTKPA ALGKDTIPWLGHLLVGLSGAFGFIILVYLLINCRNTGPWLKKVLKCNTPDPSKFFSQL SSEHGGDVQKWLSSPFSSSFSPGGLAPEISPLEVLERDKVTQLLLQQDKVPEPASLSS NHSLTSCFTNQGYFFFHLPDALEIEACQVYFTYDPYSEEDPDEGVAGAPTGSSPQPLQ PLSGEDDAYCTFPSRDDLLLFSPSLLGGPSPPSTAPGGSGAGEERMPPSLQERVPRDW DPQPLGPPTPGVPDLVDFQPPPELVLREAGEEVPDAGPREGVSFPWSRPPGQGEFRAL NARLPLNTDAYLSLQELQGQDPTHLV; SEQ ID NO: 6). Embodiments also comprise a nucleic acid sequence encoding the protein sequence of SEQ ID NO: 6.

In some embodiments, the IL2Rβ-CISC comprises an amino acid sequence as set forth in SEQ ID NO: 8 (MALPVTALLLPLALLLHAARPILWHEMWHEGLEEASRLYFGERNVKGMFEVLEPL HAMMERGPQTLKETSWLGHLLVGLSGAFGFIILVYLLINCRNTGPWLKKVLKCNTP DPSKFFSQLSSEHGGDVQKWLSSPFSSSFSPGGLAPEISPLEVLERDKVTQLLLQQDK VPEPASLSSNHSLTSCFTNQGYFFFHLPDALEIEACQVYFTYDPYSEEDPDEGVAGAP TGSSPQPLQPLSGEDDAYCTFPSRDDLLLFSPSLLGGPSPPSTAPGGSGAGEERMPPSL QERVPRDWDPQPLGPPTPGVPDLVDFQPPPELVLREAGEEVPDAGPREGVSFPWSRP PGQGEFRALNARLPLNTDAYLSLQELQGQDPTHLV; SEQ ID NO: 8). Embodiments also comprise a nucleic acid sequence encoding the protein sequence of SEQ ID NO: 8.

In some embodiments, the second CISC component is an IL7Rα complex. In some embodiments, the IL7Rα-CISC comprises an amino acid sequence as set forth in SEQ ID NO: 9 (MALPVTALLLPLALLLHAARPILWHEMWHEGLEEASRLYFGERNVKGMFEVLEPL HAMMERGPQTLKETSFNQAYGRDLMEAQEWCRKYMKSGNVKDLLQAWDLYYHV FRRISKGEINNSSGEMDPILLTISILSFFSVALLVILACVLWKKRIKPIVWPSLPDHKKT LEHLCKKPRKNLNVSFNPESFLDCQIHRVDDIQARDEVEGFLQDTFPQQLEESEKQRL GGDVQSPNCPSEDVVITPESFGRDSSLTCLAGNVSACDAPILSSSRSLDCRESGKNGP HVYQDLLLSLGTTNSTLPPPFSLQSGILTLNPVAQGQPILTSLGSNQEEAYVTMSSFY QNQ; SEQ ID NO: 9). Embodiments also comprise a nucleic acid sequence encoding the protein sequence of SEQ ID NO: 9.

In some embodiments, the protein sequence for the second CISC component includes a protein sequence encoding an extracellular binding domain, a hinge domain, a transmembrane domain, or a signaling domain. Embodiments also comprise a nucleic acid sequence encoding the extracellular binding domain, the hinge domain, the transmembrane domain, or the signaling domain of the second CISC component. In some embodiments, the protein sequence of the second CISC component, comprising the second extracellular binding domain, the hinge domain, the transmembrane domain, and/or the signaling domain comprises an amino acid sequence that comprises a 100%, 99%, 98%, 95%, 90%, 85%, or 80% sequence identity to the sequence set forth in SEQ ID NOs: 2, 4, 6, 8, or 9, or has a sequence identity that is within a range defined by any two of the aforementioned percentages.

In some embodiments, the protein sequence may include a linker. In some embodiments, the linker comprises 1, 2, 3, 4, 5, 6, 7, 8, 9 or 10 amino acids, such as glycines, or a number of amino acids, such as glycine, within a range defined by any two of the aforementioned numbers. In some embodiments, the glycine spacer comprises at least 3 glycines. In some embodiments, the glycine spacer comprises a sequence set forth in SEQ ID NO: 15 (GGGS; SEQ ID NO: 15), SEQ ID NO 16 (GGGSGGG; SEQ ID NO: 16) or SEQ ID NO: 17 (GGG; SEQ ID NO: 17). Embodiments also comprise a nucleic acid sequence encoding SEQ ID NOs: 15-17. In some embodiments, the transmembrane domain is located N-terminal to the signaling domain, the hinge domain is located N-terminal to the transmembrane domain, the linker is located N-terminal to the hinge domain, and the extracellular binding domain is located N-terminal to the linker.

In some embodiments, a protein sequence or sequences for homodimeric two component CISC are provided. In some embodiments, the first CISC component is an IL2Rγ-CISC complex. In some embodiments, the IL2Rγ-CISC comprises an amino acid sequence as set forth in SEQ ID NO: 11 (MPLGLLWLGLALLGALHAQAGVQVETISPGDGRTFPKRGQTCVVHYTGMLE DGK KVDSSRDRNKPFKFMLGKQEVIRGWEEGVAQMSVGQRAKLTISPDYAYGATGHPGI IPPHATLVFDVELLKLEGGSNTSKENPFLFALEAVVISVGSMGLIISLLCVYFWLERT MPRIPTLKNLEDLVTEYHGNFSAWSGVSKGLAESLQPDYSERLCLVSEIPPKGGALG EGPGASPCNQHSPYWAPPCYTLKPET; SEQ ID NO: 11). Embodiments also comprise a nucleic acid sequence encoding the protein sequence of SEQ ID NO: 11.

In some embodiments, the protein sequence for the first CISC component includes a protein sequence encoding an extracellular binding domain, a hinge domain, a transmembrane domain, or a signaling domain. Embodiments also comprise a nucleic acid sequence encoding the extracellular binding domain, the hinge domain, the transmembrane domain, or the signaling domain. In some embodiments, the protein sequence of the first CISC component, comprising the first extracellular binding domain, the hinge domain, the transmembrane domain, and/or the signaling domain comprises an amino acid sequence that comprises a 100%, 99%, 98%, 95%, 90%, 85%, or 80% sequence identity to the sequence set forth in SEQ ID NOs: 11 or has a sequence identity that is within a range defined by any two of the aforementioned percentages.

In some embodiments, the second CISC component is an IL2Rβ complex or an IL2Rα complex. In some embodiments, the IL2Rβ-CISC comprises an amino acid sequence as set forth in SEQ ID NO: 10 (MPLGLLWLGLALLGALHAQAGVQVETISPGDGRTFPKRGQTCVVHYTGMLEDGK KVDSSRDRNKPFKFMLGKQEVIRGWEEGVAQMSVGQRAKLTISPDYAYGATGHPGIIPPHATLVFDVELLKLEGGKDTIPWLGHLL-VGLSGAFGFIILVYLLINCRNTGPWLKK VLKCNTPDPSKFF-SQLSSEHGGDVQKWLSSPFPSSSFSPGGLAPEISPLEV-LERDKVTQ LLLQQDKVPEPASLSSNHSLT-SCFTNQGYFFFHLPDALEIEACQVYFTYDPYSEEDPD EGVAGAPTGSSPQPLQPLSGEDDAYCTFPSRDDLLLF-SPSLLGGPSPPSTAPGGSGAG EERM-PPSLQERVPRDWDPQPLGPPTPGVPDLVDFQPPPEL-VLREAGEEVPDAGPREG VSFPWSRPPGQGEFRALNARLPLNTDAY-LSLQELQGQDPTHLV; SEQ ID NO: 10). Embodiments also comprise a nucleic acid sequence encoding the protein sequence of SEQ ID NO: 10.

In some embodiments, the IL2Rα-CISC comprises an amino acid sequence as set forth in SEQ ID NO: 12 (MPLGLLWLGLALLGAL-HAQAGVQVETISPGDGRTFPKRGQTCVVHYTGMLEDGK KVDSSRDRNKPFKFMLGKQEVIRGWEEGVAQMSVGQRAKLTISPDYAYGATGHPGIIPPHATLVFD-VELLKLEGEINNSSGEMDPILLTISILSFFSVALLVI-LACVLWKKRIKPIV WPSLPDHKKTLEHLCKKPRKNLNVSFNPESFLDCQI HRVDDIQARDEVEGFLQDTFP QQLEESEKQRLGGDVQSPNCPSEDVVIT-PESFGRDSSLTCLAGNVSACDAPILSSSRSL DCRESGKNGPHVYQDLLLSLGTTN-STLPPPFSLQSGILTLNPVAQGQPILTSLGSNQEE AYVTMSSFYQNQ; SEQ ID NO: 12). Embodiments also comprise a nucleic acid sequence encoding the protein sequence of SEQ ID NO: 12.

In some embodiments, the protein sequence for the second CISC component includes a protein sequence encoding an extracellular binding domain, a hinge domain, a transmembrane domain, or a signaling domain. Embodiments also comprise a nucleic acid sequence encoding the extracellular binding domain, the hinge domain, the transmembrane domain, or the signaling domain of the second CISC component. In some embodiments, the protein sequence of the second CISC component, comprising the second extracellular binding domain, the hinge domain, the transmembrane domain, and/or the signaling domain comprises an amino acid sequence that comprises a 100%, 99%, 98%, 95%, 90%, 85%, or 80% sequence identity to the sequence set forth in SEQ ID NO: 10 or SEQ ID NO: 12, or has a sequence identity that is within a range defined by any two of the aforementioned percentages.

In some embodiments, the protein sequence may include a linker. In some embodiments, the linker comprises 1, 2, 3, 4, 5, 6, 7, 8, 9 or 10 amino acids, such as glycines, or a number of amino acids, such as glycine, within a range defined by any two of the aforementioned numbers. In some embodiments, the glycine spacer comprises at least 3 glycines. In some embodiments, the glycine spacer comprises a sequence set forth in SEQ ID NO: 15 (GGGS; SEQ ID NO: 15), SEQ ID NO: 16 (GGGSGGG; SEQ ID NO: 16) or SEQ ID NO: 17 (GGG; SEQ ID NO: 17). Embodiments also comprise a nucleic acid sequence encoding SEQ ID NOs: 15-17. In some embodiments, the transmembrane domain is located N-terminal to the signaling domain, the hinge domain is located N-terminal to the transmembrane domain, the linker is located N-terminal to the hinge domain, and the extracellular binding domain is located N-terminal to the linker.

In some embodiments, the sequences for the homodimerizing two component CISC incorporate FKBP F36V domain for homodimerization with the ligand AP1903.

In some embodiments is provided a protein sequence or sequences for single component homodimerization CISC. In some embodiments, the single component CISC is an IL7Rα-CISC complex. In some embodiments, the IL7Rα-CISC comprises an amino acid sequence as set forth in SEQ ID NO: 13 (MPLGLLWLGLALLGAL-HAQAGVQVETISPGDGRTFPKRGQTCVVHYTGMLEDGK KVDSSRDRNKPFKFMLGKQEVIRGWEEGVAQMSVGQRAKLTISPDYAYGATGHPGIIPPHATLVFD-VELLKLEGEINNSSGEMDPILLTISILSFFSVALLVI-LACVLWKKRIKPIV WPSLPDHKKTLEHLCKKPRKNLNVSFNPESFLDCQI HRVDDIQARDEVEGFLQDTFP QQLEESEKQRLGGDVQSPNCPSEDVVIT-PESFGRDSSLTCLAGNVSACDAPILSSSRSL DCRESGKNGPHVYQDLLLSLGTTN-STLPPPFSLQSGILTLNPVAQGQPILTSLGSNQEE AYVTMSSFYQNQ; SEQ ID NO: 13). Embodiments also comprise a nucleic acid sequence encoding the protein sequence of SEQ ID NO: 13.

In some embodiments, the single component CISC is an MPL-CISC complex. In some embodiments, the MPL-CISC comprises an amino acid sequence as set forth in SEQ ID NO: 14 (MPLGLLWLGLALLGAL-HAQAGVQVETISPGDGRTFPKRGQTCVVHYTGMLEDGK KVDSSRDRNKPFKFMLGKQEVIRGWEEGVAQMSVGQRAKLTISPDYAYGATGHPGIIPPHATLVFDVELLKLGEETAWISLVTALHLVLGL-SAVLGLLLLRWQFPAHYRRLRH ALWPSLPDLHRVLGQYLRDTAALSPPKATVSDT-CEEVEPSLLEILPKSSERTPLPLCSS QAQMDYRRLQP-SCLGTMPLSVCPPMAESGSCCTTHIANHSYLPL-SYWQQP; SEQ ID NO: 14). Embodiments also comprise a nucleic acid sequence encoding the protein sequence of SEQ ID NO: 14.

In some embodiments, the protein sequence for the single component CISC includes a protein sequence encoding an extracellular binding domain, a hinge domain, a transmembrane domain, or a signaling domain. Embodiments also comprise a nucleic acid sequence encoding the extracellular binding domain, the hinge domain, the transmembrane domain, or the signaling domain. In some embodiments, the protein sequence of the first CISC component, comprising the first extracellular binding domain, the hinge domain, the transmembrane domain, and/or the signaling domain comprises an amino acid sequence that comprises a 100%, 99%, 98%, 95%, 90%, 85%, or 80% sequence identity to the sequence set forth in SEQ ID NO: 13 or SEQ ID NO: 14 or has a sequence identity that is within a range defined by any two of the aforementioned percentages.

In some embodiments, the protein sequence may include a linker. In some embodiments, the linker comprises 1, 2, 3, 4, 5, 6, 7, 8, 9 or 10 amino acids, such as glycines, or a number of amino acids, such as glycine, within a range defined by any two of the aforementioned numbers. In some embodiments, the glycine spacer comprises at least 3 glycines. In some embodiments, the glycine spacer comprises a sequence set forth in SEQ ID NO: 15 (GGGS; SEQ ID NO: 15), SEQ ID NO: 16 (GGGSGGG; SEQ ID NO: 16) or SEQ ID NO: 17 (GGG; SEQ ID NO: 17). Embodiments also comprise a nucleic acid sequence encoding SEQ ID NOs: 15-17. In some embodiments, the transmembrane domain is located N-terminal to the signaling domain, the hinge domain is located N-terminal to the transmembrane domain, the linker is located N-terminal to the hinge domain, and the extracellular binding domain is located N-terminal to the linker.

In some embodiments, the sequences for the homodimerizing single component CISC incorporate FKBP F36V domain for homodimerization with the ligand AP1903.

Vectors for Expressing the Dimeric CISC Components

A variety of vector combinations can be constructed to provide for efficient transduction and transgene expression. In some embodiments, the vector is a viral vector. In other embodiments, the vectors can include a combination of viral vectors and plasmid vectors. Other viral vectors include foamy virus, adenoviral vectors, adeno-associated viral (AAV) vectors, retroviral vectors, and/or lentiviral vectors. In some embodiments, the vector is a lentiviral vector. In some embodiments, the vector is a foamy viral vector, adenoviral vectors, retroviral vectors or lentiviral vectors. In some embodiments, the vector is for protein expression in a bacterial system, such as E. coli. In other embodiments, a first vector can encode a first CISC component comprising a first extracellular binding domain or portion thereof, a hinge domain, a transmembrane domain, and a signaling domain or portion thereof while a second vector can encode a second CISC component comprising a second extracellular binding domain or a portion thereof, a hinge domain, a transmembrane domain, and a signaling domain or portions thereof.

In some embodiments, the expression vector comprises a nucleic acid encoding the protein sequence of SEQ ID NOs: 1, 2, 3, 4, 5, 6, 7, 8, or 9. In some embodiments, the expression vector comprises a nucleic acid sequence as set forth in SEQ ID NO: 20 (AGCTTAATGTAGTCT-TATGCAATACTCTTGTAGTCTTGCAACATGGTAAC-GATGA GTTAGCAACATGCCTTA-CAAGGAGAGAAAAAGCACCGTGCATGCCGATTGG TGG AAGTAAGGTGGTACGATCGTGCCTTATTAG-GAAGGCAACAGACGGGTCTGACAT GGAT-TGGACGAACCACTGAATTGCCGCATTGCAGAGAT-ATTGTATTTAAGTGCCT
AGCTCGATACAATAAACGGGTCTCTCTGGTTA-GACCAGATCTGAGCCTGGGAGC
TCTCTGGCTAACTAGGGAACCCACTGCTTAAGCCT-CAATAAAGCTTGCCTTGAGT GCTT-CAAGTAGTGTGTGCCCGTCTGTTGTGTGACTCTGG TAACTAGAGATCCCTC AGACCCTTT-TAGTCAGTGTG-
GAAAATCTCTAGCAGTGGCGCCCGAACAGGGACT TGAAAGCGAAAGGGAAACCAGAG-
GAGCTCTCTCGACGCAGGACTCGGCTTGCTG AAGCGCGCACGGCAAGAGGCGAGGGGCGGCGAC TGGTGAGTACGCCAAAAATT TTGACTAGCG-GAGGCTAGAAGGAGAGAGATGGGTGCGAGAGCG TCAGTATTAA GCGGGGGAGAATTAGATCGCGATGG-GAAAAAATTCGGTTAAGGCCAGGGGGAA AGAAAAAATATAAATTAAAA-
CATATAGTATGGGCAAGCAGGGAGCTAGAACGA TTCGCAGTTAATCCTGGCCTGTTAGAAA-
CATCAGAAGGCTGTAGACAAATACTG GGACAGC-TACAACCATCCCTTCAGACAGGATCAGAAGAACT-TAGATCATTATAT
AATACAGTAGCAACCCTCTATTGTGTGCAT-CAAAGGATAGAGATAAAAGACACC AAGGAAGCTT-TAGACAAGATAGAG-
GAAGAGCAAAACAAAAGTAAGACCACCGC ACAGCAAGCGGCCGCTGATCTTCAGACCTGGAG-GAGGAGATATGAGGGACAATT GGAGAAGTGAAT-TATATAAATATAAAGTAGTAAAAATTGAACCATTAG-GAGTAG
CACCCAC-
CAAGGCAAAGAGAAGAGTGGTGCAGAGAGAAAA AAGAGCAGTGGGA ATAG-GAGCTTTGTTCCTTGGGTTCTTGGGAGCAGCAG-GAAGCACTATGGGCGCA GCCT-CAATGACGCTGACGGTACAGGCCAGACAATTATTG TCTGGTATAGTGCAG CAGCAGAACAATTTGCT-GAGGGCTATTGAGGCGCAACAG-
CATCTGTTGCAACTC ACAGTCTGGGGCAT-CAAGCAGCTCCAGGCAAGAATCCTGGCTGTGGAAA-GATAC
CTAAAGGATCAACAGCTCCTGGGGAT-CTGGGGTTGCTCTGGAAAACTCATTTGCA CCACTGCTGTGCCTTGGAATGCTAGTTG-GAGTAATAAATCTCTGGAACAGATTTG GAAT-CACACGACCTGGATGGAGTGGGACAGAGAAAT-TAACAATTACACAAGCTT
AATACACTCCTTAATT-
GAAGAATCGCAAAACCAGCAAGAAAAGAAT-GAACAAG AATTATTGGAATTAGA-TAAATGGGCAAGTTTGTGGAATTGGTTTAACATAA CAA ATTGGCTGTGGTATATAAAATTATTCATAATGA-TAGTAGGAGGCTTGGTAGGTTT
AAGAATAGTTTTTGCTGTACTTTCTATAGT-GAATAGAGTTAGGCAGGGATATTCA CCAT-TATCGTTTCAGACCCACCTCC-
CAACCCCGAGGGGACCCGACAGGCCCGAA GGAATAGAAGAAGAAGGTGGAGAGAGAGACAGA-GACAGATCCATTCGATTAGT GAACG-GATCTCGACGGTATCGGTTAACTTT-
TAAAAGAAAAGGGGGGATTGGGGG GTACAGTGCAGGGGAAAGAATAGTAGACAT-AATAGCAACAGACATACAAACTA AAGAATTA-CAAAAACAAATTACAAAAATTCAAAATTTTATC-GATCACGAGACTA
GCCTCGAGAAGCTTGATATCGAATTCC-CACGGGGTTGGACGCGTAGGAACAGAG AAACAG-GAGAATATGGGCCAAACAGGA-
TATCTGTGGTAAGCAGTTCCTGCCCCG
GCTCAGGGCCAAGAACAGTTG-
GAACAGCAGAATATGGGCCAAACAGGATATCTG TGGTAAGCAGTTCCTGCCCCGGCTCAGGGC-CAAGAACAGATGGTCCCCAGATGC
GGTCCCGCCCTCAGCAGTTTCTAGAGAACCATCA-GATGTTTCCAGGGTGCCCCAA GGACCT-GAAATGACCCTGTGCCTTATTTGAACTAAC-CAATCAGTTCGCTTCTCGC
TTCTGTTCGCGCGCTTCTGCTCCCCGAGCTC-TATATAAGCAGAGCTCGTTTAGTG AACCGTCA-GATCGCTAGCACCGGTGCCGCCAC-
CATGCCTCTGGGCCTGCTGTGGC TGGGCCTGGCCCTGCTGGGCGCCCTGCACGCCCAG GCCGGCGTGCAGGTGGAGA
CAATCTCCCCAGGCGACGGACGCACAT-TCCCTAAGCGGGGCCAGACCTGCGTGG TGCAC-TATACAGGCATGCTGGAG-
GATGGCAAGAAGTTTGACAGCTCCCGGGATA GAAACAAGCCATTCAAGTT-
TATGCTGGGCAAGCAGGAAGT-
GATCAGAGGCTGGG AGGAGGGCGTGGCCCA-
GATGTCTGTGGGCCAGAGGGCCAAGCTGACCATCA
GCC CAGACTACGCCTATGGAGCAACAGGC-
CACCCAGGAATCATCCCACCTCACGCCA
CCCTGGTGTTCGATGTGGAGCTGCT-
GAAGCTGGGCGAGGGATCCAACACATCAA
AAGAGAACCCCTTTCTGTTCGCATTG-
GAGGCCGTAGTCATATCTGTTGGATCCAT GGGACT-
TATTATCTCCCTGTTGTGTGTGTACTTCTGGCTG-
GAACGGACTATGCCC
AGGATCCCCACGCTCAAGAATCTGGAAGATCTCGT-
CACAGAATACCATGGTAAT TTCAGCGCCTGGAGCG-
GAGTCTCTAAGGGTCTGGCCGAATCCCTCCAACCC-
GATT
ATTCTGAACGGTTGTGCCTCGTATCCGAAATAC-
CACCAAAAGGCGGGGCTCTGG
GTGAGGGCCCAGGGGCGAGTCCGTGCAAT-
CAACACAGCCCGTATTGGGCCCCTC CTTGT-
TATACGTTGAAGCCCGAAACTGGAAGCGGAGC-
TACTAACTTCAGCTGCT
GAAGCAGGCTGGAGCGTGGAG-
GAGAACCCTGGACCTATGGCACTGCCCGTGAC
CGCCCTGCTGCTGCCTCTGGCCCTGCTGCTGCACG
CAGCCCGGCCTATCCTGTGG
CACGAGATGTGGCACGAGGGCCTGGAG-
GAGGCCAGCAGGCTGTATTTTGGCGAG
CGCAACGTGAAGGGCATGTTCGAGGTGCTG-
GAGCCTCTGCACGCCATGATGGAG AGAGGCC-
CACAGACCCTGAAGGAGACATCCTT-
TAACCAGGCCTATGGACGGGAC
CTGATGGAGGCACAGGAGTGGTGCAGAAAGTA-
CATGAAGTCTGGCAATGTGAAG
GACCTGCTGCAGGCCTGGGATCTGTACTAT-
CACGTGTTTCGGAGAATCTCCAAGG GCAAA-
GACACGATTCCGTGGCTTGGG-
CATCTGCTCGTTGGGCTGAGTGGTGCGTT
TGGTTTCATCATCTTGGTCTATCTCTTGATCAAT-
TGCAGAAATACAGGCCCTTGGC
TGAAAAAAGTGCTCAAGTGTAATACCCCCGACC-
CAAGCAAGTTCTTCTCCCAGCT TTCTTCAGAG-
CATGGAGGCGATGTGCAGAAATGGCTCTCTT-
CACCTTTTCCCTCC
TCAAGCTTCTCCCCGG-
GAGGGCTGGCGCCCGAGATTTCACCTCTT-
GAGGTACTTG AACGAGACAAGGTTACC-
CAACTTCTCCTTCAACAGGATAAGGTACCCGAACC
TG CGAGCCTTAGCTCCAACCACTCTCT-
TACGAGCTGCTTCACCAATCAGGGATACTT
CTTTTTCCACCTTCCCGATGCGCTG-
GAAATCGAAGCTTGTCAAGTTTACTTTACCT
ATGATCCATATAGCGAGGAA-
GATCCCGACGAAGGAGTCGCCGGTGCGCCCACGG
GTTCCTCACCCCAACCTCTCCAGCCTCTCTCAG-
GAGAAGATGATGCTTATTGCAC TTTTCCCAGTAGA-
GACGATCTCCTCCTCTTTTCTC-
CATCTCTTTTGGGGGGACCTT
CCCCCCCTTC-
TACGGCACCTGGCGGGTCTGGTGCTGGCGAG-
GAGCGGATGCCGC CGTCCCTCCAGGAGCGAGTAC-
CACGAGATTGGGATCCCCAGCCACTTGGACCCC
CCACCCCCGCCGTACCTGACCTTGTCGATTTT-
CAACCTCCCCCTGAATTGGTGCT
GCGAGAGGCTGGGGAG-
GAAGTTCCGGACGCTGGGCCGAGG-
GAGGGCGTGTCCTT TCCATG-
GAGTAGGCCTCCAGGTCAAGGCGAGTTTAGGGC
TCTCAACGCGCGGCT GCCGTTGAATACAGACGCT-
TATCTCTCACTGCAGGAACTGCAAGGTCAGGACCC
AACACATCTTGTAGGATCTGGTGCTACTAAT-
TTTTCTCTTTTGAAGCAAGCTGGA GATGTT-
GAAGAGAACCCTGGTCCAGTGAGCAAGGGCGAG-
GAGCTGTTCACCGGG
GTGGTGCC-
CATCCTGGTCGAGCTGGACGGCGACGTAAACGGC-
CACAAGTTCAGC GTGTCCGGCGAGGGCGAGGGC-
GATGCCACCTACGGCAAGCTGACCCTGAAGTTC
ATCTGCAC-
CACCGGCAAGCTGCCCGTGCCCTGGCC-
CACCCTCGTGACCACCCTGA
CCTACGGCGTGCAGTGCTTCAGCCGCTACCCCGAC-
CACATGAAGCAGCACGACT TCTTCAAGTCCGC-
CATGCCCGAAGGCTACGTCCAGGAGCGCAC-
CATCTTCTTCAA
GGACGACGGCAACTACAAGACCCGCGCCGAGGT-
GAAGTTCGAGGGCGACACCC TGGTGAACCG-
CATCGAGCTGAAGGGCATCGACTT-
CAAGGAGGACGGCAACATCC
TGGGGCACAAGCTGGAGTACAACTACAACAGC-
CACAACGTCTATATCATGGCCG
ACAAGCAGAAGAACGGCATCAAGGTGAACTTCAA-
GATCCGCCACAACATCGAG
GACGGCAGCGTGCAGCTCGCCGACCAC-
TACCAGCAGAACACCCCCATCGGCGAC
GGCCCCGTGCTGCTGCCCGACAACCACTACCT-
GAGCACCCAGTCCGCCCTGAGC AAAGACCC-
CAACGAGAAGCGCGATCACATGGTCCTGCTG-
GAGTTCGTGACCGCC
GCCGGGATCACTCTCGGCATGGACGAGCTGTA-
CAAGTAAACTAGTGTCGACAAT CAACCTCTGGAT
TACAAAATTTGTGAAAGATTGACTGGTATTCT-
TAACTATGTTG
CTCCTTTTACGCTATGTGGATACGCTGCTT-
TAATGCCTTTGTATCATGCTATTGCT
TCCCGTATGGCTTTCAT-
TTTCTCCTCCTTGTATAAATCCTGGTTGCTGTCTCTT-
TAT GAG-
GAGTTGTGGCCCGTTGTCAGGCAACGTGGCGTGG
TGTGCACTGTGTTTGCTG ACGCAACCCC-
CACTGGTTGGGGCATTGCCAC-
CACCTGTCAGCTCCTTTCCGGGAC
TTTCGCTTTCCCCCTCCCTATTGCCACGGCGGAACT-
CATCGCCGCCTGCCTTGCCC
GCTGCTGGACAGGGGCTCGGCTGTTGGGCACTGA
CAATTCCGTGGTGTTGTCGGG
GAAGCTGACGTCCTTTC-
CATGGCTGCTCGCCTGTGTTGCCACCTGGAT-
TCTGCGC GGGACGTCCTTCTGC-
TACGTCCCTTCGGCCCTCAATCCAGCGGACCTTCCT
TCCC
GCGGCCTGCTGCCGGCTCTGCGGCCTCTTCCGCGT
CTTCGCCTTCGCCCTCAGAC GAGTCG-
GATCTCCCTTTGGGCCGCCTCCCCGCCTGGAAT-
TCGAGCTCGGTACCTT TAAGACCAATGACTTA-
CAAGGCAGCTGTAGATCTTAGCCACTTTTTAAAAG
AAA AGGGGGGACTGGAAGGGCTAATTCACTCC-
CAACGAAGACAAGATCTGCTTTTTG
CTTGTACTGGGTCTCTCTGGTTAGACCAGATCT-
GAGCCTGGGAGCTCTCTGGCTA ACTAGGGAACC-
CACTGCTTAAGCCTCAATAAAGCTTGCCTT-
GAGTGCTTCAAGTA
GTGTGTGCCCGTCTGTTGTGTGACTCTGGTAACTA
GAGATCCCTCA- GACCCTTTT AGTCAGTGTGGAAAATCTCTAGCAGTAGTAGTTCATGTCATCTTATTATTCAGTA TTTATAACTTGCAAAGAAATGAATATCAGAGAGTGAGAGGAACTTGTTTATTGC AGCTTATAATGGTTACAAATAAAGCAATAGCATCACAAATTTCACAAATAAAGC ATTTTTTTCACTGCATTCTAGTTGTGGTTTGTCCAAACTCATCAATGTATCTTATC ATGTCTGGCTCTAGCTATCCCGCCCCTAACTCCGCCCAGTTCCGCCCATTCTCCGC CCCATGGCTGACTAATTTTTTTATTTATGCAGAGGCCGAGGCCGCCTCGGCCTC TGAGCTATTCCAGAAGTAGTGAGGAGGCTTTTTTGGAGGCCTAGGCTTTTGCGTC GAGACGTACCCAATTCGCCCTATAGTGAGTCGTATTACGCGCGCTCACTGGCCGT CGTTTTACAACGTCGTGACTGGGAAAACCCTGGCGTTACCCAACTTAATCGCCTT GCAGCACATCCCCCTTTCGCCAGCTGGCGTAATAGCGAAGAGGCCCGCACCGAT CGCCCTTCCCAACAGTTGCGCAGCCTGAATGGCGAATGGCGCGACGCGCCCTGT AGCGGCGCATTAAGCGCGGCGGGTGTGGTGGTTACGCGCAGCGTGACCGCTACA CTTGCCAGCGCCCTAGCGCCCGCTCCTTTCGCTTTCTTCCCTTCCTTTCTCGCCAC GTTCGCCGGCTTTCCCCGTCAAGCTCTAAATCGGGGGCTCCCTTTAGGGTTCCGA TTTAGTGCTTTACGGCACCTCGACCCCAAAAAACTTGATTAGGGTGATGGTTCAC GTAGTGGGCCATCGCCCTGATAGACGGTTTTTCGCCCTTTGACGTTGGAGTCCAC GTTCTTTAATAGTGGACTCTTGTTCCAAACTGGAACAACACTCAACCCTATCTCG GTCTATTCTTTTGATTTATAAGGGATTTTGCCGATTTCGGCCTATTGGTTAAAAAA TGAGCTGATTTAACAAAAATTTAACGCGAATTTTAACAAAATATTAACGTTTACA ATTTCCCAGGTGGCACTTTTCGGGGAAATGTGCGCGGAACCCCTATTTGTTTATT TTTCTAAATACATTCAAATATGTATCCGCTCATGAGACAATAACCCTGATAAATG CTTCAATAATATTGAAAAAGGAAGAGTATGAGTATTCAACATTTCCGTGTCGCCC TTATTCCCTTTTTTGCGGCATTTTGCCTTCCTGTTTTTGCTCACCCAGAAACGCTG GTGAAAGTAAAAGATGCTGAAGATCAGTTGGGTGCACGAGTGGGTTACATCGAA CTGGATCTCAACAGCGGTAAGATCCTTGAGAGTTTTCGCCCCGAAGAACGTTTTC CAATGATGAGCACTTTTAAAGTTCTGCTATGTGGCGCGGTATTATCCCGTATTGA CGCCGGGCAAGAGCAACTCGGTCGCCGCATACACTATTCTCAGAATGACTTGGT TGAGTACTCACCAGTCACAGAAAAGCATCTTACGGATGGCATGACAGTAAGAGA ATTATGCAGTGCTGCCATAACCATGAGTGATAACACTGCGGCCAACTTACTTCTG ACAACGATCGGAGGACCGAAGGAGCTAACCGCTTTTTTGCACAACATGGGGGAT CATGTAACTCGCCTTGATCGTTGGGAACCGGAGCTGAATGAAGCCATACCAAAC GACGAGCGTGACACCACGATGCCTGTAGCAATGGCAACAACGTTGCGCAAACTA TTAACTGGCGAACTACTTACTCTAGCTTCCCGGCAACAATTAATAGACTGGATGG AGGCGGATAAAGTTGCAGGACCACTTCTGCGCTCGGCCCTTCCGGCTGGCTGGTT TATTGCTGATAAATCTGGAGCCGGTGAGCGTGGGTCTCGCGGTATCATTGCAGCA CTGGGGCCAGATGGTAAGCCCTCCCGTATCGTAGTTATCTACACGACGGGGAGT CAGGCAACTATGGATGAACGAAATAGACAGATCGCTGAGATAGGTGCCTCACTG ATTAAGCATTGGTAACTGTCAGACCAAGTTTACTCATATATACTTTAGATTGATT TAAAACTTCATTTTTAATTTAAAAGGATCTAGGTGAAGATCCTTTTTGATAATCTC ATGACCAAAATCCCTTAACGTGAGTTTTCGTTCCACTGAGCGTCAGACCCCGTAG AAAAGATCAAAGGATCTTCTTGAGATCCTTTTTTTCTGCGCGTAATCTGCTGCTTG CAAACAAAAAAACCACCGCTACCAGCGGTGGTTTGTTTGCCGGATCAAGAGCTA CCAACTCTTTTTCCGAAGGTAACTGGCTTCAGCAGAGCCAGATACCAAATACTG TCCTTCTAGTGTAGCCGTAGTTAGGCCACCACTTCAAGAACTCTGTAGCACCGCC TACATACCTCGCTCTGCTAATCCTGTTACCAGTGGCTGCTGCCAGTGGCGATAAG TCGTGTCTTACCGGGTTGGACTCAAGACGATAGTTACCGGATAAGGCGCAGCGG TCGGGCTGAACGGGGGGTTCGTGCACACAGCCCAGCTTGGAGCGAACGACCTAC ACCGAACTGAGATACCTACAGCGTGAGCTATGAGAAAGCGCCACGCTTCCCGAA GGGAGAAAGGCGGACAGGTATCCGGTAAGCGGCAGGGTCGGAACAGGAGAGCG CACGAGGGAGCTTCCAGGGGGAAACGCCTGGTATCTTTATAGTCCTGTCGGGTTT CGCCACCTCTGACTTGAGCGTCGATTTTTGTGATGCTCGTCAGGGGGGCGGAGCC TATGGAAAAACGCCAGCAACGCGGCCTTTTTACGGTTCCTGGCCTTTTGCTGGCC TTTTGCTCACATGTTCTTTCCTGCGTTATCCCTGATTCTGTGGATAACCGTATTA CCGCCTTTGAGTGAGCTGATACCGCTCGCCGCAGCCGAACGACCGAGCGCAGCG AGTCAGTGAGCGAGGAAGCGGAAGAGCGCCCAATACGCAAACCGCCTCTCCCCG CGCGTTGGCCGATTCATTAATGCAGCTGGCACGACAGGTTTCCCGACTGGAAAG CGGGCAGTGAGCGCAACGCAATTAATGTGAGTTAGCTCACTCATTAGGCACCCC AGGCTTTACACTTTATGCTTCCGGCTCGTATGTTGTGTGGAATTGTGAGCGGATA ACAATTTCACACAGGAAACAGCTATGACCATGATTACGCCAAGCGCGCAATTAA CCCTCACTAAAGGGAACAAAAGCTGGAGCTGCA; SEQ ID NO: 20). SEQ ID NO: 20 encodes the protein sequences as set forth in SEQ ID NOs: 7 and 8.

In some embodiments, the expression vector is a variant of SEQ ID NO: 20 as set forth in SEQ ID NO: 18 (AGCTTAATGTAGTCTTATGCAATACTCTTGTAGTCTTGCAACATGGTAACGATGA GTTAGCAACATGCCTTACAAGGAGAGAAAAAGCACCGTGCATGCCGATTGGTGG AAGTAAGGTGGTACGATCGTGCCTTATTAGGAAGGCAACAGACGGGTCTGACAT GGATTGGACGAACCACTGAATTGCCGCATTGCAGAGATATTGTATTTAAGTGCCT AGCTCGATACAATAAACGGGTCTCTCTGGTTAGACCAGATCTGAGCCTGGGAGC TCTCTGGCTAACTAGGGAACCCACTGCTTAAGCCT CAATAAAGCTTGCCCTTGAGT GCTTCAAGTAGTGTGTGCCGTCTGTTGTGTGACTCTGGTAACTAGAGATCCCTC AGACCCTTTTAGTCAGTGTGGAAAATCTCTAGCAGTGGCGCCCGAACAGGGACTTGAAAGCGAAAGGGAAACCAGAGGAGCTCTCTCGACGCAGGACTCGGCTTGCTGAAGCGCGCACGGCAAGAGGCGAGGGGCGGCGACTGGTGAGTACGCCAAAAATT TTGACTAGCGGAGGCTAGAAGGAGAGAGATGGGTGCGAGAGCGTCAGTATTAA GCGGGGAGAATTAGATCGCGATGGGAAAAAATTCGGTTAAGGCCAGGGGGAAAGAAAAAATATAAATTAAAACATATAGTATGGGCAAGCAGGGAGCTAGAACGATTCGCAGTTAATCCTGGCCTGTTAGAAACATCAGAAGGCTGTAGACAAATACTG GGACAGCTACAACCATCCCTTCAGACAGGATCAGAAGAACTTAGATCATTATATAATACAGTAGCAACCCTCTATTGTGTGCATCAAAGGATAGAGATAAAAGACACC AAGGAAGCTTTAGACAAGATAGAGGAAGAGCAAAACAAAAGTAAGACCACCGCACAGCAAGCGGCCGCTGATCTTCAGACCTGGAGGAGGGAGATATGAGGGACAATT GGAGAAGTGAATTATATAAATATAAAGTAGTAAAAATTGAACCATTAGGAGTAGCACCCACCAAGGCAAAGAGAAGAGTGGTGCAGAGAGAAAAAAGAGCAGTGGGA ATAGGAGCTTTGTTCCTTGGGTTCTTGGGAGCAGCAGGAAGCACTATGGGCGCA GCCTCAATGACGCTGACGGTACAGGCCAGACAATTATTGTCTGGTATAGTGCAG CAGCAGAACAATTTGCTGAGGGCTATTGAGGCGCAACAGCATCTGTTGCAACTC ACAGTCTGGGGCATCAAGCAGCTCCAGGCAAGAATCCTGGCTGTGGAAAGATACCTAAAGGATCAACAGCTCCTGGGGATTTGGGGTTGCTCTGGAAAACTCATTTGCACCACTGCTGTGCCTTGGAATGCTAGTTGAGTAATAAATCTCTGGAACAGATTTG GAATCACACGACCTGGATGGAGTGGGACAGAGAAATTAACAATTACACAAGCTTAATACACTCCTTAATTGAAGAATCGCAAAACCAGCAAGAAAAGAATGAACAAG AATTATTGGAATTAGATAAATGGGCAAGTTTGTGGAATTGGTTTAACATAACAA ATTGGCTGTGGTATATAAAATTATTCATAATGATAGTAGGAGGCTTGGTAGGTTTAAGAATAGTTTTTGCTGTACTTTCTATAGTGAATAGAGTTAGGCAGGGATATTCA CCATTATCGTTTCAGACCCACCTCCCAACCCCGAGGGGACCCGACAGGCCCGAAGGAATAGAAGAAGAAGGTGGAGAGAGAGACAGAGACAGATCCATTCGATTAGT GAACGGATCTCGACGGTATCGGTTAACTTTTAAAAGAAAAGGGGGGATTGGGGGTACAGTGCAGGGGAAAGAATAGTAGACATAATAGCAACAGACATACAAACTA AAGAATTACAAAAACAAATTACAAAAATTCAAAATTTTATCGATCACGAGACTAGCCTCGAGAAGCTTGATATCGAATTCCCACGGGGTTGGACGCGTAGGAACAGAG AAACAGGAGAATATGGGCCAAACAGGATATCTGTGGTAAGCAGTTCCTGCCCCGGCTCAGGGCCAAGAACAGTTGGAACAGCAGAATATGGGCCAAACAGGATATCTGTGGTAAGCAGTTCCTGCCCCGGCTCAGGGC CAAGAACAGATGGTCCCCAGATGCGGTCCCGCCCTCAGCAGTTTCTAGAGAACCATCAGATGTTTCCAGGGTGCCCCAA GGACCTGAAATGACCCTGTGCCTTATTTGAACTAACCAATCAGTTCGCTTCTCGCTTCTGTTCGCGCGCTTCTGCTCCCCGAGCTCTATATAAGCAGAGCTCGTTTAGTG AACCGTCAGATCGCTAGCACCGGTGCCGCCACCATGCCTCTGGGCCTGCTGTGGCTGGGCCTGGCCCTGCTGGGCGCCCTGCACGCCCAGGCCGGCGTGCAGGTGGAGACAATCTCCCCAGGCGACGGACGCACATTCCCTAAGCGGGGCCAGACCTGCGTGG TGCACTATACAGGCATGCTGGAGGATGGCAAGAAGTTTGACAGCTCCCGGGATAGAAACAAGCCATTCAAGTTTATGCTGGGCAAGCAGGAAGTGATCAGAGGCTGGG AGGAGGGCGTGGCCCAGATGTCTGTGGGCCAGAGGGCCAAGCTGACCATC AGCC CAGACTACGCCTATGGAGCAACAGGCCACCCAGGAATCATCCCACCTCACGCCACCCTGGTGTTCGATGTGGAGCTGCTGAAGCTGGGCGAGGGCGGTAGTCAGAACC TTGTGATACCATGGGCCCCAGAAAATCTCACACTTCATAAACTTTCCGAATCACAACTCGAACTCAACTGGAATAACCGGTTCCTGAATCACTGTCTTGAACACCTGGTACAATATCGGACCGACTGGGATCACTCATGGACAGAACAATCTGTGGACTATAGGCACAAATTCTCACTCCCAAGCGTAGACGGCCAAAAAAGATACACTTTTCGCGTA CGATCCCGCTTTAATCCTCTCTGCGGCTCTGCTCAGCACTGGAGTGAATGGTCCCATCCCATTCATTGGGGATCCAACACATCAAAAGAGAACCCCTTTCTGTTCGCATTGGAGGCCGTAGTCATATCTGTTGGATCCATGGGACTTATTATCTCCCTGTTGTGTGTGTACTTCTGGCTGGAACGGACTATGCCCAGGATCCCCACGCTCAAGAATCTG AAGATCTCGTCACAGAATACCATGGTAATTTCAGCGCCTGGAGCGGAGTCTCTAAGGGTCTGGCCGAATCCCTCCAACCCGATTATTCTGAACGGTTGTGCCTCGTAT CCGAAATACCACCAAAAGGCGGGGCTCTGGGTGAGGGCCCAGGGGCGAGTCCGTGCAATCAACACAGCCCGTATTGGGCCCCTCCTTGTTATACGTTGAAGCCCGAAACTGGAAGCGGAGCTACTAACTTCAGCCTGCTGAAGCAGGCTGGAGACGTGGAGGAGAACCCTGGACCTATGGCACTGCCCGTGACCGCCCTGCTGCTGCCTCTGGCCCT GCTGCTGCACGCAGCCCGGCCTATCCTGTGGCACGAGATGTGGCACGAGGGCCTGGAGGAGGCCAGCAGGCTGTATTTTGGCGAGCGCAACGTGAAGGGCATGTTCGAGGTGCTGGAGCCTCTGCACGCCATGATGGAGAGAGGCCCACAGACCCTGAAGGAGACATCCTTTAACCAGGCCTATGGACGGGACCTGATGGAGGCACAGGAGTGGTG CAGAAAGTACATGAAGTCTGGCAATGTGAAGGACCTGCTGCAGGCCTGGGATCTGTACTATCACGTGTTTCGGAGAATCTCCAAGGAGGTTCAAAACCTTTTGAGAAC CTTAGACTGATGGCGCCCATCTCTCTGCAGGTAGTTCACGTTGAGACCCATAGATGCAATATAAGCTGGGAAATCTCACAAGCCAGCCATTACTTTGAACGGCATTTGG AATTCGAGGCCCGAACACTTTCCCCCGGTCATACGTGG GAAGAAGCTCCTCTCTT GACGCTGAAGCAGAAGCAGGAGTGGATTTGTCTG-GAGACTTTGACTCCTGATAC TCAGTATGAGTTC-CAAGTTCGGGTGAAACCACTCCAAGGCGAGTT-CACGACGTG GTCTCCGTGGAGT-CAACCGTTGGCGTTCCGCACGAAGCCCGCTGCCCT TGGCAAA GACACGATTCCGTGGCTTGGG-CATCTGCTCGTTGGGCTGAGTGGTGCGTTTGGTT TCATCATCTTGGTCTATCTCTTGATCAAT-TGCAGAAATACAGGCCCTTGGCTGAA AAAAGTGCTCAAGTGTAATACCCCCGACC-CAAGCAAGTTCTTCTCCCAGCTTTCT TCAGAG-CATGGAGGCGATGTGCAGAAATGGCTCTCTT-CACCTTTTCCCTCCTCAA GCTTCTCCCCGGGAGGGCTGGCGCCCGAGATTT-CACCTCTTGAGGTACTTGAACG AGACAAGGT-TACCCAACTTCTCCTTCAACAGGA-TAAGGTACCCGAACCTGCGAG CCTTAGCTCCAACCACTCTCTTACGAGCTGCTT-CACCAATCAGGGATACTTCTTTT TCCACCTTCCC-GATGCGCTGGAAATCGAAGCTTGTCAAGTTTACTT-TACCTATGA TCCATATAGCGAGGAA-GATCCCGACGAAGGAGTCGCCGGTGCGCC-CACGGGTTC CTCACCC-CAACCTCTCCAGCCTCTCTCAGGAGAAGATGATG CTTATTGCACTTTT CCCAGTAGAGAC-GATCTCCTCCTCTTTTCTC-CATCTCTTTTGGGGGGACCTTCCCC CCCTTC-TACGGCACCTGGCGGGTCTGGTGCTGGCGAGGA GCGGATGCCGCCGTC CCTCCAGGAGCGAGTAC-CACGAGATTGGGATCCCCAGCCACTTGGACCCCC-CAC CCCCGGCGTACCTGACCTTGTCGATTTT-CAACCTCCCCCTGAATTGGTGCTGCGA GAGGCTGGGGAG-GAAGTTCCGGACGCTGGGCCGAGG-GAGGGCGTGTCCTTTCCA TGGAGTAGGCCTCCAGGTCAAGGCGAGTT-TAGGGCTCTCAACGCGCGGCTGCCG TTGAATACA-GACGCTTATCTCTCACTGCAG-GAACTGCAAGGTCAGGACCCAACA CATCTTGTAGGATCTGGTGCTACTAAT-TTTTCTCTTTTGAAGCAAGCTGGAGATGT TGAAGAGAACCCTGGTCCAGT-GAGCAAGGGCGAGGAGCTGTTCACCGGGGTGGT GCC-CATCCTGGTCGAGCTGGACGGCGACGTAAACGGC-CACAAGTTCAGCGTGTC CGGCGAGGGCGAGGGC-GATGCCACCTACGGCAAGCTGACCCTGAAGTTCA TCTG CACCACCGGCAAGCTGCCCGTGCCCTGGCC-CACCCTCGTGACCACCCTGACCTAC GGCGTGCAGTGCTTCAGCCGCTACCCCGACCACAT-GAAGCAGCACGACTTCTTC AAGTCCGC-CATGCCCGAAGGCTACGTCCAGGAGCGCAC-CATCTTCTTCAAGGAC GACGGCAACTACAAGACCCGCGCCGAGGT-GAAGTTCGAGGGCGACACCCTGGTG AACCG-CATCGAGCTGAAGGGCATCGACTT-CAAGGAGGACGGCAACATCCTGGGG CACAAGCTGGAGTACAACTACAACAGC-CACAACGTCTATATCATGGCCGACAAG CAGAAGAACGGCATCAAGGTGAACTTCAA-GATCCGCCACAACATCGAGGACGG CAGCGTGCAGCTCGCCGACCAC-TACCAGCAGAACACCCCCATCGGCGACGGCCC CGTGCTGCTGCCCGACAACCACTACCT- GAGCACCCAGTCCGCCCTGAGCAAAGA CCC-CAACGAGAAGCGCGATCACATGGTCCTGCTG-GAGTTCGTGACCGCCGCCGG GATCACTCTCGGCATGGACGAGCTGTA-CAAGTAAACTAGTGTCGACAATCAACC TCTGGAT-TACAAAATTTGTGAAAGATTGACTGGTATTCT-TAACTATGTTGCTCCTT TTACGCTATGTGGATACGCTGCTT-TAATGCCTTTGTATCATGCTATTGCTTCCCGT ATGGCTTTCAT-TTTCTCCTCCTTGTATAAATCCTGGTTGCTGTCTCTT-TATGAGGA GTTGTGGCCCGTTGTCAGGCAACGTGGCGTGGT GTGCACTGTGTTTGCTGACGCA ACCCC-CACTGGTTGGGGCATTGCCAC-CACCTGTCAGCTCCTTTCCGGGACTTTCG CTTTCCCCCTCCCTATTGCCACGGCGGAACT-CATCGCCGCCTGCCTTGCCCGCTG CTGGACAGGGGCTCGGCTGTTGGGCACTGACAAT-TCCGTGGTGTTGTCGGGGAA GCTGACGTCCTTTC-CATGGCTGCTCGCCTGTGTTGCCACCTGGAT-TCTGCGCGGG ACGTCCTTCTGCTACGTCCCTTCGGCCCT-CAATCCAGCGGACCTTCCTTCCCGCG GCCTGCTGCCGGCTCTGCGGCCTCTTCCGCGTCTT CGCCTTCGCCCTCAGACGAG TCG-GATCTCCCTTTGGGCCGCCTCCCCGCCTGGAAT-TCGAGCTCGGTACCTTTAA GACCAATGACTTA-CAAGGCAGCTGTAGATCTTAGCCACTTTTTAAAAG AAAAGG GGGGACTGGAAGGGCTAATTCACTCC-CAACGAAGACAAGATCTGCTTTTTGCTTG TACTGGGTCTCTCTGGTTAGACCAGATCT-GAGCCTGGGAGCTCTCTGGCTAACTA GGGAACC-CACTGCTTAAGCCTCAATAAAGCTTGCCTT-GAGTGCTTCAAGTAGTGT GTGCCCGTCTGTTGTGTGACTCTGGTAACTAGAG ATCCCTCAGACCCTTTTAGTC AGTGTG-GAAAATCTCTAGCAGTAGTAGTTCATGTCATCTTAT-TATTCAGTATTTAT AACTTGCAAAGAAAT-GAATATCAGAGAGTGAGAGGAACTTGTTTATTGCA GCTT ATAATGGTTACAAATAAAGCAATAGCAT-CACAAATTTCACAAATAAAGCATTTTT TTCACTG-CATTCTAGTTGTGGTTTGTCCAAACTCAT-CAATGTATCTTATCATGTCT GGCTCTAGC-TATCCCGCCCCTAACTCCGCCCAGTTCCGCCCAT-TCTCCGCCCCAT GGCTGACTAATTTTTTTTATT-TATGCAGAGGCCGAGGCCGCCTCGGCCTCTGAGC TATTCCAGAAGTAGTGAGGAGGCTTTTTTG-GAGGCCTAGGCTTTTGCGTCGAGAC GTACCCAAT-TCGCCCTATAGTGAGTCGTATTACGCGCGCT-CACTGGCCGTCGTTT TACAACGTCGTGACTGGGAAAACCCTGGCGT-TACCCAACTTAATCGCCTTGCAGC ACATCCCCCTTTCGCCAGCTGGCGTAATAGCGAA GAGGCCCGCACCGATCGCCC TTCC-CAACAGTTGCGCAGCCT-GAATGGCGAATGGCGCGACGCGCCCTGTAGCGG CGCATTAAGCGCGGCGGGTGTGGTG-TACGCGCAGCGTGACCGCTACACTTGC CAGCGCCCTAGCGCCCGCTCCTTTCGCTTTCTTCC CTTCCTTTCTCGCCACGTTCG CCGGCTTTCCCCGT-CAAGCTCTAAATCGGGGGCTCCCTTTAGGGTTCC-GATTTAG TGCTTTACGGCACCTCGACCC-CAAAAAACTTGATTAGGGTGATGGTTCACGTAGT GGGCCATCGCCCTGATA-GACGGTTTTTCGCCCTTTGACGTTGGAGTC- CACGTTCTTTAATAGTGGACTCTTGTTCCAAACTGGAACAACACTCAACCCTATCTCGGTCTA TTCTTTTGATTTATAAGGGATTTTGCCGATTTCGGCCTATTGGTTAAAAAATGAGC TGATTTAACAAAAATTTAACGCGAATTTTAACAAAATATTAACGTTTACAATTTC CCAGGTGGCACTTTTCGGGGAAATGTGCGCGGAACCCCTATTTGTTTATTTTTCT AAATACATTCAAATATGTATCCGCTCATGAGACAATAACCCTGATAAATGCTTCA ATAATATTGAAAAAGGAAGAGTATGAGTATTCAACATTTCCGTGTCGCCCTTATT CCCTTTTTTGCGGCATTTTGCCTTCCTGTTTTTGCTCACCCAGAAACGCTGGTGAA AGTAAAAGATGCTGAAGATCAGTTGGGTGCACGAGTGGGTTACATCGAACTGGA TCTCAACAGCGGTAAGATCCTTGAGAGTTTTCGCCCCGAAGAACGTTTTCCAATG ATGAGCACTTTTAAAGTTCTGCTATGTGGCGCGGTATTATCCCGTATTGACGCCG GCAAGAGCAACTCGGTCGCCGCATACACTATTCTCAGAATGACTTGGTTGAGT ACTCACCAGTCACAGAAAAGCATCTTACGGATGGCATGACAGTAAGAGAATTAT GCAGTGCTGCCATAACCATGAGTGATAACACTGCGGCCAACTTACTTCTGACAA CGATCGGAGGACCGAAGGAGCTAACCGCTTTTTTGCACAACATGGGGGATCATG TAACTCGCCTTGATCGTTGGGAACCGGAGCTGAATGAAGCCATACCAAACGACG AGCGTGACACCACGATGCCTGTAGCAATGGCAACAACGTTGCGCAAACTATTAA CTGGCGAACTACTTACTCTAGCTTCCCGGCAACAATTAATAGACTGGATGGAGGC GGATAAAGTTGCAGGACCACTTCTGCGCTCGGCCCTTCCGGCTGGCTGGTTT ATT GCTGATAAATCTGGAGCCGGTGAGCGTGGGTCTCGCGGTATCATTGCAGCACTG GGGCCAGATGGTAAGCCCTCCCGTATCGTAGTTATCTACACGACGGGGAGTCAG GCAACTATGGATGAACGAAATAGACAGATCGCTGAGATAGGTGCCTCACTGATT AAGCATTGGTAACTGTCAGACCAAGTTTACTCATATATACTTTAGATTGATTTAA AACTTCATTTTTAATTTAAAAGGATCTAGGTGAAGATCCTTTTTGATAATCTCATG ACCAAAATCCCTTAACGTGAGTTTTCGTTCCACTGAGCGTCAGACCCCGTAGAAA AGATCAAAGGATCTTCTTGAGATCCTTTTTTTCTGCGCGTAATCTGCTGCTTG CAA ACAAAAAAACCACCGCTACCAGCGGTGGTTTGTTTGCCGGATCAAGAGCTACCA ACTCTTTTTCCGAAGGTAACTGGCTTCAGCAGAGCGCAGATACCAAATACTGTCC TTCTAGTGTAGCCGTAGTTAGGCCACCACTTCAAGAACTCTGTAGCACCGCCTAC ATACCTCGCTCTGCTAATCCTGTTACCAGTGGCTGCTGCCAGTGGCGATAAGTCG TGTCTTACCGGGTTGGACTCAAGACGATAGTTACCGGATAAGGCGCAGCGGTCG GGCTGAACGGGGGGTTCGTGCACACAGCCCAGCTTGGAGCGAACGACCTACACC GAACTGAGATACCTACAGCGTGAGCTATGAGAAAGCGCCACGCTTCCCGAAGGG AGAAAGGCGGACAGGTATCCGGTAAGCGGCAGG GTCGGAACAGGAGAGCGCAC GAGGGAGCTTCCAGGGGGAAACGCCTGGTATCTTTATAGTCCTGTCGGGTTTCGC CACCTCTGACTTGAGCGTCGATTTTTGTGATGCTCGTCAGGGGGGCG GAGCCTAT GGAAAAACGCCAGCAACGCGGCCTTTTTACGGTTCCTGGCCTTTTGCTGGCCTTT TGCTCACATGTTCTTTCCTGCGTTATCCCCTGATTCTGTGGATAACCGTATTACCG CCTTTGAGTGAGCTGATACCGCTCGCCGCAGCCGAACGACCGAGCGCAG CGAGT CAGTGAGCGAGGAAGCGGAAGAGCGCCCAATACGCAAACCGCCTCTCCCCGCGC GTTGGCCGATTCATTAATGCAGCTGGCACGACAGGTTTCCCGACTGGA AAGCGG GCAGTGAGCGCAACGCAATTAATGTGAGTTAGCTCACTCATTAGGCACCCCAGG CTTTACACTTTATGCTTCCGGCTCGTATGTTGTGTGGAATTGTGAGCGGATAACA ATTTCACACAGGAAACAGCTATGACCATGATTACGCCAAGCGCGCAATTAACCC TCACTAAAGGGAACAAAAGCTGGAGCTGCA; SEQ ID NO: 18). SEQ ID NO: 18 encodes the protein sequences as set forth in SEQ ID NOs: 3 and 4.

In some embodiments, the expression vector is a variant of SEQ ID NO: 20 as set forth in SEQ ID NO: 19 (AGCTTAATGTAGTCTTATGCAATACTCTTGTAGTCTTGCAACATGGTAACGATGA GTTAGCAACATGCCTTACAAGGAGAGAAAAAGCACCGTGCATGCCGATTGG TGG AAGTAAGGTGGTACGATCGTGCCTTATTAGGAAGGCAACAGACGGGTCTGACAT GGATTGGACGAACCACTGAATTGCCGCATTGCAGAGATATTGTATTTAAGTGCCT AGCTCGATACAATAAACGGGTCTCTCTGGTTAGACCAGATCTGAGCCTGGGAGC TCTCTGGCTAACTAGGGAACCCACTGCTTAAGCCTCAATAAAGCTTGCCTTGAGT GCTTCAAGTAGTGTGTGCCCGTCTGTTGTGTGACTCTGG TAACTAGAGATCCCTC AGACCCTTTTAGTCAGTGTGGAAAATCTCTAGCAGTGGCGCCCGAACAGGGACT TGAAAGCGAAAGGGAAACCAGAGGAGCTCTCTCGACGCAGGACTCGGCTTGCTG AAGCGCGCACGGCAAGAGGCGAGGGGCGGCGAC TGGTGAGTACGCCAAAAATT TTGACTAGCGGAGGCTAGAAGGAGAGAGATGGGTGCGAGAGCG TCAGTATTAA GCGGGGGAGAATTAGATCGCGATGGGAAAAAATTCGGTTAAGGCCAGGGGGAA AGAAAAAATATAAATTAAAACATATAGTATGGGCAAGCAGGGAGCTAGAACGA TTCGCAGTTAATCCTGGCCTGTTAGAAACATCAGAAGGCTGTAGACAAATACTG GGACAGCTACAACCATCCCTTCAGACAGGATCAGAAGAACTTAGATCATTATAT AATACAGTAGCAACCCTCTATTGTGTGCATCAAAGGATAGAGATAAAAGACACC AAGGAAGCTTTAGACAAGATAGAGGAAGAGCAAAACAAAAGTAAGACCACCGC ACAGCAAGCGGCCGCTGATCTTCAGACCTGGAGGAGGAGATATGAGGGACAATT GGAGAAGTGAATTATATAAATATAAAGTAGTAAAAATTGAACCATTAGGAGTAG CACCCACCAAGGCAAAGAGAAGAGTGGTGCAGAGAGAAAA AAGAGCAGTGGGA ATAGGAGCTTTGTTCCTTGGGTTCTTGGGAGCAGCAGGAAGCACTATGGGCGCA GCCTCAATGACGCTGACGGTACAGGCCAGACAATTATTGTCTGGTATAGTGCAG CAGCAGAACAATTTGCTGAGGGCTATTGAGGCGCAACAGCATCTGTTGCAACTC ACAGTCTGGGGCATCAAGCAGCTCCAGGCAAGAATCCTGGCTGTGGAAAGATAC CTAAAGGATCAACAGCTCCTGGGGATTTGGGGTTGCTCTGGAAAACTCATTTGCA CCACTGCTGTGCCTTGGAATGCTAGTTGGAGTAATAAATCTCTGGAACAGATTTG GAATCACACGACCTGGATGGAGTGGGACAGAGAAATTAACAATTACACAAGCTT AATACACTCCTTAATTGAAGAATCGCAAAACCAGCAAGAAAAGAATGAACAAG AATTATTGGAATTAGATAAATGGGCAAGTTTGTGGAATTGGTTTAACATAACAA ATTGGCTGTGGTATATAAAATTATTCATAATGATAGTAGGAGGCTTGGTAGGTTT AAGAATAGTTTTTGCTGTACTTTCTATAGTGAATAGAGTTAGGCAGGGATATTCA CCATTATCGTTTCAGACCCACCTCCCAACCCCGAGGGGACCCGACAGGCCCGAA GGAATAGAAGAAGGTGGAGAGAGAGACAGAGACAGATCCATTCGATTAGT GAACGGATCTCGACGGTATCGGTTAACTTTTAAAAGAAAAGGGGGGATTGGGGG GTACAGTGCAGGGGAAAGAATAGTAGACATAATAGCAACAGACATACAAACTA AAGAATTACAAAAACAAATTACAAAAATTCAAAATTTTATCGATCACGAGACTA GCCTCGAGAAGCTTGATATCGAATTCCCACGGGGTTGGACGCGTAGGAACAGAG AAACAGGAGAATATGGGCCAAACAGGATATCTGTGGTAAGCAGTTCCTGCCCCG GCTCAGGGCCAAGAACAGTTGGAACAGCAGAATATGGGCCAAACAGGATATCTG TGGTAAGCAGTTCCTGCCCCGGCTCAGGGCCAAGAACAGATGGTCCCCAGATGC GGTCCCGCCCTCAGCAGTTTCTAGAGAACCATCAGATGTTTCCAGGGTGCCCCAA GGACCTGAAATGACCCTGTGCCTTATTTGAACTAACCAATCAGTTCGCTTCTGC TTCTGTTCGCGCGCTTCTGCTCCCCGAGCTCTATATAAGCAGAGCTCGTTTAGTG AACCGTCAGATCGCTAGCACCGGTGCCGCCACCATGCCTCTGGGCCTGCTGTGGC TGGGCCTGGCCCTGCTGGGCGCCCTGCACGCCCA GGCCGGCGTGCAGGTGGAGA CAATCTCCCCAGGCGACGGACGCACATTCCCTAAGCGGGGCCAGACCTGCGTGG TGCACTATACAGGCATGCTGGAGGATGGCAAGAAGTTTGACAGCTCCCGGGATA GAAACAAGCCATTCAAGTTTATGCTGGGCAAGCAGGAAGTGATCAGAGGCTGGG AGGAGGGCGTGGCCCAGATGTCTGTGGGCCAGAGGGCCAAGCTGACCATCAGCC CAGACTACGCCTATGGAGCAACAGGCCACCCAGGAATCATCCCACCTCACGCCA CCCTGGTGTTCGATGTGGAGCTGCTGAAGCTGGGCGAGCAAAACTTGGTGATTCC TTGGGCCCCAGAAAATCTCACGCTTCACAAGTTGTCCGAATCCCAGCTCGAGCTC AACTGGAATAATAGATTTCTTAATCATTGTTTGAACACCTGGTTCAATATAGAA CGGATTGGGACCACTCATGGACCGAGCAGTCAGTTGACTACCGCCACAAATTTT CACTTCCCAGCGTAGATGGGCAGAAGAGGTACACATTTAGGGTCAGATCCAGGT TTAATCCTCTGTGTGGTTCTGCTCAACACTGGTCTGAGTGGAGCCATCCGATCCA CTGGGGCTCAAATACCTCTAAAGAAAATCCGTTCCTCTTTGCG CTCGAAGCCGTT GTTATCAGCGTCGAAGCATGGGACTTATCATTTCCCTTCTCTGCGTGTACTTCTG GCTGGAGCGGACGATGCCGCGGATTCCGACGCTCAAAAACCTGGAGGACCTTGT AACAGAATATCACGGTAATTTCTCCGCTTGGAGTGGCGTATCAAAGGGGCTTGCT GAGTCCCTTCAACCGGATTACTCTGAGCGCCTCTGCTTGGTGTCCAGATACCTC CCAAAGGAGGTGCACTTGGGGAGGGGCCAGGCGCGTCCCCTTGCAATCAGCATA GTCCGTATTGGGCGCCCCCTGTTATACCCTCAAACCGGAAACGGGAAGCGGAG CTACTAACTTCAGCCTGCTGAAGCAGGCTGGAGACGTGGAGGAGAACCCTGGAC CTATGGCACTGCCCGTGACCGCCCTGCTGCTGCCT CTGGCCCTGCTGCTGCACGC AGCCCGGCCTATCCTGTGGCACGAGATGTGGCACGAGGGCCTGGAGGAGGCCAG CAGGCTGTATTTTGGCGAGCGCAACGTGAAGGGCATGTTCGAGGTGCTGGAGCC TCTGCACGCCATGATGGAGAGAGGCCCACAGACCCTGAAGGAGACATCCTTTAA CCAGGCCTATGGACGGGACCTGATGGAGGCACAGGAGTGGTGCAGAAAGTACAT GAAGTCTGGCAATGTGAAGGACCTGCTGCAGGCCTGGGATCTGTACTATCACGT GTTTCGGAGAATCTCCAAGAAACCTTTTGAGAACCTTAGACTGATGGCGCCCATC TCTCTGCAGGTAGTTCACGTTGAGACCCATAGATGCAATATAAGCTGGGAAATCT CACAAGCCAGCCATTACTTTGAACGGCATTTGGAATTCGAGGCCCGAACACTTTC CCCCGGTCATACGTGGGAAGAAGCTCCTCTCTTGACGCTGAAGCAGAAGCAGGA GTGGATTTGTCTGGAGACTTTGACTCCTGATACTCAGTATGAGTTCCAAGTTCGG GTGAAACCACTCCAAGGCGAGTTCACGACGTGGTCTCCGTGGAGTCAACCGTTG GCGTTCCGCACGAAGCCCGCTGCCCTTGGCAAAGACACGATTCCGTGGCTTGGG CATCTGCTCGTTGGGCTGAGTGGTGCGTTTGGTTTCATCATCTTGGTCTATCTCTT GATCAATTGCAGAAATACAGGCCCTTGGCTGAAAAAAGTGCTCAAGTGTAATAC CCCCGACCCAAGCAAGTTCTTCTCCCAGCTTTCTTCAGAGCATGGAGGCGATGTG CAGAAATGGCTCTCTTCACCTTTTCCCTCCTCAAGCTTCTCCCGGGAGGGCTGG CGCCCGAGATTTCACCTCTTGAGGTACTTGAACGAGACAAGGTTACCCAACTTCT CCTTCAACAGGATAAGGTACCCGAACCTGCAGCCTTAGCTCCAACCACTCTCTT ACGAGCTGCTTCACCAATCAGGGATACTTCTTTTTCCACCTTCCCGATGCGCTGG AAATCGAAGCTTGTCAAGTTTACTTTACCTATGATCCATATAGCGAGGAAGATCC CGACGAAGGAGTCGCCGGTGCGCCCACGGGTTCCTCACCCCAACCTCTCCAGCC TCTCTCAGGAGAAGATGATGCTTATTGCACTTTTCCCAGTAGAGACGATCTCCTC CTCTTTTCTCCATCTCTTTTGGGGGGACCTTCCCCCCCTTCTACGGCACCTGGCGG GTCTGGTGCTGGCGAGGAGCGGATGCCGCCGTCCCTCCAGGAGCGAGTAC CACG AGATTGGGATCCCCAGCCACTTGGACCCCCCACCCCCGGCGTACCTGACCTTGTC GATTTTCAACCTCCCCCTGAATTGGTGCTGCGAGAGGCTGGGGAGGAAGTTCCGGACGCTGGGCCGAGGGAGGGCGTGTCCTTTCCATGGAGTAGGCCTCCAGGTCAA GGCGAGTTTAGGGCTCTCAACGCGCGGCTGCCGTTGAATACAGACGCTTATCTCT CACTGCAGGAACTGCAAGGTCAGGACCCAACACATCTTGTAGGATCTGGTGCTA CTAATTTTTCTCTTTTGAAGCAAGCTGGAGATGTTGAAGAGAACCCTGGTCCAGT GAGCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATG CCACCTACGGCAAGCTGACCCTGAAGTTCATCTGCACCACCGGCAAGCTGCCCG TGCCCTGGCCCACCCTCGTGACCACCCTGACCTACGGCGTGCAGTGCTTCAGCCG CTACCCCGACCACATGAAGCAGCACGACTTCTTCAAGTCCGCCATGCCCGAAGG CTACGTCCAGGAGCGCACCATCTTCTTCAAGGACGACGGCAACTACAAGACCCG CGCCGAGGTGAAGTTCGAGGGCGACACCCTGGTGAACCGCATCGAGCTGAAGGG CATCGACTTCAAGGAGGACGGCAACATCCTGGGGCACAAGCTGGAGTACAACTA CAACAGCCACAACGTCTATATCATGGCCGACAAGCAGAAGAACGGCATCAAGGT GAACTTCAAGATCCGCCACAACATCGAGGACGGCAGCGTGCAGCTCGCCGACCA CTACCAGCAGAACACCCCCATCGGCGACGGCCCCGTGCTGCTGCCCGACAACCA CTACCTGAGCACCCAGTCCGCCCTGAGCAAAGACCCCAACGAGAAGCGCGATCA CATGGTCCTGCTGGAGTTCGTGACCGCCGCCGGGATCACTCTCGGCATGGACGA GCTGTACAAGTAAACTAGTGTCGACAATCAACCTCTGGATTACAAAATTTGTGAA AGATTGACTGGTATTCTTAACTATGTTGCTCCTTTTACGCTATGTGGATACGCTG TTTAATGCCTTTGTATCATGCTATTGCTTCCCGTATGGCTTTCATTTTCTCCTCCTT GTATAAATCCTGGTTGCTGTCTCTTTATGAGGAGTTGTGGCCCGTTGTCAGGCAA CGTGGCGTGGTGTGCACTGTGTTTGCTGACGCAACCCCCACTGGTTGGGGCATTG CCACCACCTGTCAGCTCCTTTCCGGGACTTTCGCTTTCCCCTCCCTATTGCCACG GCGGAACTCATCGCCGCCTGCCTTGCCCGCTGCTGGACAGGGGCTCGGCTGTTGG GCACTGACAATTCCGTGGTGTTGTCGGGGAAGCTGACGTCCTTTCCATGGCTGCT CGCCTGTGTTGCCACCTGGATTCTGCGCGGGACGTCCTTCTGCTACGTCCCTTCG GCCCTCAATCCAGCGGACCTTCCTTCCCGCGGCCTGCTGCCGGCTCTGCGGCCTC TTCCGCGTCTTCGCCTTCGCCCTCAGACGAGTCGGATCTCCCTTTGGGCCGCCTCC CCGCCTGGAATTCGAGCTCGGTACCTTTAAGACCAATGACTTACAAGGCAGCTGT AGATCTTAGCCACTTTTTAAAAGAAAAGGGGGGACTGGAAGGGCTAATTCACTC CCAACGAAGACAAGATCTGCTTTTTGCTTGTACTGGGTCTCTCTGGTTAGACCAG ATCTGAGCCTGG- GAGCTCTCTGGCTAACTAGGGAACCCACTGCTTAAGCCTCAAT AAAGCTTGCCTTGAGTGCTTCAAGTAGTGTGTGCCCGTCTGTTGTGTGACTCTGG TAACTAGAGATCCCTCAGACCCTTTTAGTCAGTGTGGAAAATCTCTAGCAGTAGT AGTTCATGTCATCTTATTATTCAGTATTTATAACTTGCAAAGAAATGAATATCAG AGAGTGAGAGGAACTTGTTTATTGCAGCTTATAATGGTTACAAATAAAGCAATA GCATCACAAATTTCACAAATAAAGCATTTTTTTCACTGCATTCTAGTTGTGGTTTG TCCAAACTCATCAATGTATCTTATCATGTCTGGCTCTAGCTATCCCGCCCCTAACT CCGCCCAGTTCCGCCCATTCTCCGCCCCATGGCTGACTAATTTTTTTTATTTATGC AGAGGCCGAGGCCGCCTCGGCCTCTGAGCTATTCCAGAAGTAGTGAGGAGGCTT TTTTGGAGGCCTAGGCTTTTGCGTCGAGACGTACCCAATTCGCCCTATAGTGAGT CGTATTACGCGCGCTCACTGGCCGTCGTTTTACAACGTCGTGACTGGGAAAACCC TGGCGTTACCCAACTTAATCGCCTTGCAGCACATCCCCCTTTCGCCAGCTGGCGT AATAGCGAAGAGGCCCGCACCGATCGCCCTTCCCAACAGTTGCGCAGCCTGAAT GGCGAATGGCGCGACGCGCCCTGTAGCGGCGCATTAAGCGCGGCGGGTGTGGTG GTTACGCGCAGCGTGACCGCTACACTTGCCAGCGCCCTAGCGCCCGCTCCTTTCG CTTTCTTCCCTTCCTTTCTCGCCACGTTCGCCGGCTTTCCCCGTCAAGCTCTAAAT CGGGGGCTCCCTTTAGGGTTCCGATTTAGTGCTTTACGGCACCTCGACCCCAAAA AACTTGATTAGGGTGATGGTTCACGTAGTGGGCCATCGCCCTGATAGACGGTTTT TCGCCCTTTGACGTTGGAGTCCACGTTCTTTAATAGTGGACTCTTGTTCCAAACTG GAACAACACTCAACCCTATCTCGGTCTATTCTTTTGATTTATAAGGGATTTTGCCG ATTTCGGCCTATTGGTTAAAAAATGAGCTGATTTAACAAAAATTTAACGCGAATT TTAACAAAATATTAACGTTTACAATTTCCCAGGTGGCACTTTTCGGGGAAATGTG CGCGGAACCCCTATTTGTTTATTTTTCTAAATACATTCAAATATGTATCCGCTCAT GAGACAATAACCCTGATAAATGCTTCAATAATATTGAAAAAGGAAGAGTATGAG TATTCAACATTTCCGTGTCGCCCTTATTCCCTTTTTTGCGGCATTTTGCCTTCCTGT TTTTGCTCACCCAGAAACGCTGGTGAAAGTAAAAGATGCTGAAGATCAGTTGGG TGCACGAGTGGGTTACATCGAACTGGATCTCAACAGCGGTAAGATCCTTGAGAG TTTTCGCCCCGAAGAACGTTTTCCAATGATGAGCACTTTTAAAGTTCTGCTATGT GGCGCGGTATTATCCCGTATTGACGCCGGGCAAGAGCAACTCGGTCGCCGCATA CACTATTCTCAGAATGACTTGGTTGAGTACTCACCAGTCACAGAAAAGCATCTTA CGGATGGCATGACAGTAAGAGAATTATGCAGTGCTGCCATAACCATGAGTGATA ACACTGCGGCCAACTTACTTCTGACAACGATCGGAGGACCGAAGGAGCTAACCG CTTTTTTGCACAACATGGGGGATCATGTAACTCGCCTTGATCGTTGGGAACCGGA GCTGAATGAAGCCATACCAAACGACGAGCGTGACACCAC- GATGCCTGTAGCAAT GGCAACAACGTTGCGCAAACTAT- TAACTGGCGAACTACTTACTCTAGCTTCCCGG CAACAATTAATAGACTGGATGGAGGCGGA- TAAAGTTGCAGGACCACTTCTGCGC TCGGCCCTTCCGGCTGGCTGGTTTATTGCTGA- TAAATCTGGAGCCGGTGAGCGTG GGTCTCGCGGTATCATTGCAGCACTGGGGCCA- GATGGTAAGCCCTCCCGTATCGT AGTTATCTA- CACGACGGGGAGTCAGGCAACTATGGAT- GAACGAAATAGACAGAT CGCTGAGATAGGTGCCTCACTGATTAAGCAT- TGGTAACTGTCAGACCAAGTTTAC TCATATATACTT- TAGATTGATTTAAAACTTCATTTTTAATT- TAAAAGGATCTAGGT GAAGATCCTTTTTGATAATCTCATGAC- CAAAATCCCTTAACGTGAGTTTTCGTTCC ACT- GAGCGTCAGACCCCGTAGAAAAGAT- CAAAGGATCTTCTTGAGATCCTTTTTT TCTGCGCGTAATCTGCTGCTTGCAAACAAAAAAAC- CACCGCTACCAGCGGTGGT TTGTTTGCCGGAT- CAAGAGCTAC- CAACTCTTTTTCCGAAGGTAACTGGCTTCAGC AGAGCGCAGATAC- CAAATACTGTCCTTCTAGTGTAGCCGTAGTTAGGC- CACCACT TCAAGAACTCTGTAGCACCGCCTACAT- ACCTCGCTCTGCTAATCCTGTTACCAGT GGCTGCTGCCAGTGGCGATAAGTCGTGTCT- TACCGGGTTGGACTCAAGACGATA GTTACCGGA- TAAGGCGCAGCGGTCGGGCT- GAACGGGGGGTTCGTGCACACAGCC CAGCTTGGAGCGAACGACCTACACCGAACTGAGA- TACCTACAGCGTGAGCTATG AGAAAGCGC- CACGCTTCCCGAAGG- GAGAAAGGCGGACAGGTATCCGGTAAGCG GCAGGGTCGGAACAGGAGAGCGCACGAGG- GAGCTTCCAGGGGGAAACGCCTGG TATCTT- TATAGTCCTGTCGGGTTTCGCCACCTCTGACTT- GAGCGTCGATTTTTGTG ATGCTCGTCAGGGGGCGGAGCCTATG- GAAAAACGCCAGCAACGCGGCCTTTTT ACGGTTCCTGGCCTTTTGCTGGCCTTTTGCTCA- CATGTTCTTTCCTGCGTTATCCC CTGATTCTGTGGA- TAACCGTATTACCGCCTTTGAGTGAGCTGA- TACCGCTCGCCG CAGCCGAACGACCGAGCGCAGCGAGTCAGT- GAGCGAGGAAGCGGAAGAGCGCC CAATACGCAAACCGCCTCTCCCCGCGCGTTGGCC- GATTCATTAATGCAGCTGGCA CGACAGGTTTCCCGACTGGAAAGCGGGCAGT- GAGCGCAACGCAATTAATGTGAG TTAGCTCACT- CATTAGGCACCCCAGGCTTTACACTT- TATGCTTCCGGCTCGTATGT TGTGTGGAATTGTGAGCGGATAACAATTT- CACACAGGAAACAGCTATGACCATG ATTACGC- CAAGCGCGCAATTAACCCTCACTAAAGG- GAACAAAAGCTGGAGCTGC A; SEQ ID NO: 19). SEQ ID NO: 19 encodes the protein sequences as set forth in SEQ ID NOs: 5 and 6.

In some embodiments, the expression vector includes a nucleic acid having at least 80%, 85%, 90%, 95%, 98% or 99% nucleic acid sequence identity (or a percentage nucleic acid sequence identity within a range defined by any two of the aforementioned percentages) with the nucleotide sequences provided herein, or a specifically derived fragment thereof. In some embodiments, the expression vector comprises a promoter. In some embodiments, the expression vector comprises the nucleic acid encoding a fusion protein. In some embodiments, the vector is RNA or DNA.

Cells and Compositions: T Lymphocyte Populations

The compositions described herein provide for genetically modified cells, such as mammalian cells, which include the protein sequences or the expression vectors as set forth and described herein. Accordingly, provided herein are cells, such as mammalian cells, for dimeric CISC secretion, wherein the cell comprises the protein sequences of anyone of the embodiments described herein or the expression vector of anyone of the embodiments described herein. In some embodiments, the cell is a bacterial cell or a mammalian cell, such as a lymphocyte. In some embodiments, the cell is E. coli. In some embodiments, the cell is an insect cell that permits protein expression. In some embodiments, the cell is a lymphocyte.

In some embodiments, the cells are precursor T cells or T regulatory cells. In some embodiments, the cells stem cells, such as hematopoietic stem cells. In some embodiments, the cell is a NK cell. In some embodiments, the cells are CD34+, CD8+, and/or CD4+T lymphocytes. In some embodiments, the cell is a B cell. In some embodiments, the cell is a neuronal stem cell.

In some embodiments, the cells are CD8+T cytotoxic lymphocyte cells, which may include naïve CD8+ T cells, central memory CD8+ T cells, effector memory CD8+ T cells, or bulk CD8+ T cells. In some embodiments, the cells are CD4+T helper lymphocyte cells, which may include naïve CD4+ T cells, central memory CD4+ T cells, effector memory CD4+ T cells, or bulk CD4+ T cells.

The lymphocytes (T lymphocytes) can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques or variations thereof that will be apparent to those skilled in the art. In some embodiments, the T cells are autologous T cells obtained from a patient.

For example, the desired T cell population or subpopulation can be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). The non-dividing feeder cells can comprise gamma-irradiated PBMC feeder cells. In some embodiments, the PBMC are irradiated with gamma rays in the range of 3000 to 3600 rads to prevent cell division. In some embodiments, the PBMC are irradiated with gamma rays of 3000, 3100, 3200, 3300, 3400, 3500 or 3600 rads or any value of rads between any two endpoints of any of the listed values to prevent cell division. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least 25° C., preferably at least 30° C., more preferably 37° C. In some embodiments, the temperature for the growth of human T lymphocytes is 22, 24, 26, 28, 30, 32, 34, 36, 37° C., or any other temperature between any two endpoints of any of the listed values.

After isolation of T lymphocytes both cytotoxic and helper T lymphocytes can be sorted into naïve, memory, and effector T cell subpopulations either before or after expansion.

CD8+ cells can be obtained by using standard methods. In some embodiments, CD8+ cells are further sorted into naïve, central memory, and effector memory cells by identifying cell surface antigens that are associated with each of those types of CD8+ cells. In some embodiments, memory T cells are present in both CD62L+ and CD62L− subsets of CD8+ peripheral blood lymphocytes. PBMC are sorted into CD62L−CD8+ and CD62L+CD8+ fractions after staining with anti-CD8 and anti-CD62L antibodies. In some embodiments, the expression of phenotypic markers of central memory $T_{CM}$ include CD45RO, CD62L, CCR7, CD28, CD3, and/or CD127 and are negative or low for granzyme B. In some embodiments, central memory T cells are CD45RO+, CD62L+, and/or CD8+ T cells. In some embodiments, effector $T_E$ are negative for CD62L, CCR7, CD28, and/or CD127, and positive for granzyme B and/or perforin. In some embodiments, naïve CD8+T lymphocytes are characterized by the expression of phenotypic markers of naïve T cells comprising CD62L, CCR7, CD28, CD3, CD127, and/or CD45RA.

CD4+T helper cells are sorted into naïve, central memory, and effector cells by identifying cell populations that have cell surface antigens. CD4+ lymphocytes can be obtained by standard methods. In some embodiments, naïve CD4+T lymphocytes are CD45RO−, CD45RA+, CD62L+, and/or CD4+ T cells. In some embodiments, central memory CD4+ cells are CD62L+ and/or CD45RO+. In some embodiments, effector CD4+ cells are CD62L− and/or CD45RO−.

Whether a cell, such as a mammalian cell, or cell population, such as a population of mammalian cells, is selected for expansion depends upon whether the cell or population of cells has undergone two distinct genetic modification events. If a cell, such as a mammalian cell, or a population of cells, such as a population of mammalian cells, has undergone one or fewer genetic modification events, then the addition of a ligand will result in no dimerization. However, if the cell, such as a mammalian cell, or the population of cells, such as a population of mammalian cells, has undergone two genetic modification events, then the addition of the ligand will result in dimerization of the CISC component, and subsequent signaling cascade. Thus, a cell, such as a mammalian cell, or a population of cells, such as a population of mammalian cells, may be selected based on its response to contact with the ligand. In some embodiments, the ligand may be added in an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

In some embodiments, a cell, such as a mammalian cell, or a population of cells, such as a population of mammalian cells, may be positive for the dimeric CISC based on the expression of a marker as a result of a signaling pathway. Thus, a cell population positive for the dimeric CISC may be determined by flow cytometry using staining with a specific antibody for the surface marker and an isotype matched control antibody.

Compositions

Provided herein are compositions that comprise a genetically modified cell, such as a mammalian cell, preparation as set forth in this disclosure. In some embodiments, the cells, such as mammalian cells, include the protein sequences as described in the embodiments herein. In some embodiments, the compositions include CD4+ T cells that have a CISC comprising an extracellular binding domain, a hinge domain, a transmembrane domain, and signaling domain. In some embodiments, the CISC is an IL2R-CISC. In other embodiments, the composition further comprises a cell, such as a mammalian cell, preparation comprising CD8+ T cells that have a CISC comprising an extracellular binding domain, a hinge domain, a transmembrane domain, and a signaling domain. In some embodiments, the CISC components dimerize in the presence of a ligand, preferably simultaneously. In some embodiments, each of these populations can be combined with one another or other cell types to provide a composition.

In some embodiments, the cells of the composition are CD4+ cells. The CD4+ cell can be T helper lymphocyte cells, naïve CD4+ T cells, central memory CD4+ T cells, effector memory CD4+ T cells, or bulk CD4+ T cells. In some embodiments, the CD4+ helper lymphocyte cell is a naïve CD4+ T cell, wherein the naïve CD4+ T cell comprises a CD45RO−, CD45RA+, and/or is a CD62L+CD4+ T cell.

In some embodiments, the cells of the composition are CD8+ cells. The CD8+ cell can be a T cytotoxic lymphocyte cell, a naïve CD8+ T cell, central memory CD8+ T cell, effector memory CD8+ T cell and/or bulk CD8+ T cell. In some embodiments, the CD8+ cytotoxic T lymphocyte cell is a central memory T cell, wherein the central memory T cell comprises a CD45RO+, CD62L+, and/or CD8+ T cell. In yet other embodiments, the CD8+ cytotoxic T lymphocyte cell is a central memory T cell and the CD4+ helper T lymphocyte cell is a naïve or central memory CD4+ T cell.

In some embodiments, the compositions comprise T cell precursors. In some embodiments, the compositions comprise hematopoietic stem cells. In some embodiments, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or a CD4+T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell. In some embodiments, the precursor T cell is a hematopoietic stem cell.

In some compositions, the cells are NK cells.

In some embodiments, the cell is CD8+ or a CD4+ cell. In some embodiments, the cell is a CD8+T cytotoxic lymphocyte cell selected from the group consisting of naïve CD8+ T-cells, central memory CD8+ T-cells, effector memory CD8+ T-cells and bulk CD8+ T-cells. In some embodiments, the cell is a CD4+T helper lymphocyte cell that is selected from the group consisting of naïve CD4+ T-cells, central memory CD4+ T-cells, effector memory CD4+ T-cells, and bulk CD4+ T-cells. In some embodiments, the cell is a precursor T-cell. In some embodiments, the cell is a stem cell. In some embodiments, the cell is a hematopoietic stem cell or NK cell. In some embodiments, the cell is a B cell. In some embodiments, the cell is a neuronal stem cell. In some embodiments, the cell further comprises a chimeric antigen receptor.

Also provided herein are kits and systems including the cells, expression vectors, and protein sequences provided and described herein. Thus, for example, provided herein is a kit comprising one or more of: a protein sequence as described herein; an expression vector as described herein; and/or a cell as described herein. Also provided is a system for selectively activation a signal into an interior of a cell, the system comprising a cell as described herein, wherein the cell comprises an expression vector as described herein comprising a nucleic acid encoding a protein sequence as described herein.

Method of Making a Cell that Expresses a Dimeric CISC Component

In some embodiments described herein, it may be desired to introduce a protein sequence or an expression vector into a host cell, such as a mammalian cell, e.g., a lymphocyte, to be used for drug regulated cytokine signaling and/or for the selective expansion of cells that express the dimeric CISC components. For example, the dimeric CISC can allow for cytokine signaling in cells that have the introduced CISC components for transmitting signals to the interior of a cell, such as a mammalian cell, upon contact with a ligand. In addition, the selective expansion of cells, such as mammalian cells, can be controlled to select for only those cells that have undergone two specific genetic modification events, as described herein. Preparation of these cells can be carried out in accordance with known techniques that will be apparent to those skilled in the art based upon the present disclosure.

In some embodiments, a method of making a CISC-bearing cell, such as a mammalian cell, is provided, wherein the cell expresses a dimeric CISC. The method can include delivering to a cell, such as a mammalian cell, the protein sequence of any one of the embodiments or embodiments described herein or the expression vector of the embodiments or embodiments described herein and delivering to the cell, such as a mammalian cell. In some embodiments, the protein sequence comprises a first and a second sequence. In some embodiments, the first sequence encodes for a first CISC component comprising a first extracellular binding domain, a hinge domain, a linker of a specified length, wherein the length is preferably optimized, a transmembrane domain, and a signaling domain. In some embodiments, the second sequence encodes for a second CISC component comprising a second extracellular binding domain, a hinge domain, a linker of a specified length, wherein the length is preferably optimized, a transmembrane domain, and a signaling domain. In some embodiments, the spacer is 1, 2, 3, 4, 5, 6, 7, 8, 9, 10, 11, 12, 13, 14 or 15 amino acids in length or a length within a range defined by any two of the aforementioned lengths. In some embodiments, the signaling domain comprises an interleukin-2 signaling domain, such as an IL2Rb or an IL2Rg domain. In some embodiments, the extracellular binding domain is a binding domain that binds to rapamycin or a rapalog, comprising FKBP or FRB or a portion thereof. In some embodiments, the cell is a CD8+ or a CD4+ cell. In some embodiments, the cell is a CD8+T cytotoxic lymphocyte cell selected from the group consisting of naïve CD8+ T-cells, central memory CD8+ T-cells, effector memory CD8+ T-cells and bulk CD8+ T-cells. In some embodiments, the cell is a CD4+T helper lymphocyte cell that is selected from the group consisting of naïve CD4+ T-cells, central memory CD4+ T-cells, effector memory CD4+ T-cells, and bulk CD4+ T-cells. In some embodiments, the cell is a precursor T-cell. In some embodiments, the cell is a stem cell. In some embodiments, the cell is a hematopoietic stem cell. In some embodiments, the cell is a B cell. In some embodiments, the cell is a neuronal stem cell. In some embodiments, the cell is an NK cell.

Method of Activating a Signal in the Interior of a Cell

In some embodiments, a method of activating a signal in the interior of a cell, such as a mammalian cell, is provided. The method can include providing a cell, such as a mammalian cell, as described herein, wherein the cell comprises a protein sequence as set forth herein or an expression vector as set forth herein. In some embodiments, the method further comprises expressing the protein sequence encoding a dimeric CISC as described herein, or expression the vector as described herein. In some embodiments, the method comprises contacting the cell, such as a mammalian cell, with a ligand, which causes the first and second CISC components to dimerize, which transduces a signal into the interior of the cell. In some embodiments, the ligand is rapamycin or rapalog. In some embodiments, the ligand is an IMID-class drug (e.g. thalidomide, pomalidomide, lenalidomide or related analogues). In some embodiments an effective amount of a ligand for inducing dimerization is provided an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

In some embodiments, the ligand used in these approaches is rapamycin or a rapalog, comprising, for example, everolimus, CCI-779, C20-methallylrapamycin, C16-(S)-3-methylindolerapamycin, C16-iRap, AP21967, sodium mycophenolic acid, benidipine hydrochloride, AP23573, or AP1903, or metabolites, derivatives, and/or combinations thereof. Additional useful rapalogs may include, for example, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and/or alternative substitution on the cyclohexyl ring or replacement of the cyclohexyl ring with a substituted cyclopentyl ring. Additional useful rapalogs may include novolimus, pimecrolimus, ridaforolimus, tacrolimus, temsirolimus, umirolimus, or zotarolimus, or metabolites, derivatives, and/or combinations thereof. In some embodiments, the ligand is an IMID-class drug (e.g. thalidomide, pomalidomide, lenalidomide or related analogues).

In some embodiments, detecting a signal in the interior of the cell, such as a mammalian cell, can be achieved by a method of detecting a marker that is the result of a signaling pathway. Thus, for example, a signal may be detected by determining the levels of Akt or other signaling marker in a cell, such as a mammalian cell, through a process of Western blot, flow cytometry, or other protein detection and quantification method. Markers for detection may include, for example, JAK, Akt, STAT, NF-κ, MAPK, PI3K, JNK, ERK, or Ras, or other cellular signaling markers that are indicative of a cellular signaling event.

In some embodiments, transduction of a signal affects cytokine signaling. In some embodiments, transduction of the signal affects IL2R signaling. In some embodiments, transduction of the signal affects phosphorylation of a downstream target of a cytokine receptor. In some embodiments, the method of activating a signal induces proliferation in CISC-expressing cells, such as mammalian cells, and a concomitant anti-proliferation in non-CISC expressing cells.

Figure 4A:
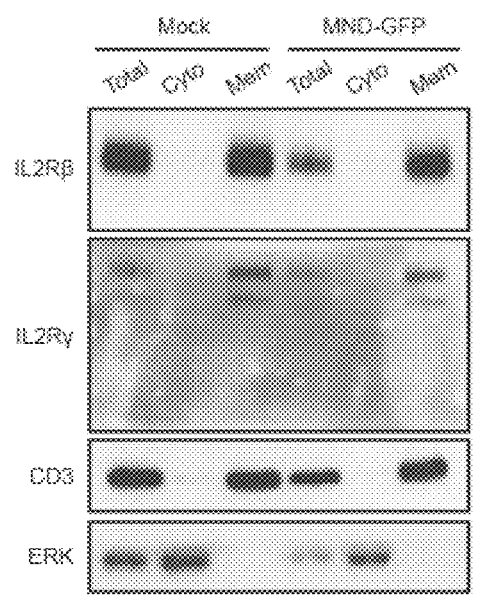
FIG. 4A and FIG. 4B show images of Western blots. IL2R-CISC human CD4+ T cells were harvested two days post transduction, and the cytoplasmic and membrane fractions were isolated. The top panel is a control to demonstrate that the methods used efficiently fractionate cytosol and membrane: the top gel shows IL2Rβ; the middle gel shows IL2Rγ; and bottom two gels are control gels showing CD3 and ERK.
Figure 4B:
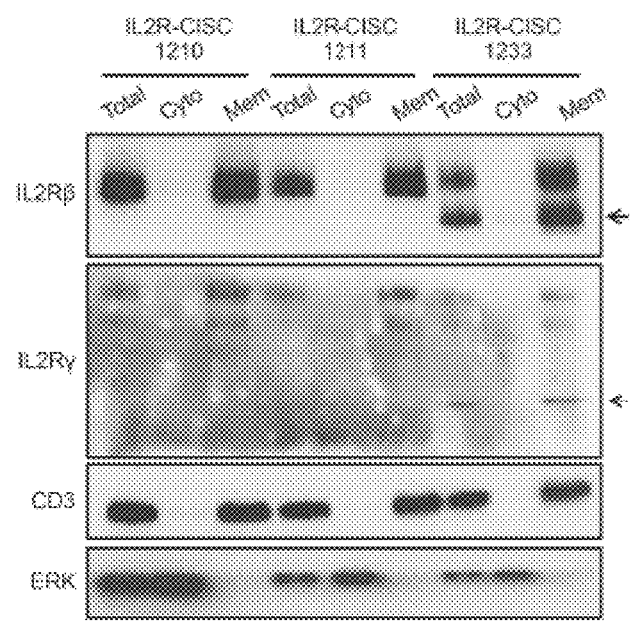
Figure 5:
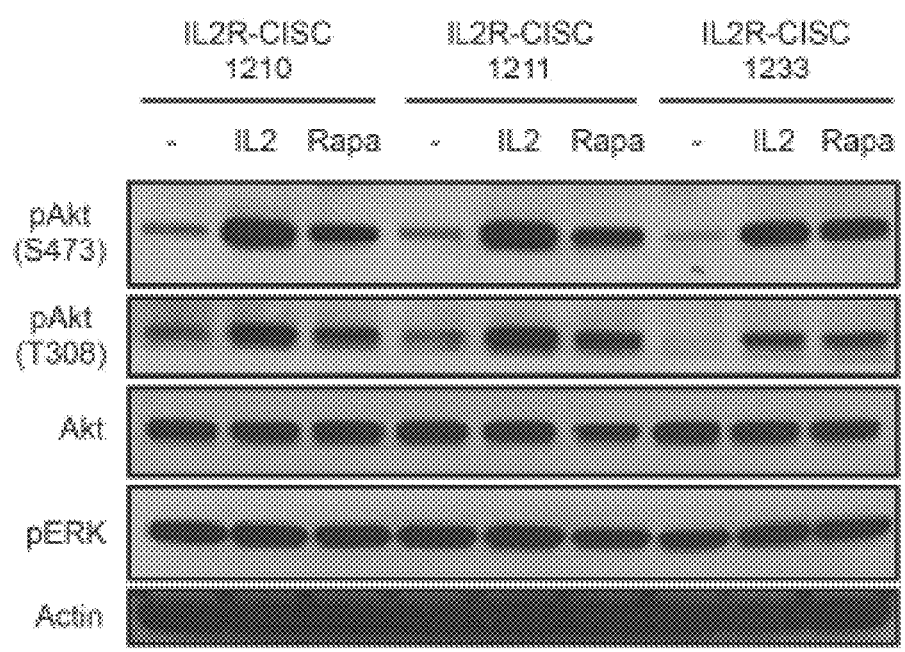
FIG. 5 shows an image of a Western blot for IL2R-CISC. IL2R-CISC human CD4+ T cells were analyzed following 15 days of rapamycin treatment at 1 nM, following by cytokine starvation for 48 hours. Stimulation with IL-2 (50 ng) or rapamycin (100 nM) for 20 minutes was followed, and the cells were harvested for Western blot. The Western blot shows Akt activation, indicating the capacity for a chemical-induced signaling complex to drive cell expansion.

For cellular signaling to take place, not only must cytokine receptors dimerize or heterodimerize, but they must be in the proper configuration for a conformational change to take place (Kim, et al. *NMR Structural Studies of Interaction of a Small, Nonpeptidyl Tpo Mimic with the Thrombopoietin Receptor Extracellular Juxtamembrane and Transmembrane Domains*, J Biol Chem, 282, 2007). Thus, dimerization in conjunction with the correct conformational positioning of signaling domains are desired processes for appropriate signaling, because receptor dimerization or heterodimerization alone is insufficient to drive receptor activation. The chemical-induced signaling complexes described herein are preferably in the correct orientation for downstream signaling events to occur. As shown in the Western blots of FIGS. 4A-4B and 5, multiple downstream signaling events occur in the presence of a ligand, including both Akt activation (required for driving cell proliferation), a feature that indicates successful orientation, and dimerization of the signaling complexes described herein.

Method of Selective Expansion of Cell Populations

In some embodiments, a method of selectively expanding a population of cells, such as mammalian cells, is provided herein. In some embodiments, the method comprises providing a cell, such as a mammalian cell, as described herein, wherein the cell comprises a protein sequence as set forth herein or an expression vector as set forth herein. In some embodiments, the method further comprises expressing the protein sequence encoding a dimeric CISC as described herein, or expression the vector as described herein. In some embodiments, the method comprises contacting the cell, such as a mammalian cell, with a ligand, which causes the first and second CISC components to dimerize, which transduces a signal into the interior of the cell. In some embodiments, the ligand is rapamycin or rapalog. In some embodiments an effective amount of a ligand provided for inducing dimerization is an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

In some embodiments, the ligand used is rapamycin or a rapalog, comprising, for example, everolimus, CCI-779, C20-methallylrapamycin, C16-(S) methylindolerapamycin, C16-iRap, AP21967, sodium mycophenolic acid, benidipine hydrochloride, or AP23573, AP1903, or metabolites, derivatives, and/or combinations thereof. Additional useful rapalogs may include, for example, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and/or alternative substitution on the cyclohexyl ring or replacement of the cyclohexyl ring with a substituted cyclopentyl ring. Additional useful rapalogs may include novolimus, pimecrolimus, ridaforolimus, tacrolimus, temsirolimus, umirolimus, or zotarolimus, or metabolites, derivatives, and/or combinations thereof. In some embodiments, the ligand is an IMID-class drug (e.g. thalidomide, pomalidomide, lenalidomide or related analogues).

In some embodiments, the selective expansion of a population of cells, such as mammalian cells, takes place only when two distinct genetic modification events have taken place. One genetic modification event is one component of the dimeric chemical-induced signaling complex, and the other genetic modification event is the other component of the dimeric chemical-induced signaling complex. When both events take place within the population of cells, such as a population of mammalian cells, the chemical-induced signaling complex components dimerize in the presence of a ligand, resulting in an active chemical-induced signaling complex and generation of a signal into the interior of the cells. The activation and phosphorylation of Akt, as shown in the Western blot in FIG. 5, indicates successful achievement of a full proliferative signal, which is desired to achieve a significant selective expansion of the cell population expressing both genetic modification events. Other signaling markers may also be detected, but only achievement of these events in conjunction with Akt activation is able to achieve sufficient cellular expansion to allow for selective expansion of a modified cell population in which both genetic modification events have taken place in a given population of cells, such as a population of mammalian cells.

Figure 6:
FIG. 6 outlines the experiment demonstrating use of an IL2R-CISC to selectively expand a cell population. Each architecture of IL2R-CISC (i.e. 1210, 1211, and 1233) was cis-linked together with GFP using 2A sequences, and placed under the control of an MND promoter in a lentiviral expression cassette (as schematized in FIG. 5, bottom). Lentiviral particles from each IL2R-CISC architecture were generated and used to transduce primary human T-cells. Following transduction, the cells were grown for 2 days in IL2, and then divided in half, with half grown in IL2 alone and half in rapamycin alone, as indicated.
Figure 7A:
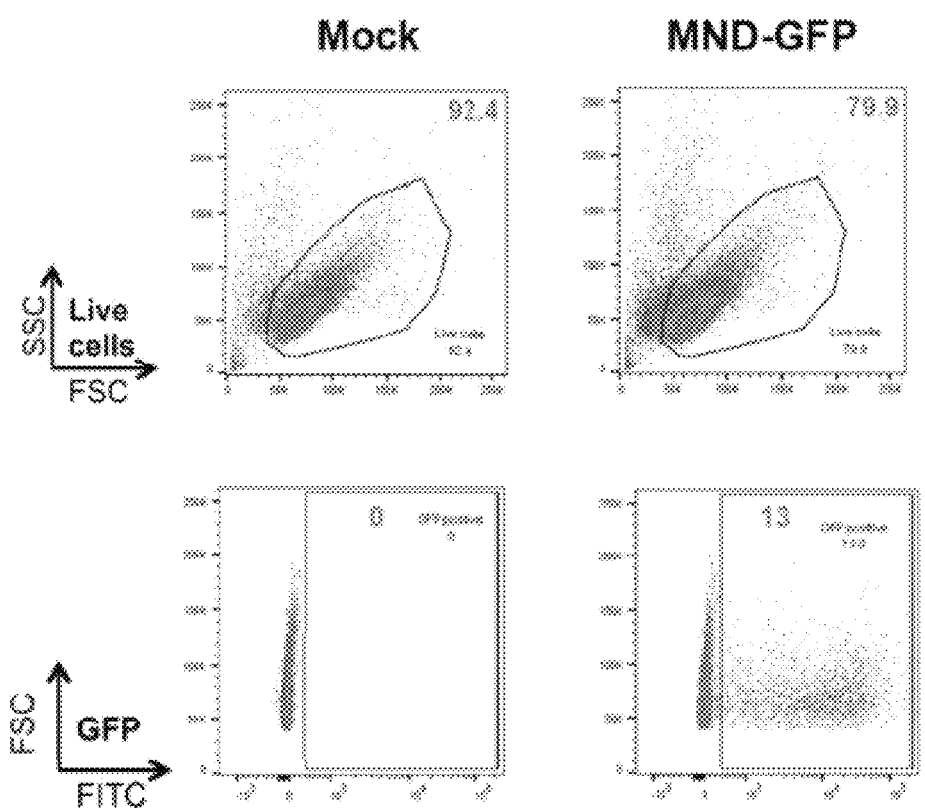
FIG. 7A demonstrates efficient transduction of T-cells using a lentiviral vector driving expression of GFP alone.
Figure 7B:
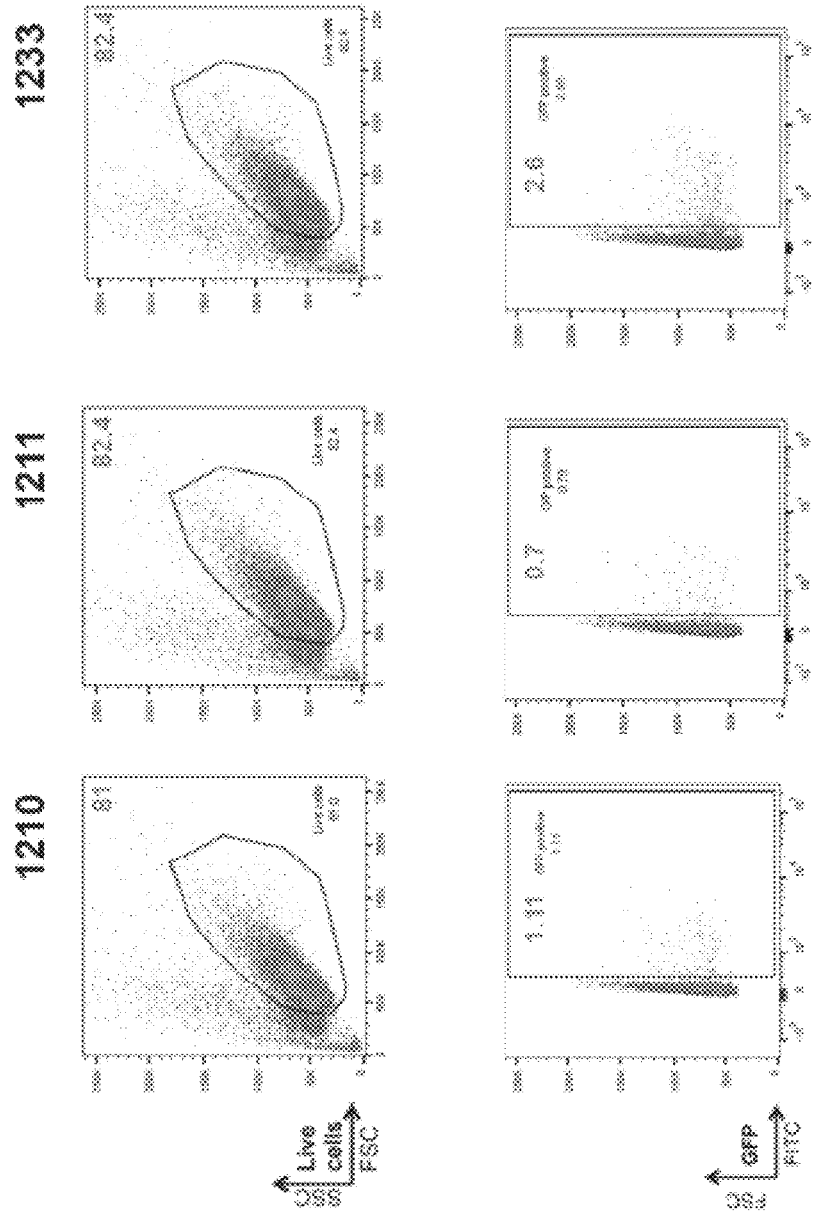
FIG. 7B shows the expression of 1210, 1211, and 1233 expressed using a vector outlined at the bottom of FIG. 3—MND-IL2Rb-CISC-2A-IL2Rg-CISC-2A-GFP, as compared to mock and MND-GFP retroviral vector. T cells were activated for 48 hours and then incubated for 28 hours. T cells were plated with IL-2/7/15. Lentiviral transduction included IL2-CISC of MND-GFP control with protamine sulfate. Transduced cells were incubated at 37° C. for 24 hours with cytokine (IL-2, 50 ng/mL; IL-5, 5 ng/mL; IL-17, 5 ng/mL). IL2-CISC expression was determined by GFP expression using flow cytometry.

FIG. 6 provides an exemplary method for the selective expansion of a cell population, such as a population of mammalian cells. As shown in FIG. 6, a CISC including IL2R was prepared. Each architecture of IL2R-CISC (i.e. 1210, 1211, and 1233) was cis-linked together with GFP using 2A sequences, and placed under the control of an MND promoter in a lentiviral expression cassette.

Lentiviral particles from each IL2R-CISC architecture were generated and used to transduce primary human T-cells. CD4+ T cells were activated for 60 hours. The cells were then plated in a 24-well dish by plating 1 million cells per well in 1 mL medium with IL2/7/15. Lentivirus was transduced with or without beads, using 15 µL of IL2R-CISC and 3 µL of MND-GFP control with protamine sulfate at 4 µg/mL (0.5 mL medium) in a 24-well dish. The cells were then spinoculated at 800 g for 30 minutes at 33° C. followed by the addition of 1.5 mL medium after 4 hours of incubation. The transduced T cells were incubated at 37° C. for 48 hours with cytokines, including 50 ng/mL IL2, 5 ng/mL of IL5, and 5 ng/mL of IL17. The GFP signal was determined and the IL2R-CISC level of transduced T cells was determined. The transduction efficiency was from 10-30% for IL2R-CISC and about 80% for MND-GFP.

Figure 8:
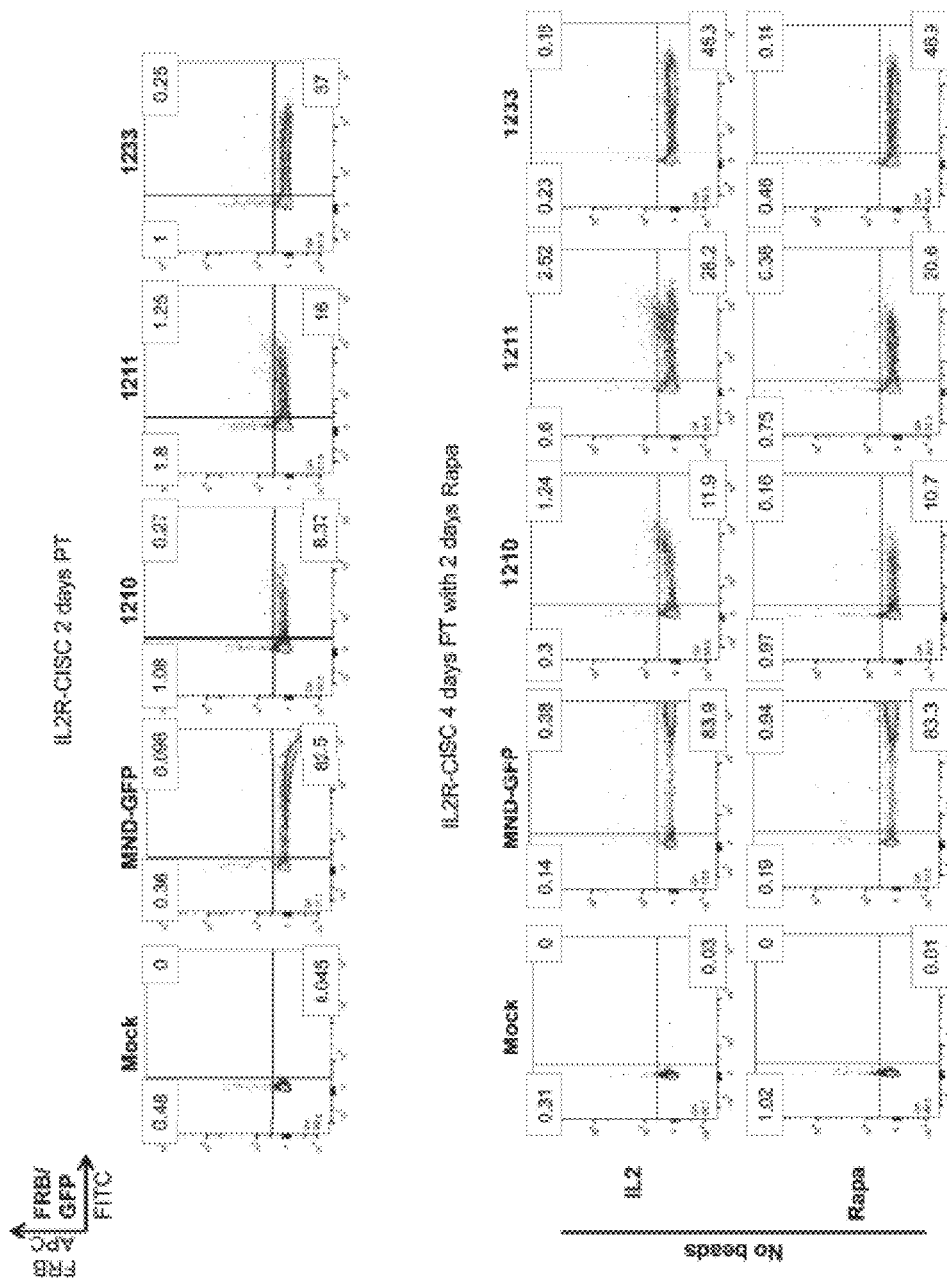
FIG. 8 shows flow analysis of cells. Top flow panels show Flow Analysis of cells for GFP expression (X-axis) and FRB expression (the extracellular domain of the IL2Rg-CISC component, Y-axis) at 2 days (just prior to placing cells into IL2 or rapamycin cultures). Bottom two flow panels show Flow Analysis of cells for GFP expression (X-axis) and FRB expression 4 days post transduction, 2 days following division into culture in IL2 alone (top panels), or rapamycin (bottom panel). Note that in particular for 1233 (bottom right flow panel), cells cultured in rapamycin alone are beginning to enrich for IL2R-CISC expression as read out by the cis-linked GFP marker.
Figure 9:
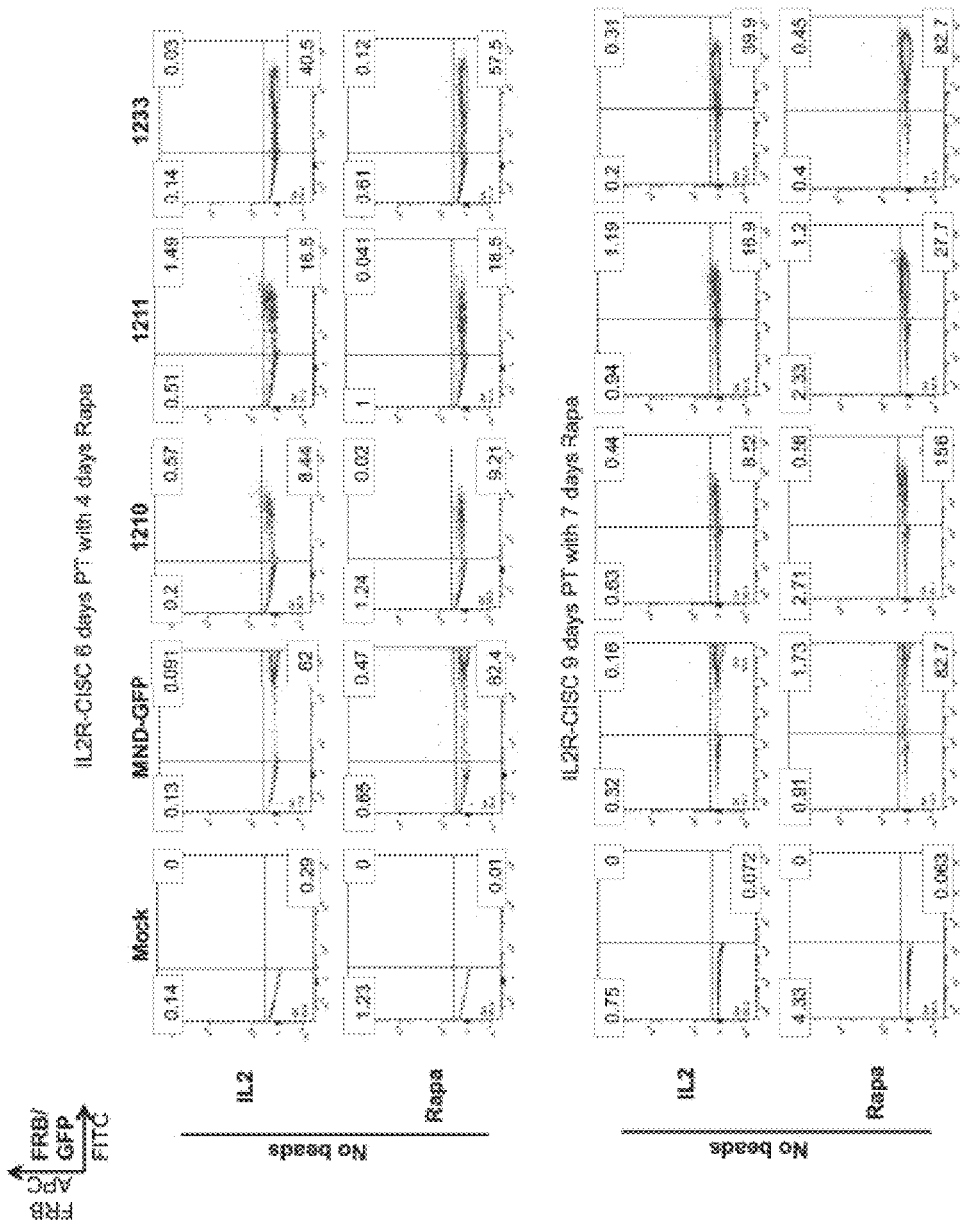
FIG. 9 shows flow analysis of cells. Top two flow panels show Flow Analysis of cells for GFP expression (X-axis) and FRB expression 6 days post transduction, 4 days following division into culture in IL2 alone (top panels), or rapamycin (bottom panel). Note the further enrichment of the GFP marker for 1233. Bottom two flow panels show Flow Analysis of cells for GFP expression (X-axis) and FRB expression 9 days post transduction, 7 days following division into culture in IL2 alone (top panels), or rapamycin (bottom panel). Note the further enrichment of the 1233 GFP+ cells.
Figure 10:
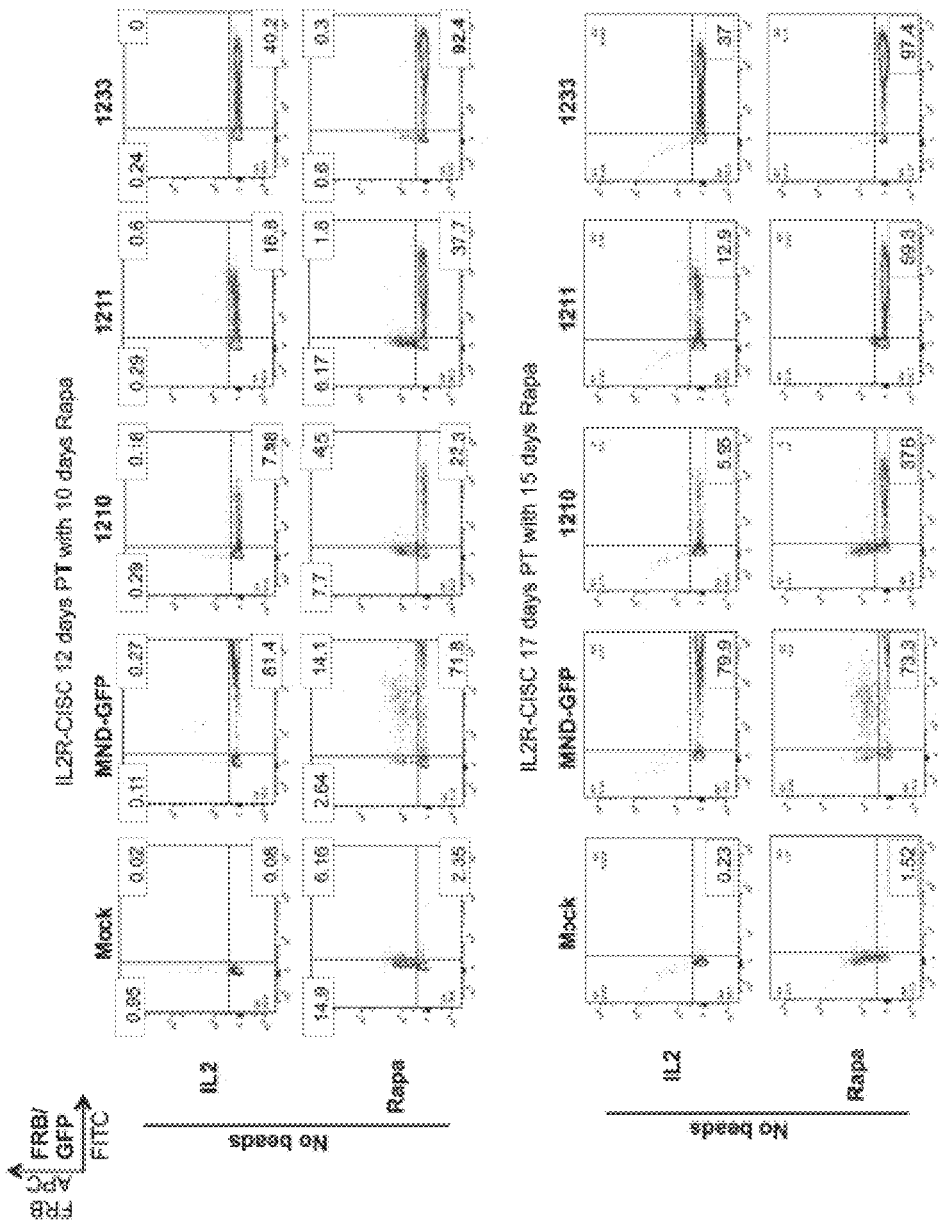
FIG. 10 shows flow analysis of cells. Top two flow panels show Flow Analysis of cells for GFP expression (X-axis) and FRB expression 12 days post transduction, 10 days following division of culture in IL2 alone (top panels), or rapamycin (bottom panel). Bottom two flow panels show Flow Analysis of cells for GFP expression (X-axis) and FRB expression 17 days post transduction, 15 days following dividing into culture in IL2 alone (top panels), or rapamycin (bottom panel). Cells expressing the 1233 IL2R-CISC are now enriched to 97% of the cell population (far bottom right flow panel).
Figure 11:
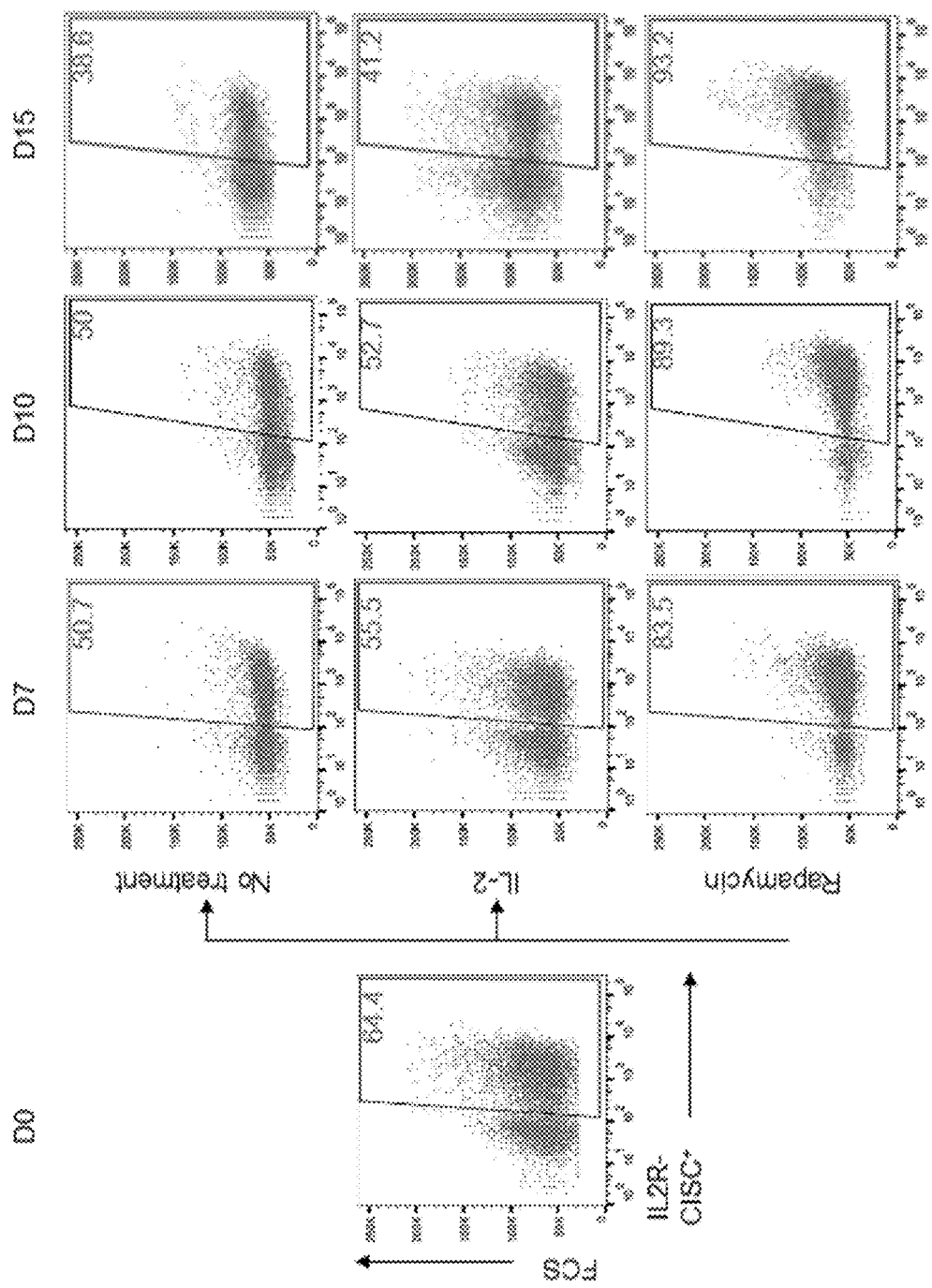
FIG. 11 demonstrates the enrichment of IL2R-CISC V3 expressing cells over the course of 15 days of an experiment as outlined in FIG. 6, but carried out for 25 days. The leftmost single panel represents the cells at the start of rapamycin treatment. Each row of panels represents a different treatment. As can be seen in the bottom row, by 15 days, the IL2R-CISC V3 cells had enriched from a starting transduced population of 64% mCherry positive to >93% mCherry positive when cultured in rapamycin. In contrast, mock IL-2 treatments resulted in a gradual reduction in mCherry positive cells.

Following transduction, the cells were grown for 2 days in IL2, and then divided in half, with half grown in IL2 alone and half in rapamycin alone, as indicated. T cells were treated with rapamycin (1 nM) or IL2 for 2 days, and cells were plated at 1 million cells/well in a 24-well dish with 2 mL medium. The T cell viability was determined and the expression of GFP+ population and IL2R-CISC expression was determined by using anti-FRB antibody and a secondary APC antibody. FIGS. 7A-7B, and 8-11 show the flow cytometry results of the expression of GFP and FRB in the respective populations. As shown in FIG. 8, for the 1233 architecture, cells cultured in rapamycin alone are enriched for IL2R-CISC expression as read out by the cis-linked GFP marker.

Figure 12:
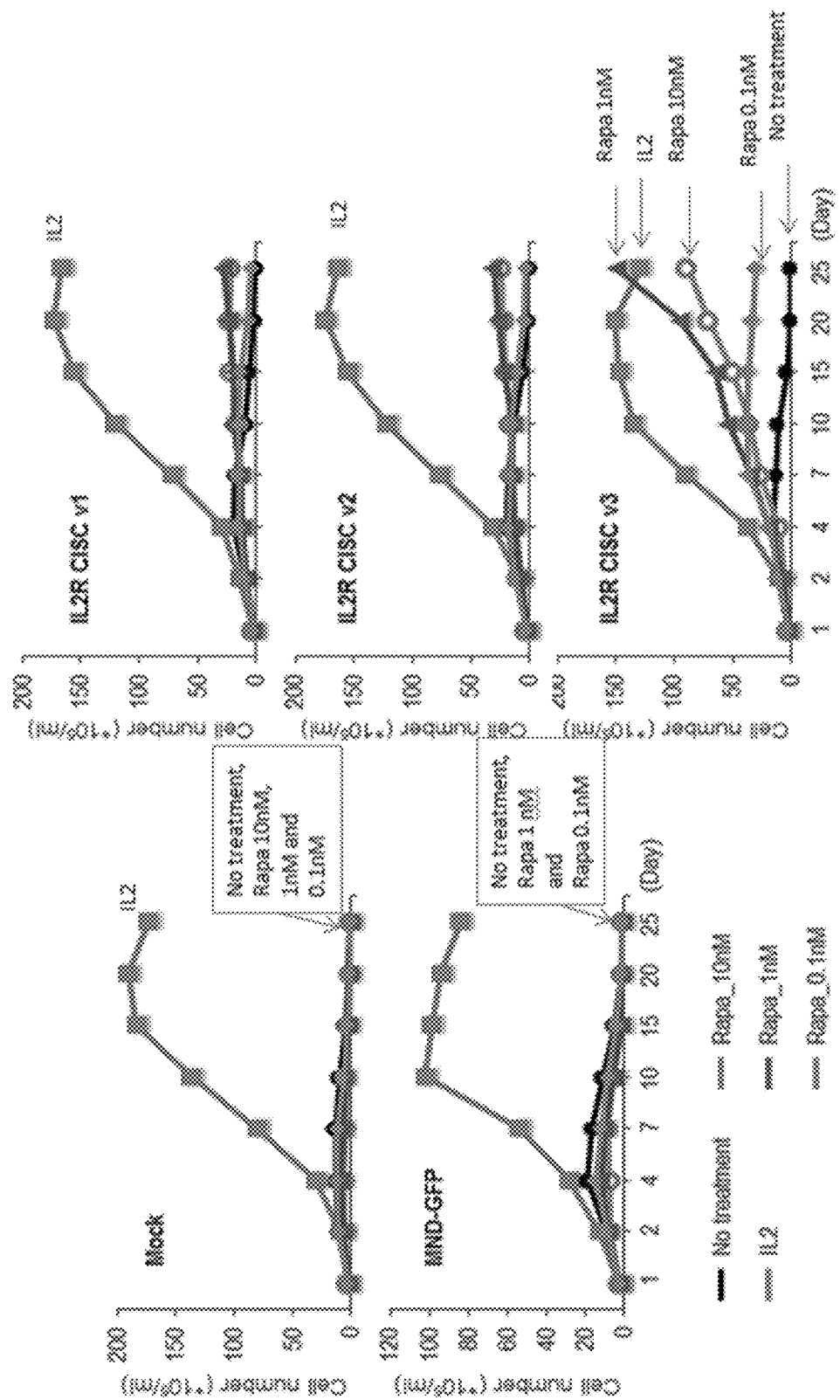
FIG. 12 shows expansion of mCherry positive cell numbers, using the same experimental paradigm as outlined in FIG. 6, but carried out for 25 days. The cell type is indicated in bold in the upper left corner of each panel. Each curve indicated by different symbols delineates a different treatment/culture condition maintained for the 25 days.
Figure 13:
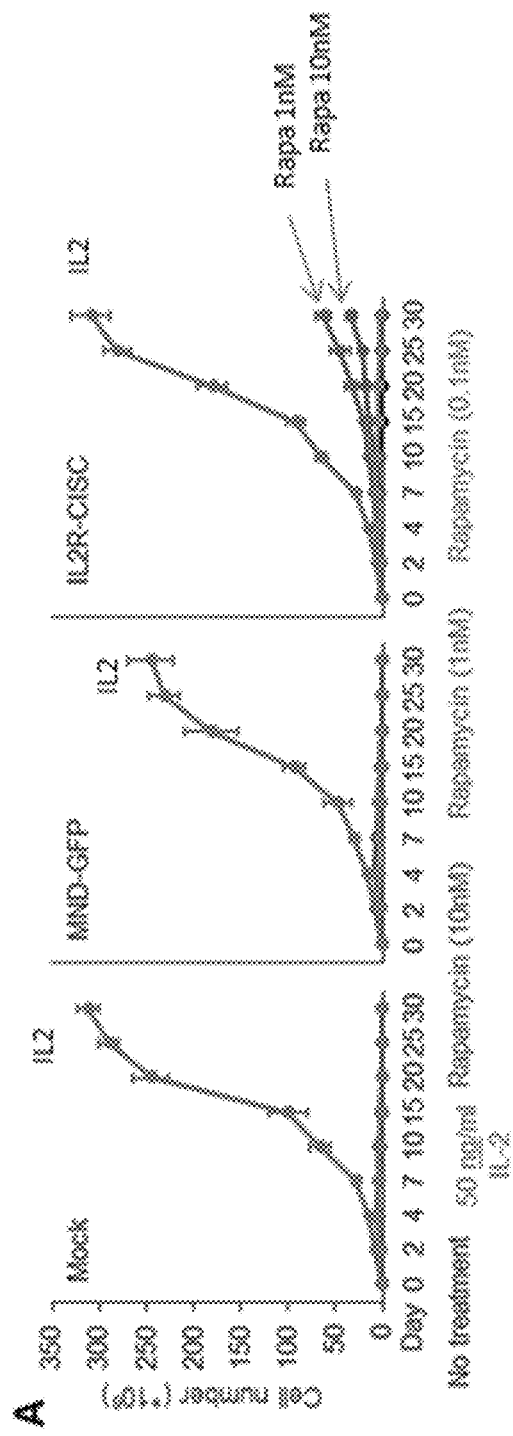
FIG. 13 shows expansion of mock, GFP, or IL2R-CISC V3 expressing cells, using the same experimental paradigm as outlined in FIG. 6, but carried out for 30 days, and utilizing two different rapamycin doses, 1 nM and 10 nM. The cell type is indicated in bold in the upper left corner of each panel. Each curve indicated by different symbols delineates a different treatment/culture condition maintained over the course of the experiment.

FIG. 12 graphically shows the increase in cell proliferation in the presence of rapamycin for the CISC constructs depicted in FIG. 3. V3 is the most efficient architecture for proliferation. FIG. 13 graphically depicts that IL2R-CISC V3 supports human CD4+ T cell proliferation in response to rapamycin treatment.

Figure 14:
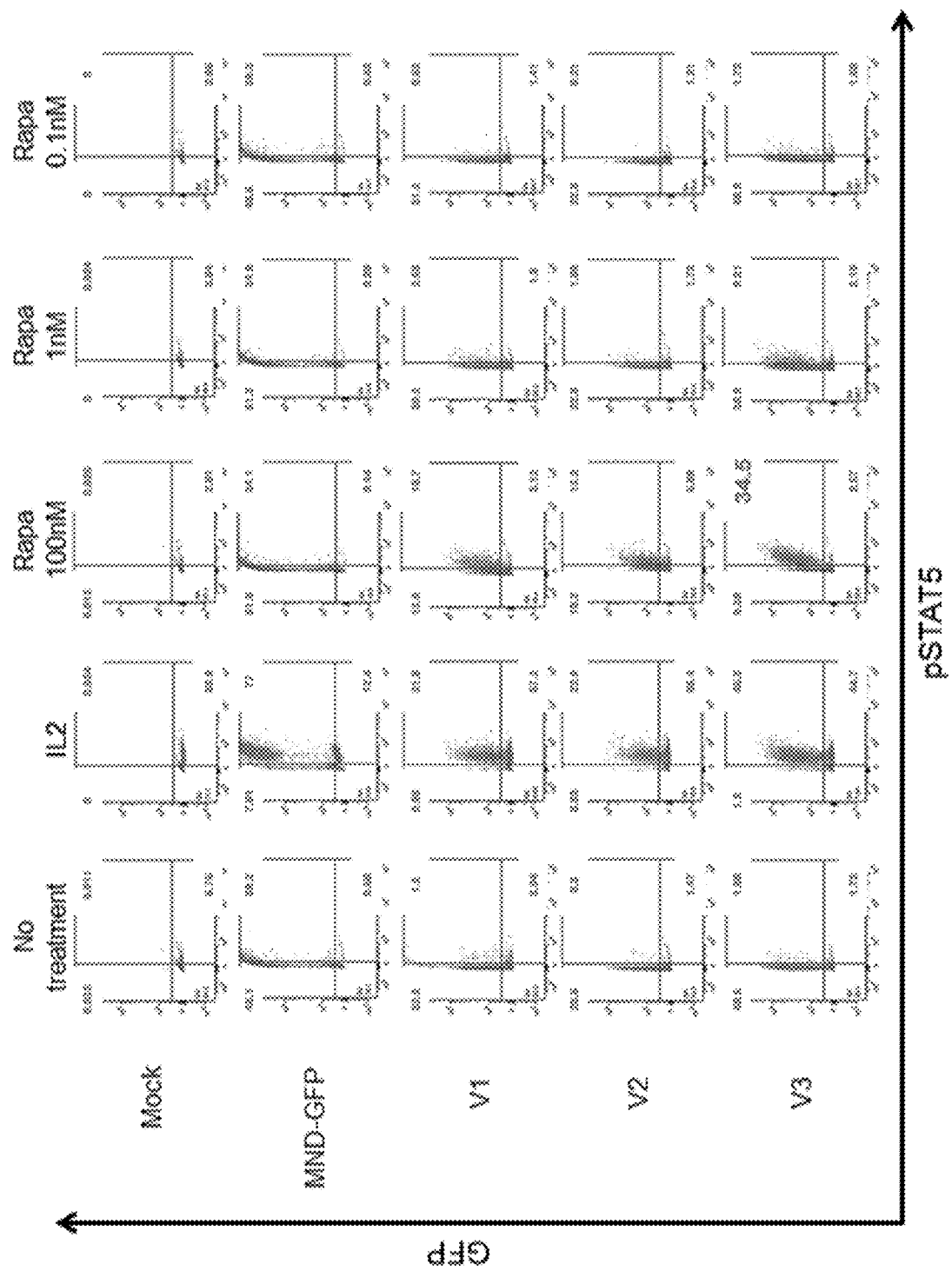
FIG. 14 shows analysis of phosphor-STAT5 signaling in response to the treatments indicated at the top of each column, for the cell types indicated for each row (after 20 days of culture in the indicated condition). As can be seen, cells that received "mock" treatment (row 1) are no longer responsive, as essentially no cells are alive after 20 days. In contrast, while all other cells respond robustly to IL-2 treatment, only IL2R-CISC expressing cells respond to rapamycin with phosphorylation of STAT5, and IL2R-CISC V3 expressing cells respond most robustly, confirming that the V3 architecture signals most effectively.

Using the method as described above also showed that IL2R-CISC expressing T cells induce STAT5 pathway in the presence of rapamycin. As shown by the flow cell data in FIG. 14, the V3 construct is the most efficient architecture for STAT5 pathway signaling.

Figure 15:
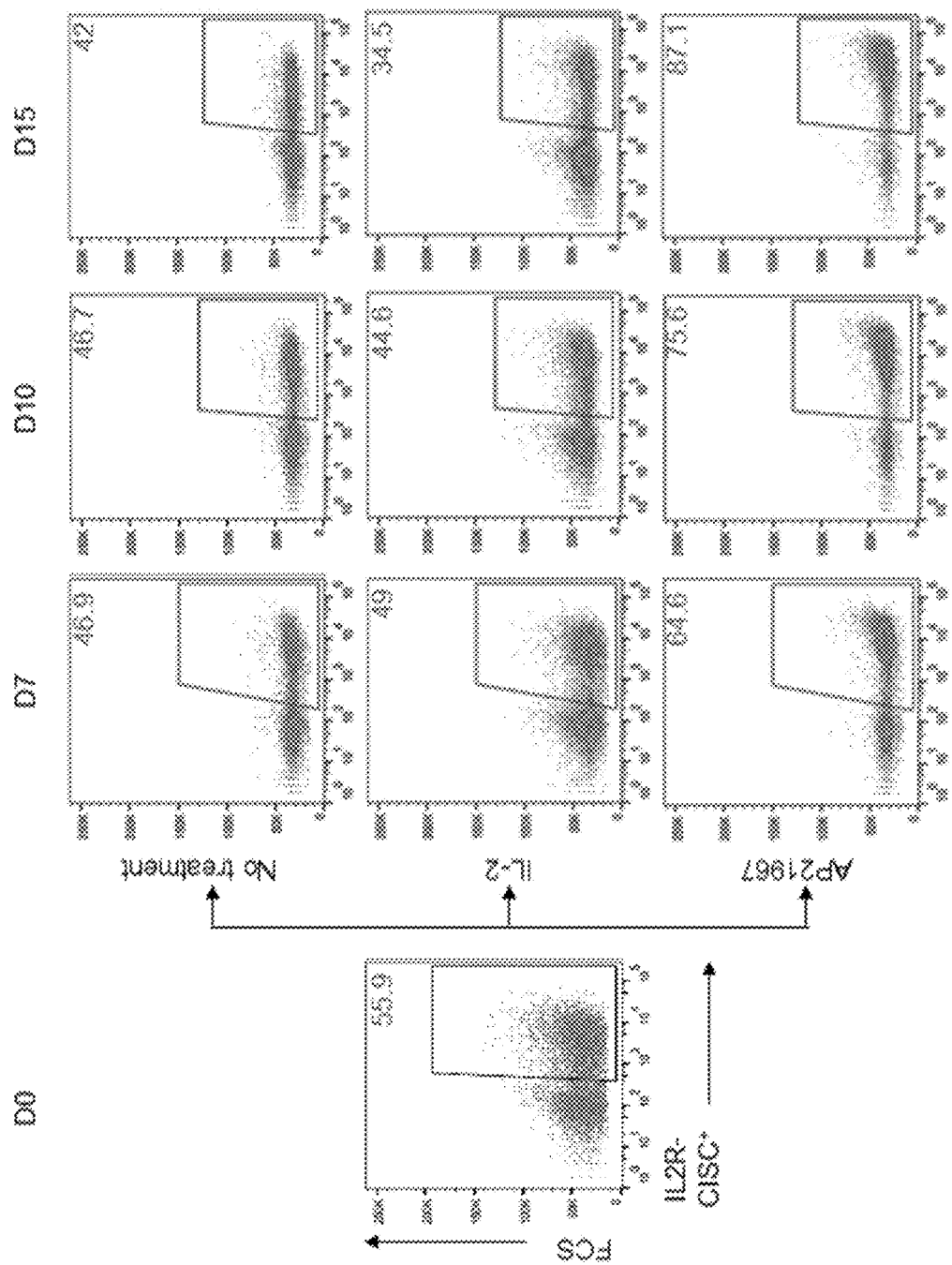
FIG. 15 demonstrates the enrichment of IL2R-CISC V3 expressing cells over the course of 15 days of an experiment identical to that in FIG. 11, except that AP21967 was used as the IL2R-CISC activating ligand. The leftmost single panel represents the cells at the start of AP21967 treatment. Each row of panels represents a different treatment. As can be seen in the bottom row, by 15 days, the IL2R-CISC V3 cells had enriched from a starting transduced population of 64% mCherry positive to >93% mCherry positive when cultured in AP21967. In contrast, mock IL-2 treatments resulted in a gradual reduction in mCherry positive cells.
Figure 16:
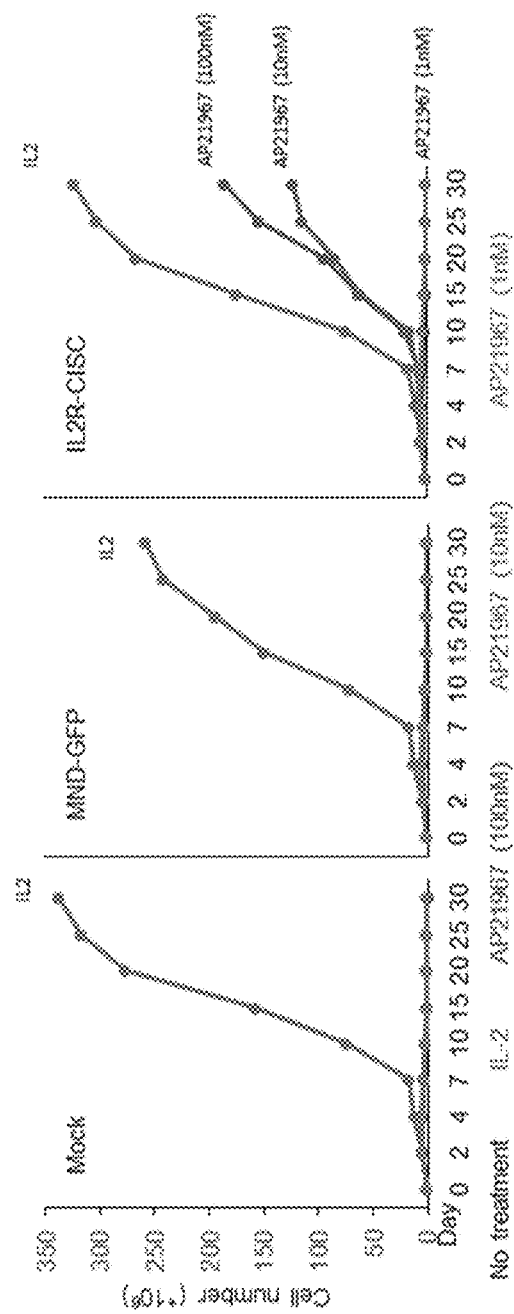
FIG. 16 shows expansion of mock, GFP, or IL2R-CISC V3 expressing cells, using the same experimental paradigm as outlined in FIG. 6, but carried out for 30 days, and utilizing two different AP21967 doses, 10 nM and 100 nM. The cell type is indicated in bold in the upper left corner of each panel. Each curve indicated by different symbols delineates a different treatment/culture condition maintained over the course of the experiment.
Figure 17:
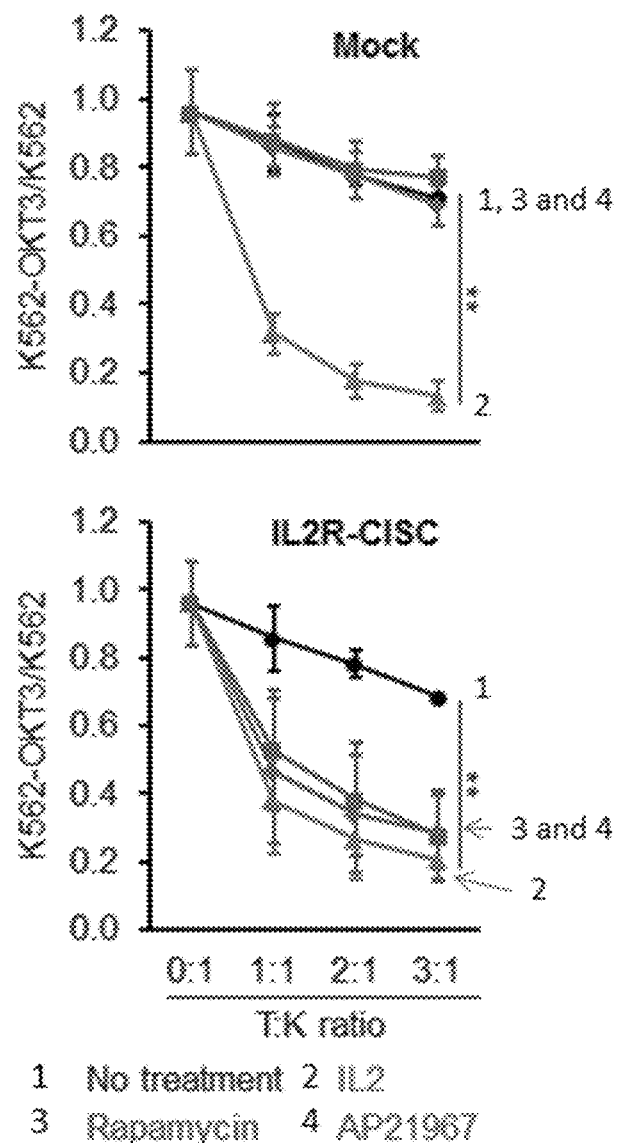
FIG. 17 shows cytolytic activity following expansion of IL2R-CISC V3 expressing cells in the indicated conditions for 15 days, using the experimental setup in FIG. 6, cells were transduced with IL2R-CISC V3 lentivirus, and expanded for 15 days. Cells were then incubated with K562 cells expressing anti-CD3. The expression of anti-CD3 by the target K562 cells causes clustering of CD3 on the T-cells upon contact with the K562 cell, resulting in cytolytic killing of the K562 cells. The IL2R-CISC V3 expressing T-cells expanded in the indicated condition were incubated at different target to killer ratios, and cytolysis was assessed by percent survival of the K562 target cells. Cells expanded through IL2R-CISC exhibited cytolytic activity that was statistically indistinguishable from cells expanded in IL-2.

Similar methods as described herein may be performed using additional rapamycin analogues. For example, the methods described herein were performed using AP21967. In response to AP21967, IL2R-CISC V3 construct promotes human CD4+ T cell survival, as shown in the flow cell data of FIG. 15. In addition, IL2R-CISC promotes CD4+ T cell proliferation in response to AP21967 treatment, as graphically depicted in FIG. 16. FIG. 17 shows the cytotoxicity of IL2R-CISC expanded CD4+ T cells with various treatments, including rapamycin and analogues thereof, indicating normal toxicity after long-term expansion.

Figure 18:
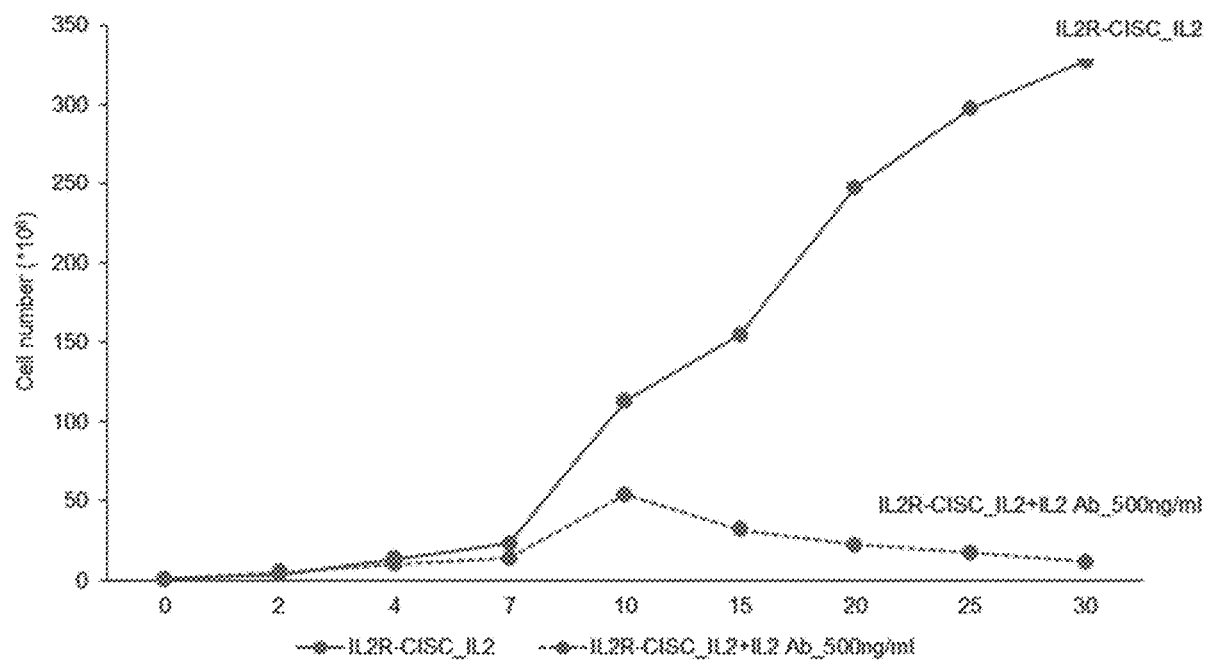
FIG. 18 shows that 500 ng/mL of anti-IL2 neutralizing antibody abrogates expansion of T-cells in IL-2. In this experiment, peripheral blood T-cells were activated using anti-CD3/CD28 beads, and expanded in IL-2 or in IL-2 plus anti-IL2 antibody. Use of the anti-IL2 antibody markedly inhibits expansion of the T-cells.
Figure 19:
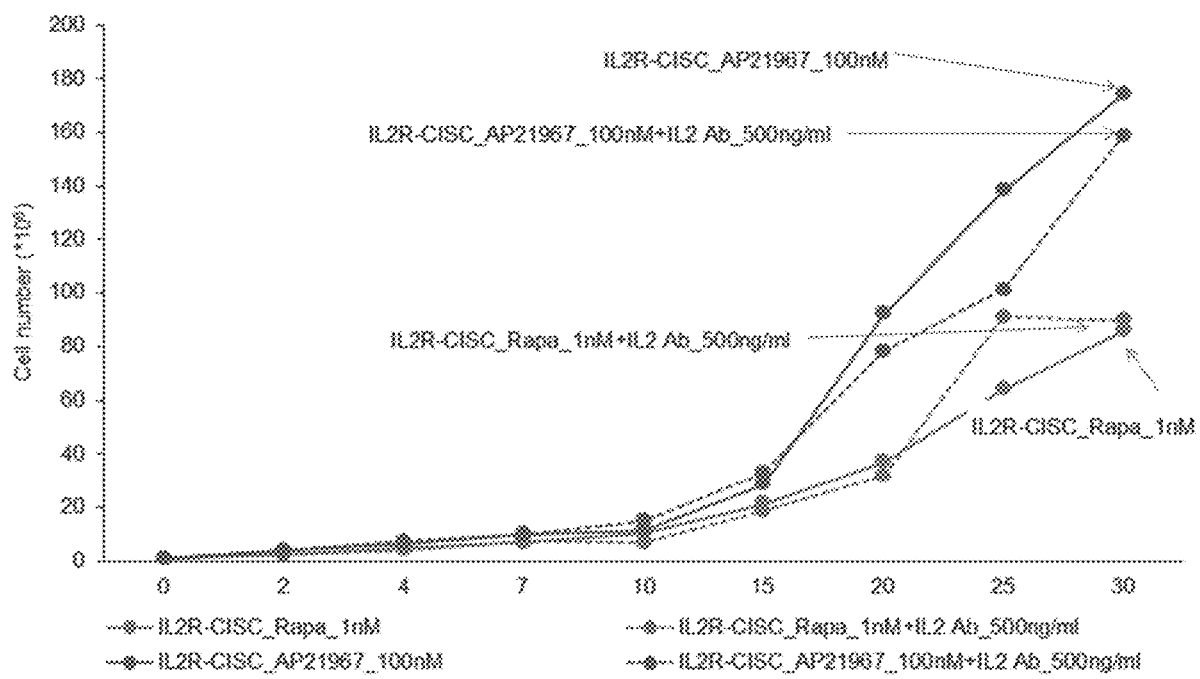
FIG. 19 shows that 500 ng/mL of anti-IL2 neutralizing antibody is unable to block the expansion of IL2R-CISC expressing T-cells cultured in an IL2R-CISC ligand (either rapamycin or AP21967). Peripheral blood T-cells were activated using anti-CD3/CD28 beads, transduced with IL2R-CISC V3 lentivirus, and expanded in the indicated IL2R-CISC ligand plus anti-IL2 antibody. Use of the anti-IL2 antibody did not inhibit expansion of the T-cells, demonstrating that the IL2R-CISC acts cell autonomously to provide a growth signal.

The IL2R-CISC cells were exposed to an IL-2 neutralizing antibody, which neutralized the growth and proliferation of cells (FIGS. 18 and 19). This indicates that the CISC-induced expansion is not due to autocrine or paracrine stimulation.

Figure 20:
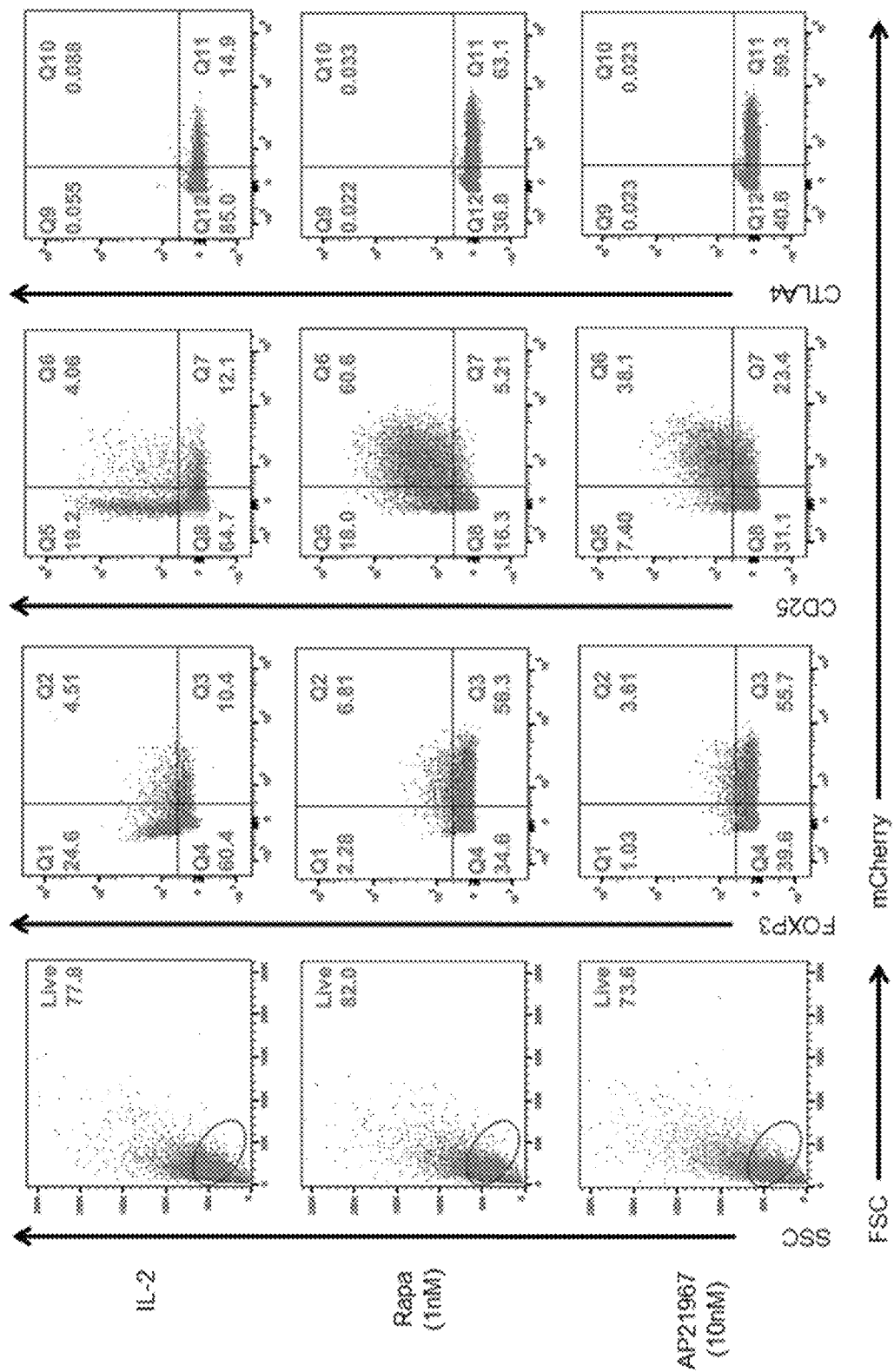
FIG. 20 shows a FACS assay that is a T-cell marker analysis for CISC V3 expanded cells. Peripheral blood T-cells were activated using anti-CD3/CD28 beads transduced with IL2R-CISC V3 lentivirus, expanded in IL-2 or the indicated IL2R-CISC ligand for 15 days. Cells expanded in IL-2 have generally low expression of CD25, the IL2R alpha subunit, reflecting IL2R turnover in response to IL-2. In contrast, cells expanded through their IL2R-CISC receptors have high CD25 expression, as low media IL-2 promotes minimal turnover of native IL2R.

The IL2-CISC induced signaling pathways were analyzed to determine whether the magnitude of the signaling pathway is sufficient to produce clinically relevant activity. A T-Cell marker analysis for CISC V3 expanded cells was performed, as shown in the flow cell data of FIG. 20.

Figure 21:
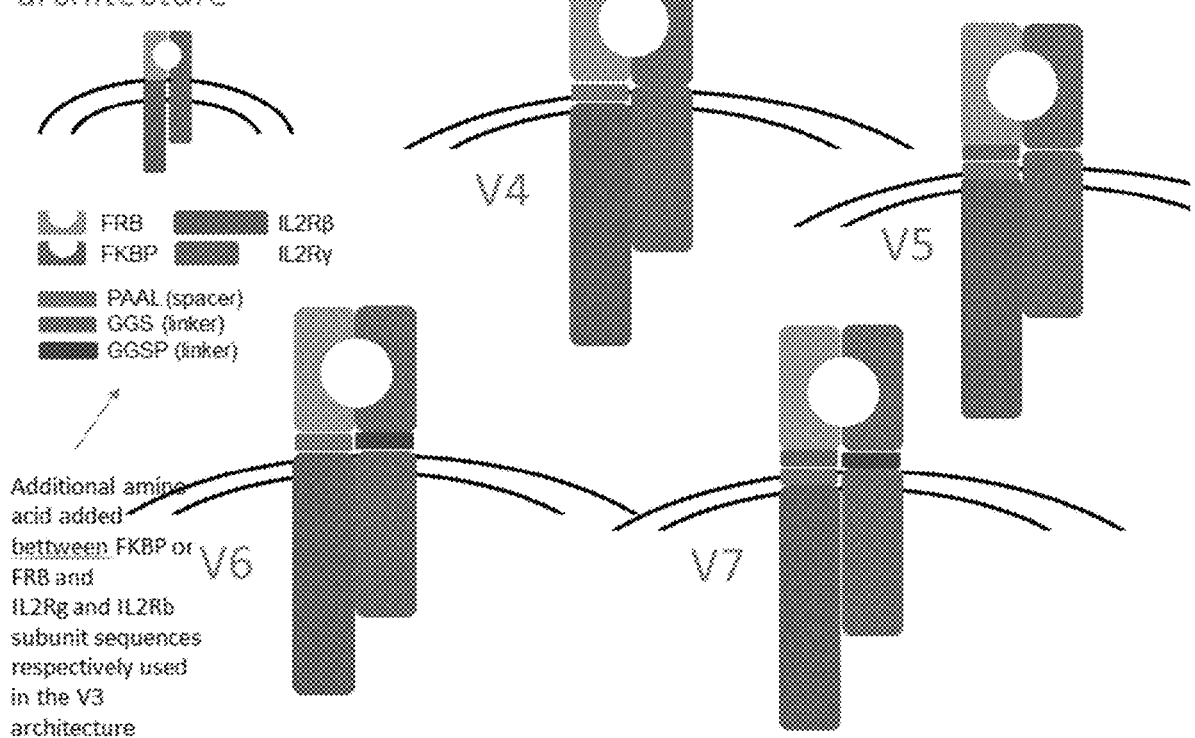
FIG. 21 shows a schematic of testing of additional CISC architectures with longer segments between IL2R components and chemical dimerizing domains (FRB, FKBP).
Figure 22:
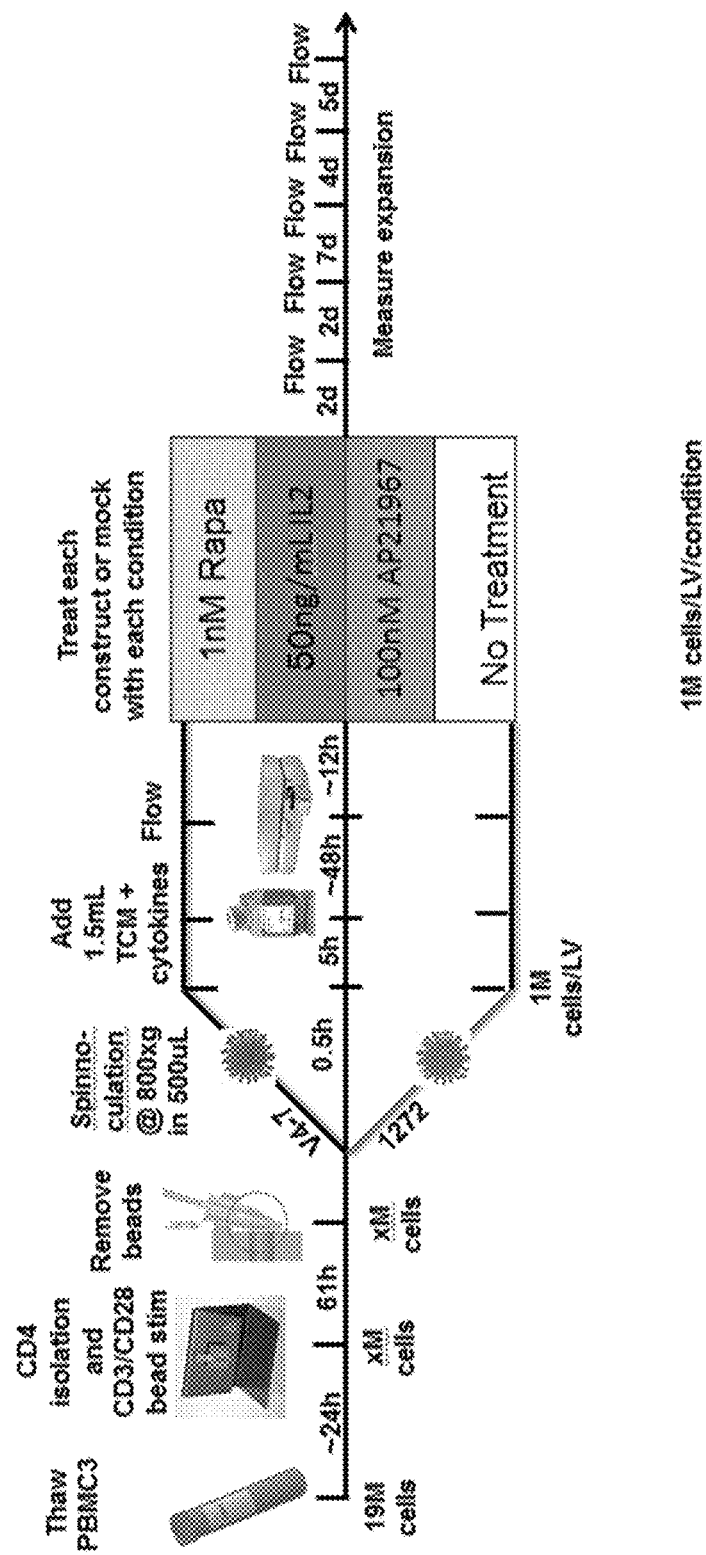
FIG. 22 shows the timeline and experimental design for treating the cells transduced by the lentiviral stock with longer IL2R-CISC linker architectures V4-V7.
Figure 23:
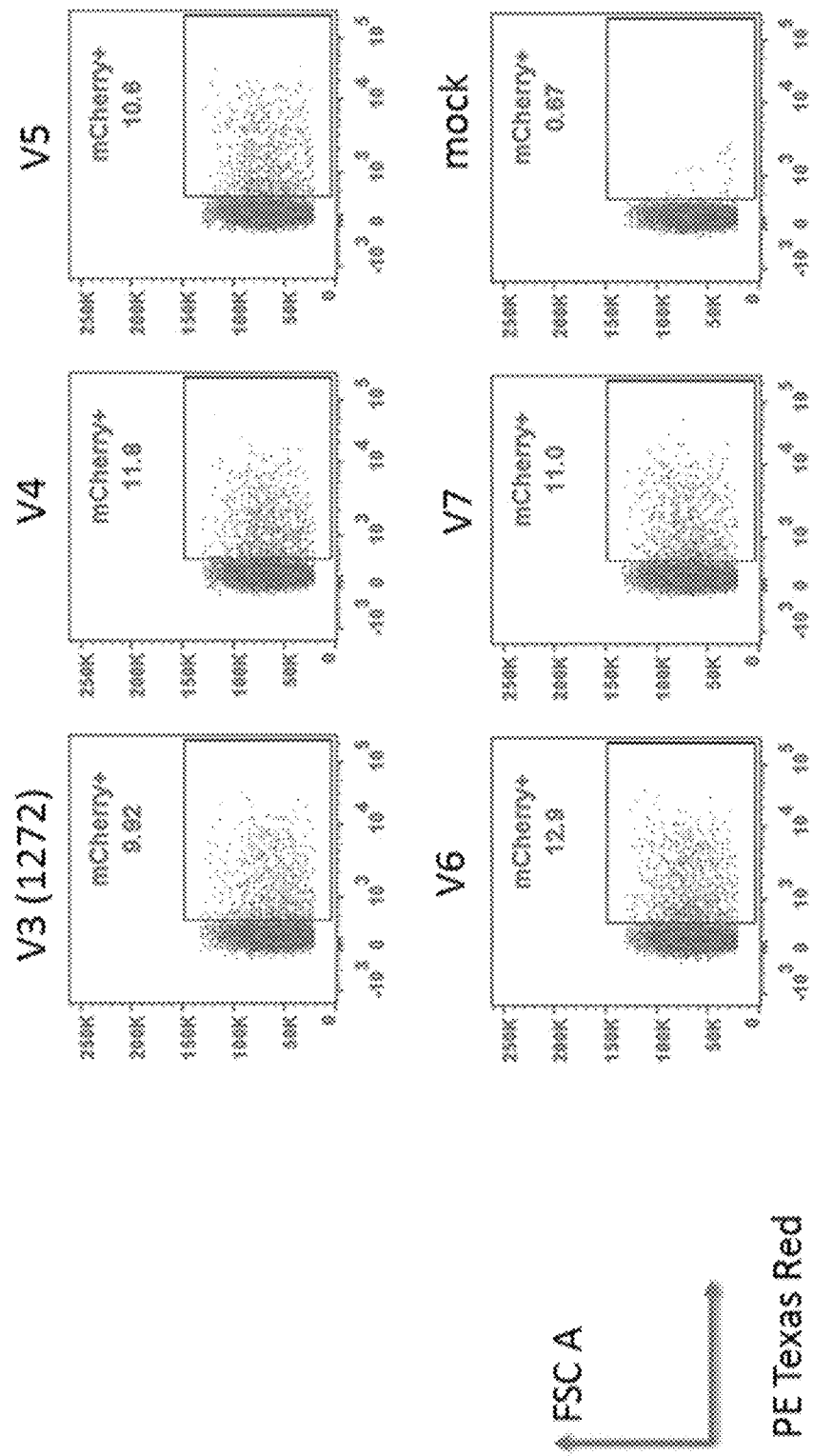
FIG. 23 shows the transduction efficiency of the lentiviral stock with longer IL2R-CISC linker architectures V4-V7 from FIG. 22.
Figure 24:
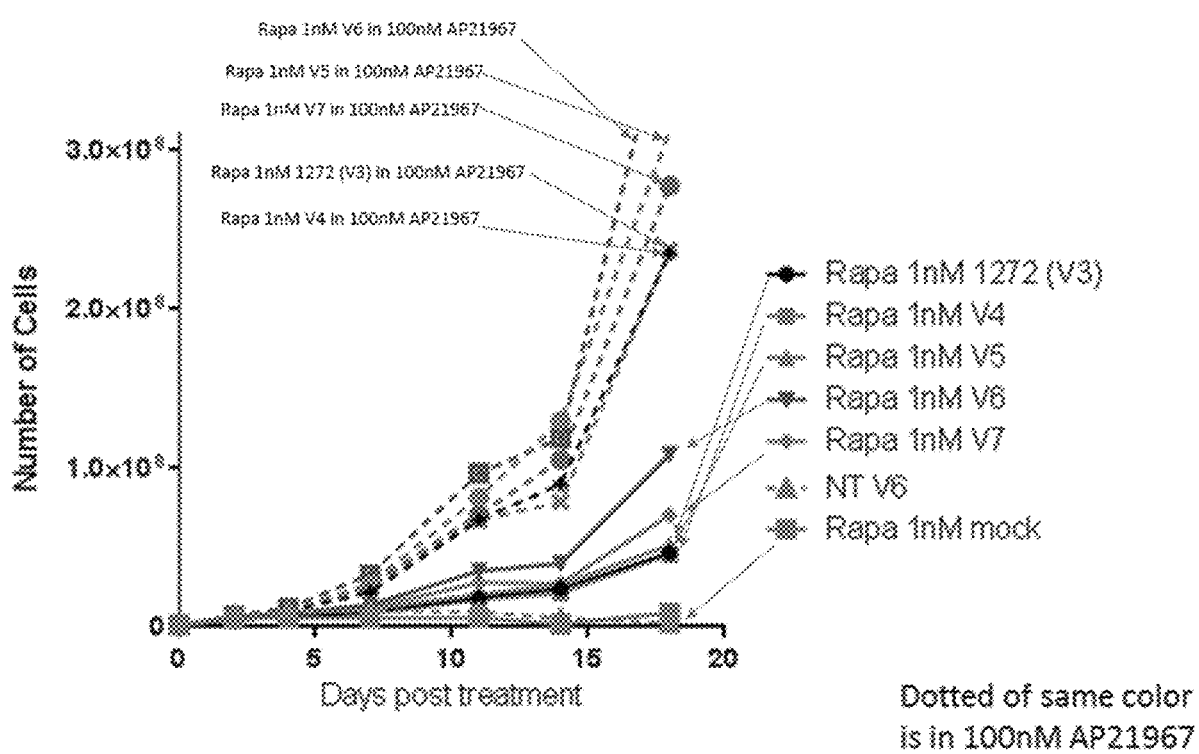
FIG. 24 shows that rapamycin-induced expansion is similar for all CISC architectures with expanded EC-domain to TM linkers. Peripheral blood T-cells were activated using anti-CD3/CD28 beads, transduced with IL2R-CISC V3-V7 lentivirus respectively, and expanded in the indicated IL2R-CISC ligand. The V3-V7 IL2R-CISC architectures were all able to induce T-cell expansion of comparable magnitude.

It is to be understood by those of skill in the art that the architectures and/or constructs described herein are not intended to be limiting. Thus, in addition to the V1, V2, and V3 constructs described herein, and other architectures and/or constructs described herein, additional architectures and/or may be used. For example, as shown in FIG. 21, additional constructs termed V4, V5, V6, and V7 were used, which included various spacers and linkers placed in the FKBP and/or FRB and IL2Rg and IL2Rb subunit sequences. The experimental protocol and design for using these comparative architectures is outlined in FIG. 22. Briefly, the method includes thawing a PBMC3 feeder cells, and CD4+ cells were isolated in the presence of anti-CD3/CD28 beads. The beads were removed, and spinoculated with one of V4, V5, V6, or V7 at 800×g in 500 µL. Following spinoculation, 1.5 mL TCM+ cytokines were added. Each construct was then treated with various conditions, including: no treatment, 100 nM AP21967, 1 nM rapamycin, or 50 ng/mL IL-2. The expansion of the cells having each construct was then measured. The expansion of the cells is shown in the flow cell data presented in FIG. 23. FIG. 24 graphically depicts the expansion of cells having the various constructs, and shows that rapamycin-induced expansion is similar for all CISC architectures tested with expanded EC-domain to TM linkers.

Figure 25:
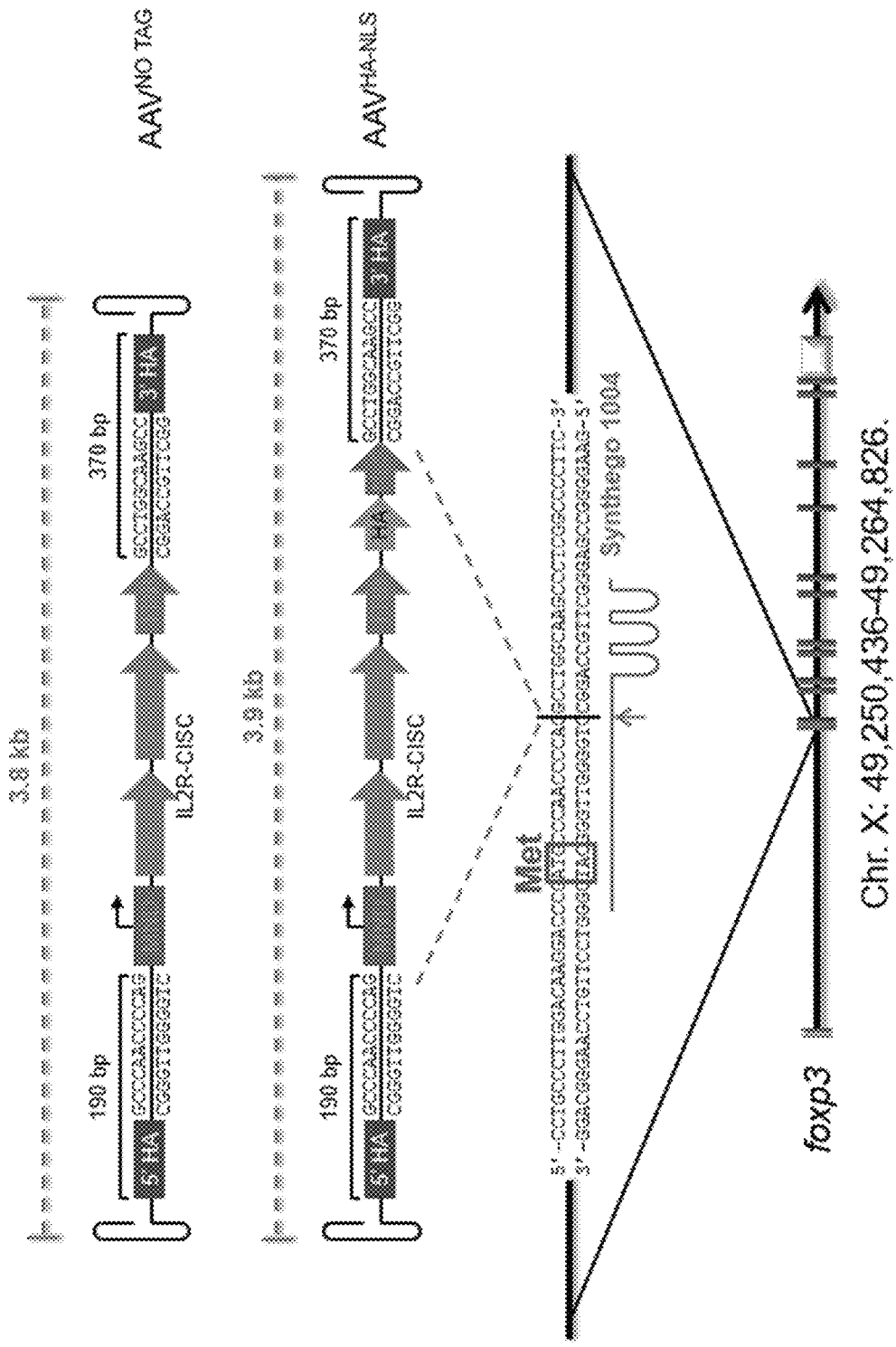
FIG. 25 shows a schematic of the Targeted knock-in of an MND promoter and CISC to enrich/expand gene targeted T-cells. The described targeting approach integrates a promoter and both components of an IL2R-CISC V3 into the FOXP3 locus in line with a GFP fusion to the native FOXP3 gene. This architecture is intended to allow for ligand-induced selection of cells which have undergone an accurate gene targeting event.
Figure 26:
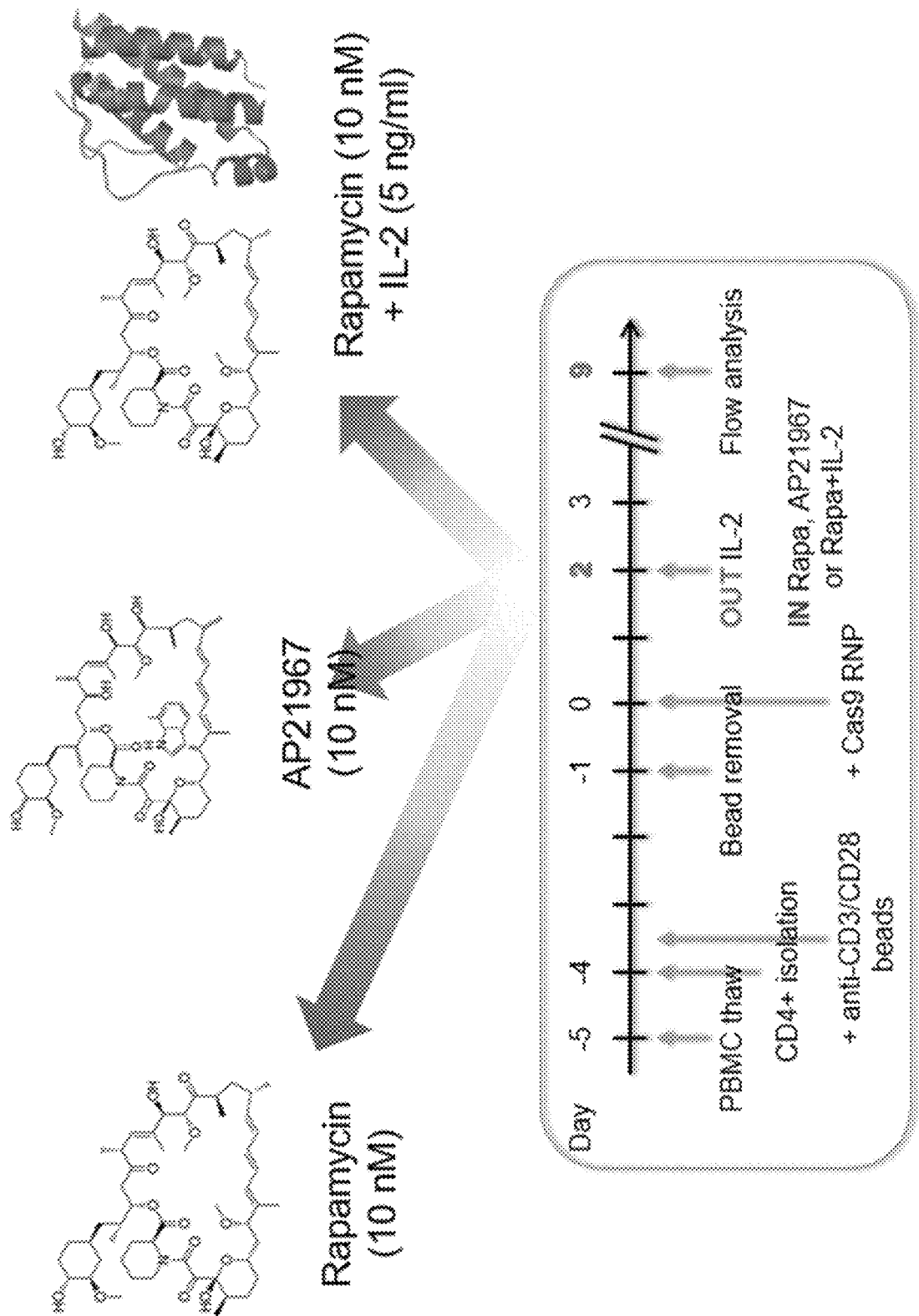
FIG. 26 depicts a schematic diagram showing an experimental design of targeted knock-in of MND promoter and CISC. This represents an experimental schematic of how a CRISP/Cas9 nuclease is used to induce targeted integration of the cassettes from FIG. 25 into the FOXP3 locus, followed by expansion of the gene targeted cells in the indicated IL2R-CISC ligand.
Figure 27:
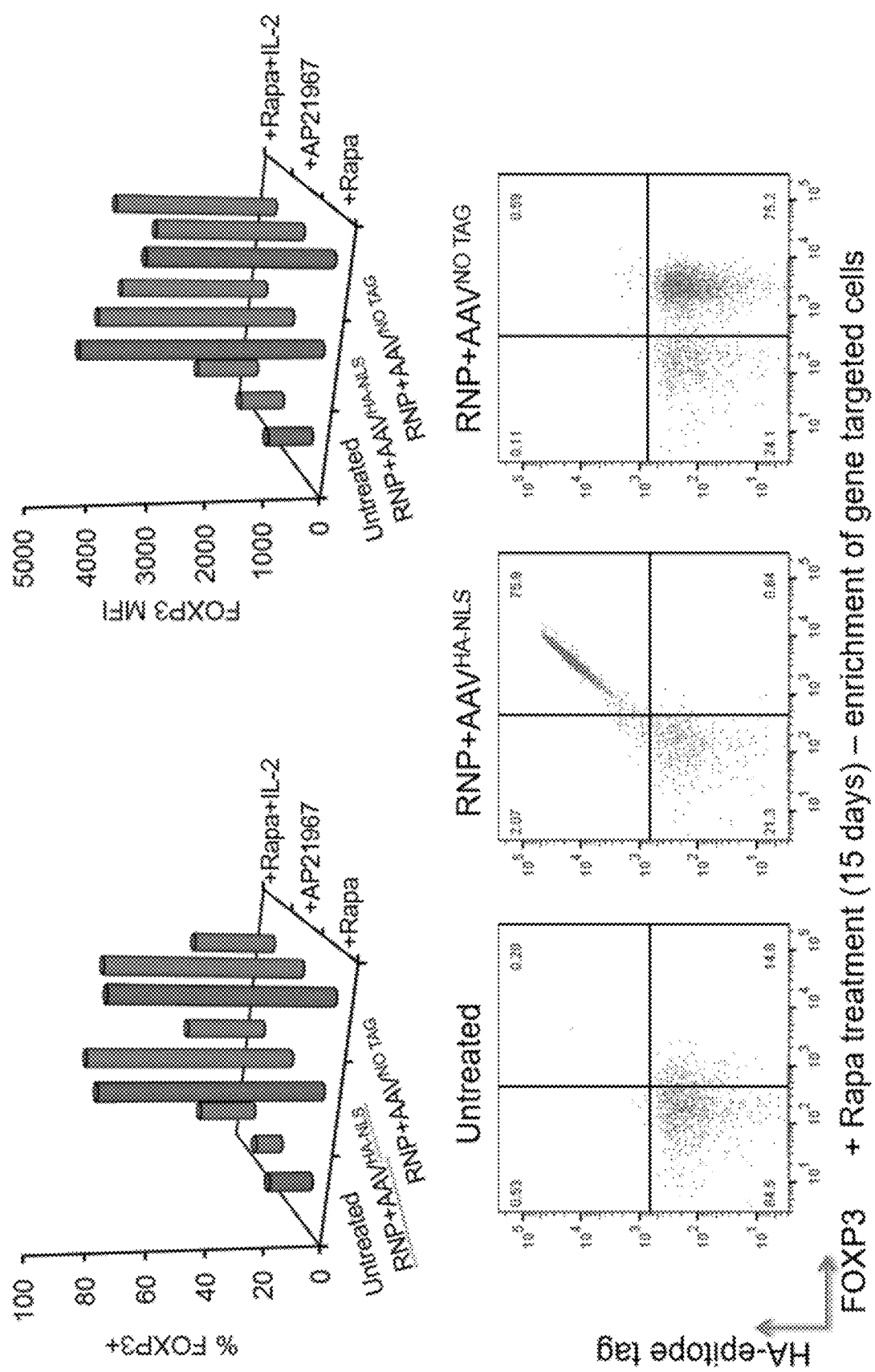
FIG. 27 shows results for targeted knock-in of MND promoter and CISC with rapamycin contact for 15 days, leading to enrichment of gene targeted cells. Following targeted integration into the FOXP3 locus utilizing the indicated approaches (no targeting, or RNP plus each of the cassettes described in FIG. 25), cells were cultured in the indicated conditions for 15 days, and then analyzed by flow cytometry for GFP-FOXP3 expression. Expansion in rapamycin or AP21967 resulted in substantial enrichment of FOXP3 expressing cells, indicating that the IL2R-CISC are able to drive ligand-induced enrichment of gene targeted cell populations, including those in which FOXP3 is overexpressed. Flow panels are representative of IL2R-CISC GFP-FOXP3 expression by cells cultured in rapamycin.
Figure 28:
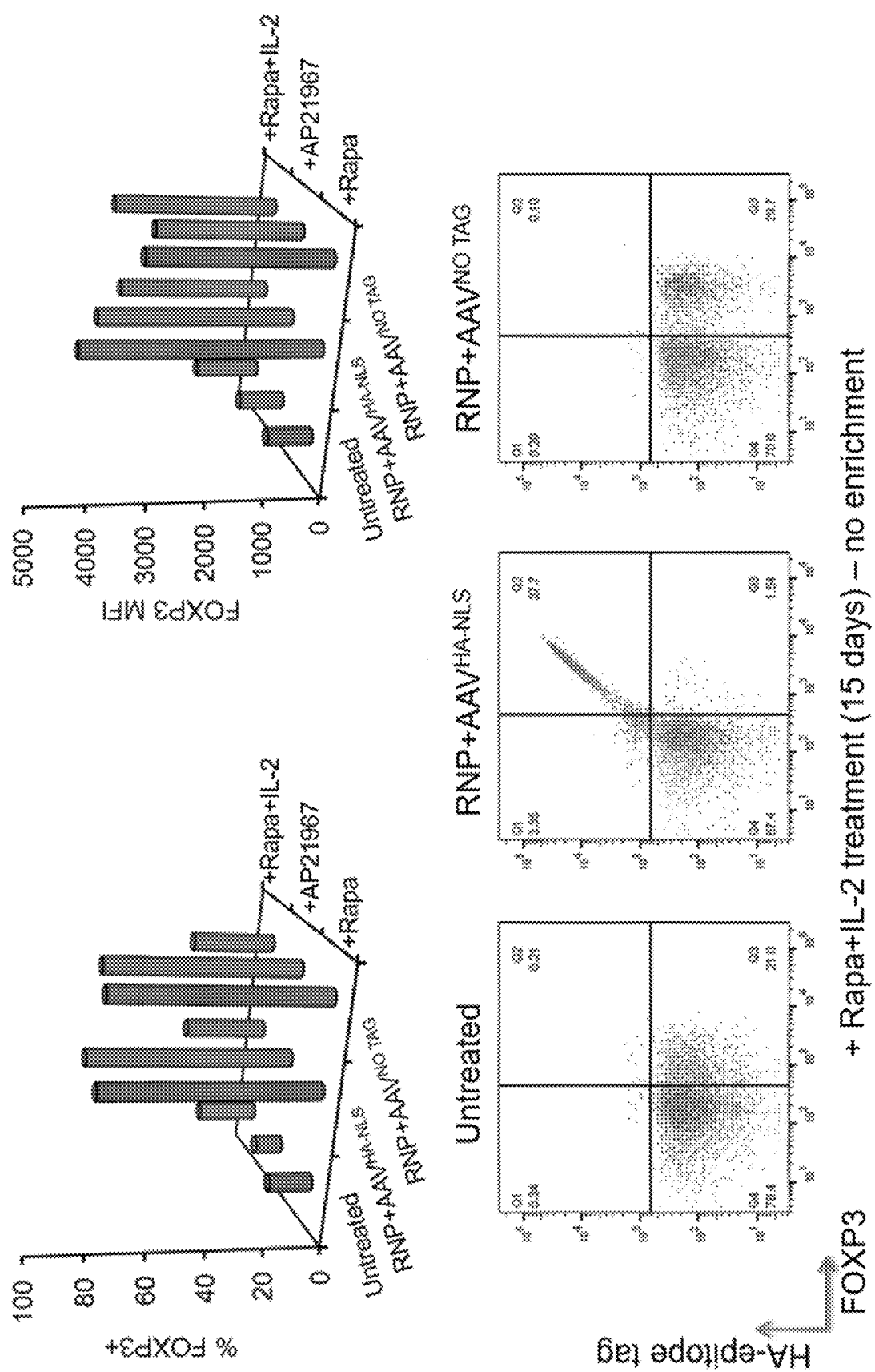
FIG. 28 shows results for targeted knock-in of MND promoter and CISC, with rapamycin+IL-2 contact for 15 days, resulting in no enrichment of gene targeted cells. Following targeted integration into the FOXP3 locus utilizing the indicated approaches, cells were cultured in the indicated conditions for 15 days, and then analyzed by flow cytometry for GFP-FOXP3 expression. Expansion in rapamycin+IL2 resulted in no detectable enrichment or loss of FOXP3 expressing cells vs untreated cells, indicating that the IL2R-CISC does not detrimentally affect the function of FOXP3 overexpressing cells. Flow panels are representative of IL2R-CISC GFP-FOXP3 expression by cells cultured in IL-2+ rapamycin.

In addition, the targeted knock-in of MND promoter and CISC was tested to enrich and/or expand gene targeted T cells. FIG. 25 shows the gene constructs for the targeted knock-in of the MND promoter, and FIG. 26 graphically depicts one embodiment of the method protocol used for the targeted knock-in. Briefly, PBMC feeder cells were thawed and CD4+ cells were isolated in the presence of anti-CD3/CD28 beads. The beads were removed and Cas9/gRNA ribonucleoproteins (RNPs) were added. The construct was then treated with various conditions, including: no treatment, 10 nM AP21967, 10 nM rapamycin, or 10 nM rapamycin+5 ng/mL IL-2. As shown in FIGS. 27 and 28, contact with rapamycin resulted in enrichment of gene targeted cells, whereas contact with rapamycin and IL-2 showed no enrichment.

The present disclosure has been described above with reference to specific alternatives. However, other alternatives than the above described are equally possible within the scope of the disclosure. Different method steps than those described above, may be provided within the scope of the disclosure. The different features and steps described herein may be combined in other combinations than those described.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those of skill within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

In addition, where features or aspects of the disclosure are described in terms of Markush groups, those skilled in the art will recognize that the disclosure is also thereby described in terms of any individual member or subgroup of members of the Markush group.

Any of the features of an alternative of the first through eleventh aspects is applicable to all aspects and alternatives identified herein. Moreover, any of the features of an alternative of the first through eleventh aspects is independently combinable, partly or wholly with other alternatives described herein in any way, e.g., one, two, or three or more alternatives may be combinable in whole or in part. Further, any of the features of an alternative of the first through eleventh aspects may be made optional to other aspects or alternatives. Although described above in terms of various example alternatives and implementations, it should be understood that the various features, aspects and functionality described in one or more of the individual alternatives are not limited in their applicability to the particular alternative with which they are described, but instead may be applied, alone or in various combinations, to one or more of the other alternatives of the present application, whether or not such alternatives are described and whether or not such features are presented as being a part of a described alternative. Thus, the breadth and scope of the present application should not be limited by any of the above-described example alternatives.

All references cited herein are incorporated herein by reference in their entirety. To the extent publications and patents or patent applications incorporated by reference contradict the disclosure contained in the specification, the specification is intended to supersede and/or take precedence over any such contradictory material. To the extent publications and patents or patent applications incorporated by reference herein contradict the disclosure contained in the specification, the specification is intended to supersede and/or take precedence over any such contradictory material.

What is claimed is:

1. A system for expression of a dimerization activatable chemical-induced signaling complex (CISC) in a cell, comprising:
a first polynucleotide sequence encoding a first polypeptide component of the CISC, and a second polynucleotide sequence encoding a second polypeptide component of the CISC, operatively linked to at least one promoter,
wherein the first polypeptide component comprises, in N-to-C terminal order, an extracellular domain comprising an FK506-binding protein (FKBP) domain, an IL-2 receptor γ (IL2Rγ) transmembrane domain, and an IL2Rγ cytoplasmic signaling domain;
wherein the second polypeptide component comprises, in N-to-C terminal order, an extracellular domain comprising an FKBP-rapamycin-binding (FRB) domain, an IL-2 receptor β (IL2Rβ) transmembrane domain, and an IL2Rβ cytoplasmic signaling domain.

2. The system of claim 1, wherein the first polypeptide component comprises an amino acid sequence having at least 95% sequence identity to amino acids 21-251 of SEQ ID NO: 1.

3. The system of claim 2, wherein the second polypeptide component comprises an amino acid sequence having at least 95% sequence identity to amino acids 22-429 of SEQ ID NO: 2.

4. The system of claim 1, wherein the first polypeptide component comprises an amino acid sequence as set forth in amino acids 21-251 of SEQ ID NO: 1.

5. The system of claim 4, wherein the second polypeptide component comprises an amino acid sequence as set forth in amino acids 22-429 of SEQ ID NO: 2.

6. The system of claim 1, wherein the first polynucleotide sequence and the second polynucleotide sequence are comprised in a viral vector.

7. The system of claim 6, wherein the viral vector is a lentiviral vector.

8. The system of claim 6, wherein the viral vector in an adeno-associated virus (AAV) vector.

9. The system of claim 6, wherein the first polypeptide component comprises an amino acid sequence having at least 95% sequence identity to amino acids 21-251 of SEQ ID NO: 1.

10. The system of claim 9, wherein the second polypeptide component comprises an amino acid sequence having at least 95% sequence identity to amino acids 22-429 of SEQ ID NO: 2.

11. A cell comprising the first polynucleotide sequence and the second polynucleotide sequence of the system of claim 1.

12. The cell of claim 11, wherein the cell is a cytotoxic lymphocyte.

13. The cell of claim 12, wherein the first polypeptide component comprises an amino acid sequence having at least 95% sequence identity to amino acids 21-251 of SEQ ID NO: 1.

14. The cell of claim 13, wherein the second polypeptide component comprises an amino acid sequence having at least 95% sequence identity to amino acids 22-429 of SEQ ID NO: 2.

15. The cell of claim 11, wherein the cell is a cytotoxic T lymphocyte.

16. The cell of claim 11, wherein the cell is a regulatory T lymphocyte ($T_{reg}$).

17. The system of claim 1, wherein the first polypeptide component of the CISC comprises an amino acid sequence having at least 95% sequence identity to any one of:
(1) amino acids 21-251 of SEQ ID NO: 1;
(2) amino acids 21-352 of SEQ ID NO: 3;
(3) amino acids 21-349 of SEQ ID NO: 5; or
(4) amino acids 21-251 of SEQ ID NO: 7, and wherein the second polypeptide component of the CISC comprises an amino acid sequence having at least 95% sequence identity to any one of:
(1) amino acids 22-429 of SEQ ID NO: 2;
(2) amino acids 22-544 of SEQ ID NO: 4;
(3) amino acids 22-541 of SEQ ID NO: 6; or
(4) amino acids 22-379 of SEQ ID NO: 8.

18. The system of claim 17, wherein the first polypeptide component of the CISC comprises the amino acid sequence of any one of:
(1) amino acids 21-251 of SEQ ID NO: 1;
(2) amino acids 21-352 of SEQ ID NO: 3;
(3) amino acids 21-349 of SEQ ID NO: 5; or
(4) amino acids 21-251 of SEQ ID NO: 7.

19. The system of claim 17, wherein the second polypeptide component of the CISC comprises the amino acid sequence of any one of:
(1) amino acids 22-429 of SEQ ID NO: 2;
(2) amino acids 22-544 of SEQ ID NO: 4;
(3) amino acids 22-541 of SEQ ID NO: 6; or
(4) amino acids 22-379 of SEQ ID NO: 8.

20. The system of claim 17 comprising the first polynucleotide sequence and the second polynucleotide sequence in a vector.

21. The system of claim 20, wherein the vector is a viral vector.

22. The system of claim 21, wherein the viral vector is selected from a lentiviral vector and an adeno-associated virus (AAV) vector.

23. A cell comprising the first polynucleotide sequence and the second polynucleotide sequence of the system of claim 17.

24. The cell of claim 23, wherein the cell is selected from a cytotoxic lymphocyte and a regulatory T lymphocyte ($T_{reg}$).

25. A system comprising the cell of claim 23 and a ligand selected from rapamycin and a rapalog.

26. The system of claim 1, wherein the first polynucleotide sequence and the second polynucleotide sequence are comprised in separate viral vectors.

* * * * *

SEQUENCE LISTING

<160> NUMBER OF SEQ ID NOS: 20

<210> SEQ ID NO 1
<211> LENGTH: 251

```
<212> TYPE: PRT
<213> ORGANISM: Artificial Sequence
<220> FEATURE:
<223> OTHER INFORMATION: IL2R-CISC - gamma component

<400> SEQUENCE: 1

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Ser Asn Thr Ser Lys Glu Asn Pro Phe Leu Phe Ala Leu Glu Ala
    130                 135                 140

Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250

<210> SEQ ID NO 2
<211> LENGTH: 429
<212> TYPE: PRT
<213> ORGANISM: Artificial Sequence
<220> FEATURE:
<223> OTHER INFORMATION: IL2R-CISC - beta component

<400> SEQUENCE: 2

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80
```

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Gly Lys Asp Thr Ile Pro Trp Leu Gly His Leu Leu Val Gly
        115                 120                 125

Leu Ser Gly Ala Phe Gly Phe Ile Ile Leu Val Tyr Leu Leu Ile Asn
    130                 135                 140

Cys Arg Asn Thr Gly Pro Trp Leu Lys Lys Val Leu Lys Cys Asn Thr
145                 150                 155                 160

Pro Asp Pro Ser Lys Phe Phe Ser Gln Leu Ser Ser Glu His Gly Gly
                165                 170                 175

Asp Val Gln Lys Trp Leu Ser Ser Pro Phe Pro Ser Ser Ser Phe Ser
            180                 185                 190

Pro Gly Gly Leu Ala Pro Glu Ile Ser Pro Leu Glu Val Leu Glu Arg
        195                 200                 205

Asp Lys Val Thr Gln Leu Leu Leu Gln Gln Asp Lys Val Pro Glu Pro
    210                 215                 220

Ala Ser Leu Ser Ser Asn His Ser Leu Thr Ser Cys Phe Thr Asn Gln
225                 230                 235                 240

Gly Tyr Phe Phe Phe His Leu Pro Asp Ala Leu Glu Ile Glu Ala Cys
                245                 250                 255

Gln Val Tyr Phe Thr Tyr Asp Pro Tyr Ser Glu Glu Asp Pro Asp Glu
            260                 265                 270

Gly Val Ala Gly Ala Pro Thr Gly Ser Ser Pro Gln Pro Leu Gln Pro
        275                 280                 285

Leu Ser Gly Glu Asp Asp Ala Tyr Cys Thr Phe Pro Ser Arg Asp Asp
    290                 295                 300

Leu Leu Leu Phe Ser Pro Ser Leu Leu Gly Gly Pro Ser Pro Pro Ser
305                 310                 315                 320

Thr Ala Pro Gly Gly Ser Gly Ala Gly Glu Glu Arg Met Pro Pro Ser
                325                 330                 335

Leu Gln Glu Arg Val Pro Arg Asp Trp Asp Pro Gln Pro Leu Gly Pro
            340                 345                 350

Pro Thr Pro Gly Val Pro Asp Leu Val Asp Phe Gln Pro Pro Pro Glu
        355                 360                 365

Leu Val Leu Arg Glu Ala Gly Glu Glu Val Pro Asp Ala Gly Pro Arg
    370                 375                 380

Glu Gly Val Ser Phe Pro Trp Ser Arg Pro Pro Gly Gln Gly Glu Phe
385                 390                 395                 400

Arg Ala Leu Asn Ala Arg Leu Pro Leu Asn Thr Asp Ala Tyr Leu Ser
                405                 410                 415

Leu Gln Glu Leu Gln Gly Gln Asp Pro Thr His Leu Val
            420                 425

<210> SEQ ID NO 3
<211> LENGTH: 352
<212> TYPE: PRT
<213> ORGANISM: Artificial Sequence
<220> FEATURE:
<223> OTHER INFORMATION: FKBP IL2Rg CISC 1210

<400> SEQUENCE: 3

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
 50                  55                  60

Pro Phe Lys Phe Met Leu Gly Lys Gln Glu Val Ile Arg Gly Trp Glu
 65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Gly Ser Gln Asn Leu Val Ile Pro Trp Ala Pro Glu Asn Leu Thr
130                 135                 140

Leu His Lys Leu Ser Glu Ser Gln Leu Glu Leu Asn Trp Asn Asn Arg
145                 150                 155                 160

Phe Leu Asn His Cys Leu Glu His Leu Val Gln Tyr Arg Thr Asp Trp
                165                 170                 175

Asp His Ser Trp Thr Glu Gln Ser Val Asp Tyr Arg His Lys Phe Ser
            180                 185                 190

Leu Pro Ser Val Asp Gly Gln Lys Arg Tyr Thr Phe Arg Val Arg Ser
        195                 200                 205

Arg Phe Asn Pro Leu Cys Gly Ser Ala Gln His Trp Ser Glu Trp Ser
210                 215                 220

His Pro Ile His Trp Gly Ser Asn Thr Ser Lys Glu Asn Pro Phe Leu
225                 230                 235                 240

Phe Ala Leu Glu Ala Val Val Ile Ser Val Gly Ser Met Gly Leu Ile
                245                 250                 255

Ile Ser Leu Leu Cys Val Tyr Phe Trp Leu Glu Arg Thr Met Pro Arg
            260                 265                 270

Ile Pro Thr Leu Lys Asn Leu Glu Asp Leu Val Thr Glu Tyr His Gly
        275                 280                 285

Asn Phe Ser Ala Trp Ser Gly Val Ser Lys Gly Leu Ala Glu Ser Leu
290                 295                 300

Gln Pro Asp Tyr Ser Glu Arg Leu Cys Leu Val Ser Glu Ile Pro Pro
305                 310                 315                 320

Lys Gly Gly Ala Leu Gly Glu Gly Pro Gly Ala Ser Pro Cys Asn Gln
                325                 330                 335

His Ser Pro Tyr Trp Ala Pro Pro Cys Tyr Thr Leu Lys Pro Glu Thr
            340                 345                 350

<210> SEQ ID NO 4
<211> LENGTH: 544
<212> TYPE: PRT
<213> ORGANISM: Artificial Sequence
<220> FEATURE:
<223> OTHER INFORMATION: FRB IL2Rb CISC 1210

<400> SEQUENCE: 4

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

```
Glu Glu Ala Ser Arg Leu Tyr Phe Gly Glu Arg Asn Val Lys Gly Met
             35                  40                  45

Phe Glu Val Leu Glu Pro Leu His Ala Met Met Glu Arg Gly Pro Gln
 50                  55                  60

Thr Leu Lys Glu Thr Ser Phe Asn Gln Ala Tyr Gly Arg Asp Leu Met
 65                  70                  75                  80

Glu Ala Gln Glu Trp Cys Arg Lys Tyr Met Lys Ser Gly Asn Val Lys
                 85                  90                  95

Asp Leu Leu Gln Ala Trp Asp Leu Tyr Tyr His Val Phe Arg Arg Ile
                100                 105                 110

Ser Lys Gly Gly Ser Lys Pro Phe Glu Asn Leu Arg Leu Met Ala Pro
            115                 120                 125

Ile Ser Leu Gln Val Val His Val Glu Thr His Arg Cys Asn Ile Ser
130                 135                 140

Trp Glu Ile Ser Gln Ala Ser His Tyr Phe Glu Arg His Leu Glu Phe
145                 150                 155                 160

Glu Ala Arg Thr Leu Ser Pro Gly His Thr Trp Glu Ala Pro Leu
                165                 170                 175

Leu Thr Leu Lys Gln Lys Gln Glu Trp Ile Cys Leu Glu Thr Leu Thr
                180                 185                 190

Pro Asp Thr Gln Tyr Glu Phe Gln Val Arg Val Lys Pro Leu Gln Gly
            195                 200                 205

Glu Phe Thr Thr Trp Ser Pro Trp Ser Gln Pro Leu Ala Phe Arg Thr
            210                 215                 220

Lys Pro Ala Ala Leu Gly Lys Asp Thr Ile Pro Trp Leu Gly His Leu
225                 230                 235                 240

Leu Val Gly Leu Ser Gly Ala Phe Gly Phe Ile Ile Leu Val Tyr Leu
                245                 250                 255

Leu Ile Asn Cys Arg Asn Thr Gly Pro Trp Leu Lys Lys Val Leu Lys
            260                 265                 270

Cys Asn Thr Pro Asp Pro Ser Lys Phe Phe Ser Gln Leu Ser Ser Glu
            275                 280                 285

His Gly Gly Asp Val Gln Lys Trp Leu Ser Ser Pro Phe Pro Ser Ser
            290                 295                 300

Ser Phe Ser Pro Gly Gly Leu Ala Pro Glu Ile Ser Pro Leu Glu Val
305                 310                 315                 320

Leu Glu Arg Asp Lys Val Thr Gln Leu Leu Leu Gln Gln Asp Lys Val
                325                 330                 335

Pro Glu Pro Ala Ser Leu Ser Ser Asn His Ser Leu Thr Ser Cys Phe
            340                 345                 350

Thr Asn Gln Gly Tyr Phe Phe Phe His Leu Pro Asp Ala Leu Glu Ile
            355                 360                 365

Glu Ala Cys Gln Val Tyr Phe Thr Tyr Asp Pro Tyr Ser Glu Glu Asp
370                 375                 380

Pro Asp Glu Gly Val Ala Gly Ala Pro Thr Gly Ser Ser Pro Gln Pro
385                 390                 395                 400

Leu Gln Pro Leu Ser Gly Glu Asp Asp Ala Tyr Cys Thr Phe Pro Ser
                405                 410                 415

Arg Asp Asp Leu Leu Leu Phe Ser Pro Ser Leu Leu Gly Gly Pro Ser
            420                 425                 430

Pro Pro Ser Thr Ala Pro Gly Gly Ser Gly Ala Gly Glu Glu Arg Met
            435                 440                 445
```

```
Pro Pro Ser Leu Gln Glu Arg Val Pro Arg Asp Trp Asp Pro Gln Pro
    450                 455                 460
Leu Gly Pro Pro Thr Pro Gly Val Pro Asp Leu Val Asp Phe Gln Pro
465                 470                 475                 480
Pro Pro Glu Leu Val Leu Arg Glu Ala Gly Glu Glu Val Pro Asp Ala
                485                 490                 495
Gly Pro Arg Glu Gly Val Ser Phe Pro Trp Ser Arg Pro Pro Gly Gln
                500                 505                 510
Gly Glu Phe Arg Ala Leu Asn Ala Arg Leu Pro Leu Asn Thr Asp Ala
                515                 520                 525
Tyr Leu Ser Leu Gln Glu Leu Gln Gly Gln Asp Pro Thr His Leu Val
530                 535                 540
```

<210> SEQ ID NO 5
<211> LENGTH: 349
<212> TYPE: PRT
<213> ORGANISM: Artificial Sequence
<220> FEATURE:
<223> OTHER INFORMATION: FKBP IL2Rg CISC 1211

<400> SEQUENCE: 5

```
Met Pro Leu Gly Leu Leu Trp Leu Gly Leu Ala Leu Leu Gly Ala Leu
1               5                   10                  15
His Ala Gln Ala Gly Val Gln Val Glu Thr Ile Ser Pro Gly Asp Gly
                20                  25                  30
Arg Thr Phe Pro Lys Arg Gly Gln Thr Cys Val Val His Tyr Thr Gly
                35                  40                  45
Met Leu Glu Asp Gly Lys Lys Phe Asp Ser Ser Arg Asp Arg Asn Lys
    50                  55                  60
Pro Phe Lys Phe Met Leu Gly Lys Gln Glu Val Ile Arg Gly Trp Glu
65                  70                  75                  80
Glu Gly Val Ala Gln Met Ser Val Gly Gln Arg Ala Lys Leu Thr Ile
                85                  90                  95
Ser Pro Asp Tyr Ala Tyr Gly Ala Thr Gly His Pro Gly Ile Ile Pro
                100                 105                 110
Pro His Ala Thr Leu Val Phe Asp Val Glu Leu Leu Lys Leu Glu Gly
            115                 120                 125
Gln Asn Leu Val Ile Pro Trp Ala Pro Glu Asn Leu Thr Leu His Lys
    130                 135                 140
Leu Ser Glu Ser Gln Leu Glu Leu Asn Trp Asn Asn Arg Phe Leu Asn
145                 150                 155                 160
His Cys Leu Glu His Leu Val Gln Tyr Arg Thr Asp Trp Asp His Ser
                165                 170                 175
Trp Thr Glu Gln Ser Val Asp Tyr Arg His Lys Phe Ser Leu Pro Ser
            180                 185                 190
Val Asp Gly Gln Lys Arg Tyr Thr Phe Arg Val Arg Ser Arg Phe Asn
        195                 200                 205
Pro Leu Cys Gly Ser Ala Gln His Trp Ser Glu Trp Ser His Pro Ile
    210                 215                 220
His Trp Gly Ser Asn Thr Ser Lys Glu Asn Pro Phe Leu Phe Ala Leu
225                 230                 235                 240
Glu Ala Val Val Ile Ser Val Gly Ser Met Gly Leu Ile Ile Ser Leu
                245                 250                 255
Leu Cys Val Tyr Phe Trp Leu Glu Arg Thr Met Pro Arg Ile Pro Thr
            260                 265                 270
```

```
Leu Lys Asn Leu Glu Asp Leu Val Thr Glu Tyr His Gly Asn Phe Ser
            275                 280                 285

Ala Trp Ser Gly Val Ser Lys Gly Leu Ala Glu Ser Leu Gln Pro Asp
290                 295                 300

Tyr Ser Glu Arg Leu Cys Leu Val Ser Glu Ile Pro Pro Lys Gly Gly
305                 310                 315                 320

Ala Leu Gly Glu Gly Pro Gly Ala Ser Pro Cys Asn Gln His Ser Pro
                325                 330                 335

Tyr Trp Ala Pro Pro Cys Tyr Thr Leu Lys Pro Glu Thr
            340                 345

<210> SEQ ID NO 6
<211> LENGTH: 541
<212> TYPE: PRT
<213> ORGANISM: Artificial Sequence
<220> FEATURE:
<223> OTHER INFORMATION: FRB IL2Rb CISC 1211

<400> SEQUENCE: 6

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
                20                  25                  30

Glu Glu Ala Ser Arg Leu Tyr Phe Gly Glu Arg Asn Val Lys Gly Met
            35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Lys Pro Phe Glu Asn Leu Arg Leu Met Ala Pro Ile Ser Leu
    115                 120                 125

Gln Val Val His Val Glu Thr His Arg Cys Asn Ile Ser Trp Glu Ile
130                 135                 140

Ser Gln Ala Ser His Tyr Phe Glu Arg His Leu Glu Phe Glu Ala Arg
145                 150                 155                 160

Thr Leu Ser Pro Gly His Thr Trp Glu Glu Ala Pro Leu Leu Thr Leu
                165                 170                 175

Lys Gln Lys Gln Glu Trp Ile Cys Leu Glu Thr Leu Thr Pro Asp Thr
            180                 185                 190

Gln Tyr Glu Phe Gln Val Arg Val Lys Pro Leu Gln Gly Glu Phe Thr
    195                 200                 205

Thr Trp Ser Pro Trp Ser Gln Pro Leu Ala Phe Arg Thr Lys Pro Ala
210                 215                 220

Ala Leu Gly Lys Asp Thr Ile Pro Trp Leu Gly His Leu Leu Val Gly
225                 230                 235                 240

Leu Ser Gly Ala Phe Gly Phe Ile Ile Leu Val Tyr Leu Leu Ile Asn
                245                 250                 255

Cys Arg Asn Thr Gly Pro Trp Leu Lys Lys Val Leu Lys Cys Asn Thr
            260                 265                 270

Pro Asp Pro Ser Lys Phe Phe Ser Gln Leu Ser Ser Glu His Gly Gly
    275                 280                 285
```

-continued

Asp Val Gln Lys Trp Leu Ser Ser Pro Phe Pro Ser Ser Phe Ser
    290                 295                 300

Pro Gly Gly Leu Ala Pro Glu Ile Ser Pro Leu Glu Val Leu Glu Arg
305                 310                 315                 320

Asp Lys Val Thr Gln Leu Leu Leu Gln Asp Lys Val Pro Glu Pro
                325                 330                 335

Ala Ser Leu Ser Ser Asn His Ser Leu Thr Ser Cys Phe Thr Asn Gln
                340                 345                 350

Gly Tyr Phe Phe Phe His Leu Pro Asp Ala Leu Glu Ile Glu Ala Cys
                355                 360                 365

Gln Val Tyr Phe Thr Tyr Asp Pro Tyr Ser Glu Glu Asp Pro Asp Glu
    370                 375                 380

Gly Val Ala Gly Ala Pro Thr Gly Ser Ser Pro Gln Pro Leu Gln Pro
385                 390                 395                 400

Leu Ser Gly Glu Asp Asp Ala Tyr Cys Thr Phe Pro Ser Arg Asp Asp
                405                 410                 415

Leu Leu Leu Phe Ser Pro Ser Leu Leu Gly Gly Pro Ser Pro Pro Ser
                420                 425                 430

Thr Ala Pro Gly Gly Ser Gly Ala Gly Glu Glu Arg Met Pro Pro Ser
    435                 440                 445

Leu Gln Glu Arg Val Pro Arg Asp Trp Asp Pro Gln Pro Leu Gly Pro
    450                 455                 460

Pro Thr Pro Gly Val Pro Asp Leu Val Asp Phe Gln Pro Pro Pro Glu
465                 470                 475                 480

Leu Val Leu Arg Glu Ala Gly Glu Glu Val Pro Asp Ala Gly Pro Arg
                485                 490                 495

Glu Gly Val Ser Phe Pro Trp Ser Arg Pro Pro Gly Gln Gly Glu Phe
                500                 505                 510

Arg Ala Leu Asn Ala Arg Leu Pro Leu Asn Thr Asp Ala Tyr Leu Ser
                515                 520                 525

Leu Gln Glu Leu Gln Gly Gln Asp Pro Thr His Leu Val
                530                 535                 540

<210> SEQ ID NO 7
<211> LENGTH: 251
<212> TYPE: PRT
<213> ORGANISM: Artificial Sequence
<220> FEATURE:
<223> OTHER INFORMATION: FKBP IL2Rg CISC 1233

<400> SEQUENCE: 7

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
                20                  25                  30

Arg Thr Phe Pro Lys Arg Gly Gln Thr Cys Val Val His Tyr Thr Gly
            35                  40                  45

Met Leu Glu Asp Gly Lys Lys Phe Asp Ser Ser Arg Asp Arg Asn Lys
        50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

```
Pro His Ala Thr Leu Val Phe Asp Val Glu Leu Leu Lys Leu Glu Gly
            115                 120                 125
Gly Ser Asn Thr Ser Lys Glu Asn Pro Phe Leu Phe Ala Leu Glu Ala
        130                 135                 140
Val Val Ile Ser Val Gly Ser Met Gly Leu Ile Ile Ser Leu Leu Cys
145                 150                 155                 160
Val Tyr Phe Trp Leu Glu Arg Thr Met Pro Arg Ile Pro Thr Leu Lys
                165                 170                 175
Asn Leu Glu Asp Leu Val Thr Glu Tyr His Gly Asn Phe Ser Ala Trp
            180                 185                 190
Ser Gly Val Ser Lys Gly Leu Ala Glu Ser Leu Gln Pro Asp Tyr Ser
        195                 200                 205
Glu Arg Leu Cys Leu Val Ser Glu Ile Pro Pro Lys Gly Gly Ala Leu
210                 215                 220
Gly Glu Gly Pro Gly Ala Ser Pro Cys Asn Gln His Ser Pro Tyr Trp
225                 230                 235                 240
Ala Pro Pro Cys Tyr Thr Leu Lys Pro Glu Thr
                245                 250

<210> SEQ ID NO 8
<211> LENGTH: 379
<212> TYPE: PRT
<213> ORGANISM: Artificial Sequence
<220> FEATURE:
<223> OTHER INFORMATION: FRB IL2Rb CISC 1233

<400> SEQUENCE: 8

Met Ala Leu Pro Val Thr Ala Leu Leu Leu Pro Leu Ala Leu Leu Leu
1               5                   10                  15
His Ala Ala Arg Pro Ile Leu Trp His Glu Met Trp His Glu Gly Leu
            20                  25                  30
Glu Glu Ala Ser Arg Leu Tyr Phe Gly Glu Arg Asn Val Lys Gly Met
        35                  40                  45
Phe Glu Val Leu Glu Pro Leu His Ala Met Met Glu Arg Gly Pro Gln
    50                  55                  60
Thr Leu Lys Glu Thr Ser Trp Leu Gly His Leu Leu Val Gly Leu Ser
65                  70                  75                  80
Gly Ala Phe Gly Phe Ile Ile Leu Val Tyr Leu Leu Ile Asn Cys Arg
                85                  90                  95
Asn Thr Gly Pro Trp Leu Lys Lys Val Leu Lys Cys Asn Thr Pro Asp
            100                 105                 110
Pro Ser Lys Phe Phe Ser Gln Leu Ser Ser Glu His Gly Gly Asp Val
        115                 120                 125
Gln Lys Trp Leu Ser Ser Pro Phe Pro Ser Ser Ser Phe Ser Pro Gly
    130                 135                 140
Gly Leu Ala Pro Glu Ile Ser Pro Leu Glu Val Leu Glu Arg Asp Lys
145                 150                 155                 160
Val Thr Gln Leu Leu Leu Gln Gln Asp Lys Val Pro Glu Pro Ala Ser
                165                 170                 175
Leu Ser Ser Asn His Ser Leu Thr Ser Cys Phe Thr Asn Gln Gly Tyr
            180                 185                 190
Phe Phe Phe His Leu Pro Asp Ala Leu Glu Ile Glu Ala Cys Gln Val
        195                 200                 205
Tyr Phe Thr Tyr Asp Pro Tyr Ser Glu Glu Asp Pro Asp Glu Gly Val
    210                 215                 220
```

Ala Gly Ala Pro Thr Gly Ser Ser Pro Gln Pro Leu Gln Pro Leu Ser
225                 230                 235                 240

Gly Glu Asp Asp Ala Tyr Cys Thr Phe Pro Ser Arg Asp Asp Leu Leu
            245                 250                 255

Leu Phe Ser Pro Ser Leu Leu Gly Gly Pro Ser Pro Pro Ser Thr Ala
        260                 265                 270

Pro Gly Gly Ser Gly Ala Gly Glu Glu Arg Met Pro Pro Ser Leu Gln
    275                 280                 285

Glu Arg Val Pro Arg Asp Trp Asp Pro Gln Pro Leu Gly Pro Pro Thr
290                 295                 300

Pro Gly Val Pro Asp Leu Val Asp Phe Gln Pro Pro Pro Glu Leu Val
305                 310                 315                 320

Leu Arg Glu Ala Gly Glu Glu Val Pro Asp Ala Gly Pro Arg Glu Gly
            325                 330                 335

Val Ser Phe Pro Trp Ser Arg Pro Pro Gly Gln Gly Glu Phe Arg Ala
        340                 345                 350

Leu Asn Ala Arg Leu Pro Leu Asn Thr Asp Ala Tyr Leu Ser Leu Gln
    355                 360                 365

Glu Leu Gln Gly Gln Asp Pro Thr His Leu Val
370                 375

<210> SEQ ID NO 9
<211> LENGTH: 345
<212> TYPE: PRT
<213> ORGANISM: Artificial Sequence
<220> FEATURE:
<223> OTHER INFORMATION: FRB IL7Ra CISC

<400> SEQUENCE: 9

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Gly Glu Ile Asn Asn Ser Ser Gly Glu Met Asp Pro Ile Leu
        115                 120                 125

Leu Thr Ile Ser Ile Leu Ser Phe Phe Ser Val Ala Leu Leu Val Ile
    130                 135                 140

Leu Ala Cys Val Leu Trp Lys Lys Arg Ile Lys Pro Ile Val Trp Pro
145                 150                 155                 160

Ser Leu Pro Asp His Lys Lys Thr Leu Glu His Leu Cys Lys Lys Pro
                165                 170                 175

Arg Lys Asn Leu Asn Val Ser Phe Asn Pro Glu Ser Phe Leu Asp Cys
            180                 185                 190

Gln Ile His Arg Val Asp Asp Ile Gln Ala Arg Asp Glu Val Glu Gly
        195                 200                 205

Phe Leu Gln Asp Thr Phe Pro Gln Gln Leu Glu Glu Ser Glu Lys Gln
    210                 215                 220

Arg Leu Gly Gly Asp Val Gln Ser Pro Asn Cys Pro Ser Glu Asp Val
225                 230                 235                 240

Val Ile Thr Pro Glu Ser Phe Gly Arg Asp Ser Ser Leu Thr Cys Leu
                245                 250                 255

Ala Gly Asn Val Ser Ala Cys Asp Ala Pro Ile Leu Ser Ser Ser Arg
            260                 265                 270

Ser Leu Asp Cys Arg Glu Ser Gly Lys Asn Gly Pro His Val Tyr Gln
        275                 280                 285

Asp Leu Leu Ser Leu Gly Thr Thr Asn Ser Thr Leu Pro Pro Pro
290                 295                 300

Phe Ser Leu Gln Ser Gly Ile Leu Thr Leu Asn Pro Val Ala Gln Gly
305                 310                 315                 320

Gln Pro Ile Leu Thr Ser Leu Gly Ser Asn Gln Glu Glu Ala Tyr Val
                325                 330                 335

Thr Met Ser Ser Phe Tyr Gln Asn Gln
            340                 345

<210> SEQ ID NO 10
<211> LENGTH: 443
<212> TYPE: PRT
<213> ORGANISM: Artificial Sequence
<220> FEATURE:
<223> OTHER INFORMATION: FKBP-F36V IL2Rb CISC

<400> SEQUENCE: 10

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Lys Asp Thr Ile Pro Trp Leu Gly His Leu Leu Val Gly Leu Ser
    130                 135                 140

Gly Ala Phe Gly Phe Ile Ile Leu Val Tyr Leu Leu Ile Asn Cys Arg
145                 150                 155                 160

Asn Thr Gly Pro Trp Leu Lys Lys Val Leu Lys Cys Asn Thr Pro Asp
                165                 170                 175

Pro Ser Lys Phe Phe Ser Gln Leu Ser Ser Glu His Gly Gly Asp Val
            180                 185                 190

Gln Lys Trp Leu Ser Ser Pro Phe Pro Ser Ser Ser Phe Ser Pro Gly
        195                 200                 205

Gly Leu Ala Pro Glu Ile Ser Pro Leu Glu Val Leu Glu Arg Asp Lys
    210                 215                 220

```
Val Thr Gln Leu Leu Leu Gln Gln Asp Lys Val Pro Glu Pro Ala Ser
225                 230                 235                 240

Leu Ser Ser Asn His Ser Leu Thr Ser Cys Phe Thr Asn Gln Gly Tyr
            245                 250                 255

Phe Phe Phe His Leu Pro Asp Ala Leu Glu Ile Glu Ala Cys Gln Val
            260                 265                 270

Tyr Phe Thr Tyr Asp Pro Tyr Ser Glu Glu Asp Pro Asp Glu Gly Val
        275                 280                 285

Ala Gly Ala Pro Thr Gly Ser Ser Pro Gln Pro Leu Gln Pro Leu Ser
    290                 295                 300

Gly Glu Asp Asp Ala Tyr Cys Thr Phe Pro Ser Arg Asp Asp Leu Leu
305                 310                 315                 320

Leu Phe Ser Pro Ser Leu Leu Gly Gly Pro Ser Pro Pro Ser Thr Ala
                325                 330                 335

Pro Gly Gly Ser Gly Ala Gly Glu Glu Arg Met Pro Pro Ser Leu Gln
            340                 345                 350

Glu Arg Val Pro Arg Asp Trp Asp Pro Gln Pro Leu Gly Pro Pro Thr
        355                 360                 365

Pro Gly Val Pro Asp Leu Val Asp Phe Gln Pro Pro Pro Glu Leu Val
    370                 375                 380

Leu Arg Glu Ala Gly Glu Glu Val Pro Asp Ala Gly Pro Arg Glu Gly
385                 390                 395                 400

Val Ser Phe Pro Trp Ser Arg Pro Pro Gly Gln Gly Glu Phe Arg Ala
                405                 410                 415

Leu Asn Ala Arg Leu Pro Leu Asn Thr Asp Ala Tyr Leu Ser Leu Gln
            420                 425                 430

Glu Leu Gln Gly Gln Asp Pro Thr His Leu Val
            435                 440

<210> SEQ ID NO 11
<211> LENGTH: 251
<212> TYPE: PRT
<213> ORGANISM: Artificial Sequence
<220> FEATURE:
<223> OTHER INFORMATION: FKBP-F36V IL2Rg CISC 1233

<400> SEQUENCE: 11

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Ser Asn Thr Ser Lys Glu Asn Pro Phe Leu Phe Ala Leu Glu Ala
    130                 135                 140
```

```
Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250

<210> SEQ ID NO 12
<211> LENGTH: 358
<212> TYPE: PRT
<213> ORGANISM: Artificial Sequence
<220> FEATURE:
<223> OTHER INFORMATION: FKBP-F36V IL7Ra CISC 1

<400> SEQUENCE: 12

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Glu Ile Asn Asn Ser Ser Gly Glu Met Asp Pro Ile Leu Leu Thr Ile
    130                 135                 140

Ser Ile Leu Ser Phe Phe Ser Val Ala Leu Leu Val Ile Leu Ala Cys
145                 150                 155                 160

Val Leu Trp Lys Lys Arg Ile Lys Pro Ile Val Trp Pro Ser Leu Pro
                165                 170                 175

Asp His Lys Lys Thr Leu Glu His Leu Cys Lys Lys Pro Arg Lys Asn
            180                 185                 190

Leu Asn Val Ser Phe Asn Pro Glu Ser Phe Leu Asp Cys Gln Ile His
        195                 200                 205

Arg Val Asp Asp Ile Gln Ala Arg Asp Glu Val Glu Gly Phe Leu Gln
    210                 215                 220

Asp Thr Phe Pro Gln Gln Leu Glu Glu Ser Glu Lys Gln Arg Leu Gly
225                 230                 235                 240

Gly Asp Val Gln Ser Pro Asn Cys Pro Ser Glu Asp Val Val Ile Thr
                245                 250                 255
```

```
Pro Glu Ser Phe Gly Arg Asp Ser Ser Leu Thr Cys Leu Ala Gly Asn
            260                 265                 270

Val Ser Ala Cys Asp Ala Pro Ile Leu Ser Ser Arg Ser Leu Asp
        275                 280                 285

Cys Arg Glu Ser Gly Lys Asn Gly Pro His Val Tyr Gln Asp Leu Leu
    290                 295                 300

Leu Ser Leu Gly Thr Thr Asn Ser Thr Leu Pro Pro Phe Ser Leu
305                 310                 315                 320

Gln Ser Gly Ile Leu Thr Leu Asn Pro Val Ala Gly Gln Pro Ile
                325                 330                 335

Leu Thr Ser Leu Gly Ser Asn Gln Glu Glu Ala Tyr Val Thr Met Ser
                340                 345                 350

Ser Phe Tyr Gln Asn Gln
            355

<210> SEQ ID NO 13
<211> LENGTH: 358
<212> TYPE: PRT
<213> ORGANISM: Artificial Sequence
<220> FEATURE:
<223> OTHER INFORMATION: FKBP-F36V IL7Ra CISC 2

<400> SEQUENCE: 13

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
                20                  25                  30

Arg Thr Phe Pro Lys Arg Gly Gln Thr Cys Val Val His Tyr Thr Gly
            35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Glu Ile Asn Asn Ser Ser Gly Glu Met Asp Pro Ile Leu Leu Thr Ile
    130                 135                 140

Ser Ile Leu Ser Phe Phe Ser Val Ala Leu Leu Val Ile Leu Ala Cys
145                 150                 155                 160

Val Leu Trp Lys Lys Arg Ile Lys Pro Ile Val Trp Pro Ser Leu Pro
                165                 170                 175

Asp His Lys Lys Thr Leu Glu His Leu Cys Lys Lys Pro Arg Lys Asn
            180                 185                 190

Leu Asn Val Ser Phe Asn Pro Glu Ser Phe Leu Asp Cys Gln Ile His
        195                 200                 205

Arg Val Asp Asp Ile Gln Ala Arg Asp Glu Val Glu Gly Phe Leu Gln
    210                 215                 220

Asp Thr Phe Pro Gln Gln Leu Glu Glu Ser Glu Lys Gln Arg Leu Gly
225                 230                 235                 240

Gly Asp Val Gln Ser Pro Asn Cys Pro Ser Glu Asp Val Val Ile Thr
                245                 250                 255
```

```
Pro Glu Ser Phe Gly Arg Asp Ser Ser Leu Thr Cys Leu Ala Gly Asn
            260                 265                 270

Val Ser Ala Cys Asp Ala Pro Ile Leu Ser Ser Arg Ser Leu Asp
        275                 280                 285

Cys Arg Glu Ser Gly Lys Asn Gly Pro His Val Tyr Gln Asp Leu Leu
    290                 295                 300

Leu Ser Leu Gly Thr Thr Asn Ser Thr Leu Pro Pro Pro Phe Ser Leu
305                 310                 315                 320

Gln Ser Gly Ile Leu Thr Leu Asn Pro Val Ala Gln Gly Gln Pro Ile
                325                 330                 335

Leu Thr Ser Leu Gly Ser Asn Gln Glu Glu Ala Tyr Val Thr Met Ser
            340                 345                 350

Ser Phe Tyr Gln Asn Gln
            355

<210> SEQ ID NO 14
<211> LENGTH: 276
<212> TYPE: PRT
<213> ORGANISM: Artificial Sequence
<220> FEATURE:
<223> OTHER INFORMATION: FKBP-F36V MPL

<400> SEQUENCE: 14

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
                20                  25                  30

Arg Thr Phe Pro Lys Arg Gly Gln Thr Cys Val Val His Tyr Thr Gly
            35                  40                  45

Met Leu Glu Asp Gly Lys Lys Val Asp Ser Ser Arg Asp Arg Asn Lys
50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Glu Thr Ala Trp Ile Ser Leu Val Thr Ala Leu His Leu Val Leu Gly
    130                 135                 140

Leu Ser Ala Val Leu Gly Leu Leu Leu Leu Arg Trp Gln Phe Pro Ala
145                 150                 155                 160

His Tyr Arg Arg Leu Arg His Ala Leu Trp Pro Ser Leu Pro Asp Leu
                165                 170                 175

His Arg Val Leu Gly Gln Tyr Leu Arg Asp Thr Ala Ala Leu Ser Pro
            180                 185                 190

Pro Lys Ala Thr Val Ser Asp Thr Cys Glu Glu Val Glu Pro Ser Leu
        195                 200                 205

Leu Glu Ile Leu Pro Lys Ser Ser Glu Arg Thr Pro Leu Pro Leu Cys
    210                 215                 220

Ser Ser Gln Ala Gln Met Asp Tyr Arg Arg Leu Gln Pro Ser Cys Leu
225                 230                 235                 240

Gly Thr Met Pro Leu Ser Val Cys Pro Pro Met Ala Glu Ser Gly Ser
                245                 250                 255
```

Cys Cys Thr Thr His Ile Ala Asn His Ser Tyr Leu Pro Leu Ser Tyr
            260                 265                 270

Trp Gln Gln Pro
        275

<210> SEQ ID NO 15
<211> LENGTH: 4
<212> TYPE: PRT
<213> ORGANISM: Artificial Sequence
<220> FEATURE:
<223> OTHER INFORMATION: Glycine spacer 1

<400> SEQUENCE: 15

Gly Gly Gly Ser
1

<210> SEQ ID NO 16
<211> LENGTH: 7
<212> TYPE: PRT
<213> ORGANISM: Artificial Sequence
<220> FEATURE:
<223> OTHER INFORMATION: Glycine spacer 2

<400> SEQUENCE: 16

Gly Gly Gly Ser Gly Gly Gly
1               5

<210> SEQ ID NO 17
<211> LENGTH: 3
<212> TYPE: PRT
<213> ORGANISM: Artificial Sequence
<220> FEATURE:
<223> OTHER INFORMATION: Glycine spacer 3

<400> SEQUENCE: 17

Gly Gly Gly
1

<210> SEQ ID NO 18
<211> LENGTH: 10035
<212> TYPE: DNA
<213> ORGANISM: Artificial Sequence
<220> FEATURE:
<223> OTHER INFORMATION: IL2Rg upstream of IL2Rb

<400> SEQUENCE: 18
agcttaatgt agtcttatgc aatactcttg tagtcttgca acatggtaac gatgagttag      60
caacatgcct acaaggagaa gaaaaagcac cgtgcatgcc gattggtgga agtaaggtgg     120
tacgatcgtg ccttattagg aaggcaacag acgggtctga catggattgg acgaaccact     180
gaattgccgc attgcagaga tattgtattt aagtgcctag ctcgatacaa taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagacccct ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta aaggagagag atgggtgcga gagcgtcagt attaagcggg     600
gggagaatta gatcgcgatg ggaaaaaatt cggttaaggc cagggggaaa gaaaaaatat     660
aaattaaaac atatagtatg ggcaagcagg gagctagaac gattcgcagt taatcctggc     720

```
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc gctgatcttc agacctggag gaggagatat    960
gagggacaat tggagaagtg aattatataa atataaagta gtaaaaattg aaccattagg   1020
agtagcaccc accaaggcaa agagaagagt ggtgcagaga gaaaaaagag cagtgggaat   1080
aggagctttg ttccttgggt tcttgggagc agcaggaagc actatgggcg cagcctcaat   1140
gacgctgacg gtacaggcca gacaattatt gtctggtata gtgcagcagc agaacaattt   1200
gctgagggct attgaggcgc aacagcatct gttgcaactc acagtctggg gcatcaagca   1260
gctccaggca agaatcctgg ctgtggaaag ataccctaaag gatcaacagc tcctggggat   1320
ttggggttgc tctggaaaac tcatttgcac cactgctgtg ccttggaatg ctagttggag   1380
taataaatct ctggaacaga tttggaatca cacgacctgg atggagtggg acagagaaat   1440
taacaattac acaagcttaa tacactcctt aattgaagaa tcgcaaaacc agcaagaaaa   1500
gaatgaacaa gaattattgg aattagataa atgggcaagt ttgtggaatt ggtttaacat   1560
aacaaattgg ctgtggtata taaaattatt cataatgata gtaggaggct tggtaggttt   1620
aagaatagtt tttgctgtac tttctatagt gaatagagtt aggcagggat attcaccatt   1680
atcgtttcag acccacctcc caaccccgag gggacccgac aggcccgaag gaatagaaga   1740
agaaggtgga gagagagaca gagacagatc cattcgatta gtgaacggat ctcgacggta   1800
tcggttaact tttaaaagaa aagggggat tgggggtac agtgcagggg aaagaatagt   1860
agacataata gcaacagaca tacaaactaa agaattacaa aaacaaatta caaaaattca   1920
aaattttatc gatcacgaga ctagcctcga gaagcttgat atcgaattcc cacggggttg   1980
gacgcgtagg aacagagaaa caggagaata tgggccaaac aggatatctg tggtaagcag   2040
ttcctgcccc ggctcagggc caagaacagt tggaacagca gaatatgggc caaacaggat   2100
atctgtggta agcagttcct gccccggctc agggccaaga acagatggtc cccagatgcg   2160
gtcccgccct cagcagtttc tagagaacca tcagatgttt ccagggtgcc caaggacct   2220 gaaatgaccc tgtgccttat ttgaactaac caatcagttc gcttctcgct tctgttcgcg   2280
cgcttctgct ccccgagctc tatataagca gagctcgttt agtgaaccgt cagatcgcta   2340
gcaccggtgc cgccaccatg cctctgggcc tgctgtggct gggcctggcc ctgctgggcg   2400
ccctgcacgc ccaggccggc gtgcaggtgg agacaatctc cccaggcgac ggacgcacat   2460
tccctaagcg gggccagacc tgcgtggtgc actatacagg catgctggag gatggcaaga   2520
agtttgacag ctcccgggat agaaacaagc cattcaagtt tatgctgggc aagcaggaag   2580
tgatcagagg ctgggaggag ggcgtggccc agatgtctgt gggccagagg gccaagctga   2640
ccatcagccc agactacgcc tatggagcaa caggccaccc aggaatcatc ccacctcacg   2700
ccaccctggt gttcgatgtg gagctgctga agctgggcga gcaaaacttg gtgattcctt   2760
gggcccccga aaatctcacg cttcacaagt tgtccgaatc ccagctcgag ctcaactgga   2820
ataatagatt tcttaatcat tgtttggaac acctggttca atatagaacg gattgggacc   2880
actcatggac cgagcagtca gttgactacc gccacaaatt ttcacttccc agcgtagatg   2940
ggcagaagag gtacacattt agggtcagat ccaggtttaa tcctctgtgt ggttctgctc   3000
aacactggtc tgagtggagc catccgatcc actgggctc aaataccttct aaagaaaatc   3060 cgttcctctt tgcgctcgaa gccgttgtta tcagcgtcgg aagcatggga cttatcattt   3120
```

```
cccttctctg cgtgtacttc tggctggagc ggacgatgcc gcggattccg acgctcaaaa    3180
acctggagga ccttgtaaca gaatatcacg gtaatttctc cgcttggagt ggcgtatcaa    3240
aggggcttgc tgagtccctt caaccggatt actctgagcg cctctgcttg tgtccgaga     3300 tacctcccaa aggaggtgca cttggggagg gccaggcgc gtccccttgc aatcagcata     3360
gtccgtattg ggcgcccccc tgttataccc tcaaaccgga aacgggaagc ggagctacta    3420
acttcagcct gctgaagcag gctggagacg tggaggagaa ccctggacct atggcactgc    3480
ccgtgaccgc cctgctgctg cctctggccc tgctgctgca cgcagcccgg cctatcctgt    3540
ggcacgagat gtggcacgag ggcctggagg aggccagcag gctgtatttt ggcgagcgca    3600
acgtgaaggg catgttcgag gtgctggagc ctctgcacgc catgatggag agaggcccac    3660
agaccctgaa ggagacatcc tttaaccagg cctatggacg ggacctgatg gaggcacagg    3720
agtggtgcag aaagtacatg aagtctggca atgtgaagga cctgctgcag gcctgggatc    3780
tgtactatca cgtgtttcgg agaatctcca agaaaccttt tgagaacctt agactgatgg    3840
cgcccatctc tctgcaggta gttcacgttg agacccatag atgcaatata agctgggaaa    3900
tctcacaagc cagccattac tttgaacggc atttggaatt cgaggcccga acactttccc    3960
ccggtcatac gtgggaagaa gctcctctct tgacgctgaa gcagaagcag gagtggattt    4020
gtctggagac tttgactcct gatactcagt atgagttcca agttcgggtg aaaccactcc    4080
aaggcgagtt cacgacgtgg tctccgtgga gtcaaccgtt ggcgttccgc acgaagcccg    4140
ctgcccttgg caaagacacg attccgtggc ttgggcatct gctcgttggg ctgagtggtg    4200
cgtttggttt catcatcttg gtctatctct tgatcaattg cagaaataca ggcccttggc    4260 tgaaaaagt gctcaagtgt aatacccccg acccaagcaa gttcttctcc cagctttctt    4320
cagagcatgg aggcgatgtg cagaaatggc tctcttcacc ttttccctcc tcaagcttct    4380
ccccgggagg gctggcgccc gagatttcac ctcttgaggt acttgaacga gacaaggtta    4440
cccaacttct ccttcaacag gataaggtac ccgaacctgc gagccttagc tccaaccact    4500
ctcttacgag ctgcttcacc aatcagggat acttctttt ccaccttccc gatgcgctgg    4560
aaatcgaagc ttgtcaagtt tactttacct atgatccata tagcgaggaa gatcccgacg    4620
aaggagtcgc cggtgcgccc acgggttcct cacccccaacc tctccagcct ctctcaggag    4680
aagatgatgc ttattgcact ttcccagta gagacgatct cctcctcttt tctccatctc    4740
ttttgggggg accttccccc ccttctacgg cacctggcgg gtctggtgct ggcgaggagc    4800
ggatgccgcc gtccctccag gagcgagtac cacgagattg gatccccag ccacttggac    4860 cccccacccc cggcgtacct gaccttgtcg attttcaacc tcccccctgaa ttggtgctgc    4920 gagaggctgg ggaggaagtt ccggacgctg gccgaggga gggcgtgtcc tttccatgga    4980
gtaggcctcc aggtcaaggc gagtttaggg ctctcaacgc gcggctgccg ttgaatacag    5040
acgcttatct ctcactgcag gaactgcaag gtcaggaccc aacacatctt gtaggatctg    5100
gtgctactaa tttttctctt ttgaagcaag ctggagatgt tgaagagaac cctggtccag    5160
tgagcaaggg cgaggagctg ttcaccgggg tggtgcccat cctggtcgag ctggacggcg    5220
acgtaaacgg ccacaagttc agcgtgtccg gcgagggcga gggcgatgcc acctacggca    5280
agctgaccct gaagttcatc tgcaccaccg gcaagctgcc cgtgccctgg cccaccctcg    5340
tgaccaccct gacctacggc gtgcagtgct tcagccgcta ccccgaccac atgaagcagc    5400
acgacttctt caagtccgcc atgcccgaag gctacgtcca ggagcgcacc atcttcttca    5460
```

```
aggacgacgg caactacaag acccgcgccg aggtgaagtt cgagggcgac accctggtga    5520
accgcatcga gctgaagggc atcgacttca aggaggacgg caacatcctg gggcacaagc    5580
tggagtacaa ctacaacagc cacaacgtct atatcatggc cgacaagcag aagaacggca    5640
tcaaggtgaa cttcaagatc cgccacaaca tcgaggacgg cagcgtgcag ctcgccgacc    5700
actaccagca gaacaccccc atcggcgacg cccccgtgct gctgcccgac aaccactacc    5760
tgagcaccca gtccgccctg agcaaagacc ccaacgagaa gcgcgatcac atggtcctgc    5820
tggagttcgt gaccgccgcc gggatcactc tcggcatgga cgagctgtac aagtaaacta    5880
gtgtcgacaa tcaacctctg gattacaaaa tttgtgaaag attgactggt attcttaact    5940
atgttgctcc ttttacgcta tgtggatacg ctgctttaat gcctttgtat catgctattg    6000
cttcccgtat ggctttcatt ttctcctcct tgtataaatc ctggttgctg tctctttatg    6060
aggagttgtg gcccgttgtc aggcaacgtg gcgtggtgtg cactgtgttt gctgacgcaa    6120
cccccactgg ttggggcatt gccaccacct gtcagctcct ttccgggact ttcgctttcc    6180
ccctccctat tgccacggcg gaactcatcg ccgcctgcct tgcccgctgc tggacagggg    6240
ctcggctgtt gggcactgac aattccgtgg tgttgtcggg aagctgacg tccttttccat    6300 ggctgctcgc ctgtgttgcc acctggattc tgcgcgggac gtccttctgc tacgtccctt    6360
cggccctcaa tccagcggac cttccttccc gcggcctgct gccggctctg cggcctcttc    6420
cgcgtcttcg ccttcgccct cagacgagtc ggatctccct ttgggccgcc tccccgcctg    6480
gaattcgagc tcggtacctt taagaccaat gacttacaag gcagctgtag atcttagcca    6540 cttttttaaaa gaaaagggggg gactggaagg gctaattcac tcccaacgaa gacaagatct    6600 gcttttttgct tgtactgggt ctctctggtt agaccagatc tgagcctggg agctctctgg    6660
ctaactaggg aacccactgc ttaagcctca ataaagcttg ccttgagtgc ttcaagtagt    6720
gtgtgcccgt ctgttgtgtg actctggtaa ctagagatcc ctcagaccct tttagtcagt    6780
gtggaaaatc tctagcagta gtagttcatg tcatcttatt attcagtatt tataacttgc    6840
aaagaaatga atatcagaga gtgagaggaa cttgtttatt gcagcttata atggttacaa    6900
ataaagcaat agcatcacaa atttcacaaa taaagcattt ttttcactgc attctagttg    6960
tggtttgtcc aaactcatca atgtatctta tcatgtctgg ctctagctat cccgccccta    7020
actccgccca gttccgccca ttctccgccc catggctgac taattttttt tatttatgca    7080
gaggccgagg ccgcctcggc ctctgagcta ttccagaagt agtgaggagg ctttttttgga    7140 ggcctaggct tttgcgtcga gacgtaccca attcgcccta tagtgagtcg tattacgcgc    7200
gctcactggc cgtcgtttta caacgtcgtg actgggaaaa ccctggcgtt acccaactta    7260
atcgccttgc agcacatccc cctttcgcca gctggcgtaa tagcgaagag gcccgcaccg    7320 atcgccctc ccaacagttg cgcagcctga atggcgaatg gcgcgacgcg cctgtagcg    7380 gcgcattaag cgcggcgggt gtggtggtta cgcgcagcgt gaccgctaca cttgccagcg    7440
ccctagcgcc cgctcctttc gctttcttcc cttcctttct cgccacgttc gccggctttc    7500
cccgtcaagc tctaaatcgg gggctccctt tagggttccg atttagtgct ttacggcacc    7560
tcgaccccaa aaaacttgat tagggtgatg gttcacgtag tgggccatcg ccctgataga    7620
cggtttttcg ccctttgacg ttggagtcca cgttctttaa tagtggactc ttgttccaaa    7680
ctggaacaac actcaaccct atctcggtct attcttttga tttataaggg attttgccga    7740
tttcggccta ttggttaaaa aatgagctga tttaacaaaa atttaacgcg aattttaaca    7800
aaatattaac gtttacaatt tcccaggtgg cacttttcgg ggaaatgtgc gcggaacccc    7860
```

```
tatttgttta tttttctaaa tacattcaaa tatgtatccg ctcatgagac aataaccctg    7920
ataaatgctt caataatatt gaaaaaggaa gagtatgagt attcaacatt tccgtgtcgc    7980
ccttattccc tttttgcgg cattttgcct tcctgtttt gctcacccag aaacgctggt    8040
gaaagtaaaa gatgctgaag atcagttggg tgcacgagtg ggttacatcg aactggatct    8100
caacagcggt aagatccttg agagttttcg ccccgaagaa cgttttccaa tgatgagcac    8160
ttttaaagtt ctgctatgtg gcgcggtatt atcccgtatt gacgccggc aagagcaact    8220
cggtcgccgc atacactatt ctcagaatga cttggttgag tactcaccag tcacagaaaa    8280
gcatcttacg gatggcatga cagtaagaga attatgcagt gctgccataa ccatgagtga    8340
taacactgcg gccaacttac ttctgacaac gatcggagga ccgaaggagc taaccgcttt    8400
tttgcacaac atgggggatc atgtaactcg ccttgatcgt tgggaaccgg agctgaatga    8460
agccatacca aacgacgagc gtgacaccac gatgcctgta gcaatggcaa caacgttgcg    8520
caaactatta actggcgaac tacttactct agcttcccgg caacaattaa tagactggat    8580
ggaggcggat aaagttgcag gaccacttct gcgctcggcc cttccggctg gctggtttat    8640
tgctgataaa tctggagccg gtgagcgtgg gtctcgcggt atcattgcag cactggggcc    8700
agatggtaag ccctcccgta tcgtagttat ctacacgacg gggagtcagg caactatgga    8760
tgaacgaaat agacagatcg ctgagatagg tgcctcactg attaagcatt ggtaactgtc    8820
agaccaagtt tactcatata tactttagat tgatttaaaa cttcattttt aatttaaaag    8880
gatctaggtg aagatccttt ttgataatct catgaccaaa atcccttaac gtgagttttc    8940
gttccactga gcgtcagacc ccgtagaaaa gatcaaagga tcttcttgag atccttttt    9000
tctgcgcgta atctgctgct tgcaaacaaa aaaaccaccg ctaccagcgg tggtttgttt    9060
gccggatcaa gagctaccaa ctcttttcc gaaggtaact ggcttcagca gagcgcagat    9120
accaaatact gtccttctag tgtagccgta gttaggccac cacttcaaga actctgtagc    9180
accgcctaca tacctcgctc tgctaatcct gttaccagtg gctgctgcca gtggcgataa    9240
gtcgtgtctt accgggttgg actcaagacg atagttaccg gataaggcgc agcggtcggg    9300
ctgaacgggg ggttcgtgca cacagcccag cttggagcga acgacctaca ccgaactgag    9360
atacctacag cgtgagctat gagaaagcgc cacgcttccc gaagggagaa aggcggacag    9420
gtatccggta agcggcaggg tcggaacagg agagcgcacg agggagcttc caggggggaaa    9480
cgcctggtat ctttatagtc ctgtcgggtt tcgccacctc tgacttgagc gtcgattttt    9540
gtgatgctcg tcagggggc ggagcctatg gaaaaacgcc agcaacgcgg ccttttacg    9600
gttcctggcc ttttgctggc cttttgctca catgttcttt cctgcgttat cccctgattc    9660
tgtggataac cgtattaccg cctttgagtg agctgatacc gctcgccgca gccgaacgac    9720
cgagcgcagc gagtcagtga gcgaggaagc ggaagagcgc ccaatacgca aaccgcctct    9780
ccccgcgcgt tggccgattc attaatgcag ctggcacgac aggtttcccg actggaaagc    9840
gggcagtgag cgcaacgcaa ttaatgtgag ttagctcact cattaggcac cccaggcttt    9900
acactttatg cttccggctc gtatgttgtg tggaattgtg agcggataac aatttcacac    9960
aggaaacagc tatgaccatg attacgccaa gcgcgcaatt aaccctcact aaagggaaca   10020
aaagctggag ctgca                                                    10035
```

<210> SEQ ID NO 19
<211> LENGTH: 10053
<212> TYPE: DNA

<213> ORGANISM: Artificial Sequence
<220> FEATURE:
<223> OTHER INFORMATION: IL2Rg upstream of IL2Rb

<400> SEQUENCE: 19

```
agcttaatgt agtcttatgc aatactcttg tagtcttgca acatggtaac gatgagttag      60
caacatgcct tacaaggaga gaaaaagcac cgtgcatgcc gattggtgga agtaaggtgg     120
tacgatcgtg ccttattagg aaggcaacag acgggtctga catggattgg acgaaccact     180
gaattgccgc attgcagaga tattgtattt aagtgcctag ctcgatacaa taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagacccct ttagtcagtg tggaaaatct ctagcagtgg     420
cgcccgaaca gggacttgaa agcgaaaggg aaaccagagg agctctctcg acgcaggact     480
cggcttgctg aagcgcgcac ggcaagaggc gaggggcggc gactggtgag tacgccaaaa     540
attttgacta gcggaggcta aaggagaga  atgggtgcg agagcgtcag tattaagcgg     600
gggagaatta gatcgcgatg ggaaaaaatt cggttaaggc cagggggaaa gaaaaaatat     660
aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattatat aatacagtag caaccctcta ttgtgtgcat     840
caaaggatag agataaaaga caccaaggaa gctttagaca agatagagga agagcaaaac     900
aaaagtaaga ccaccgcaca gcaagcggcc gctgatcttc agacctggag gaggagatat     960
gagggacaat tggagaagtg aattatataa atataaagta gtaaaaattg aaccattagg    1020
agtagcaccc accaaggcaa agagaagagt ggtgcagaga gaaaaaagag cagtgggaat    1080
aggagctttg ttccttgggt tcttgggagc agcaggaagc actatgggcg cagcctcaat    1140
gacgctgacg gtacaggcca gacaattatt gtctggtata gtgcagcagc agaacaattt    1200
gctgagggct attgaggcgc aacagcatct gttgcaactc acagtctggg gcatcaagca    1260
gctccaggca agaatcctgg ctgtggaaag atacctaaag gatcaacagc tcctggggat    1320
ttggggttgc tctggaaaac tcatttgcac cactgctgtg ccttggaatg ctagttggag    1380
taataaatct ctggaacaga tttggaatca cacgacctgg atggagtggg acagagaaat    1440
taacaattac acaagcttaa tacactcctt aattgaagaa tcgcaaaacc agcaagaaaa    1500
gaatgaacaa gaattattgg aattagataa atgggcaagt ttgtggaatt ggtttaacat    1560
aacaaattgg ctgtggtata taaaattatt cataatgata gtaggaggct tggtaggttt    1620
aagaatagtt tttgctgtac tttctatagt gaatagagtt aggcagggat attcaccatt    1680
atcgtttcag acccacctcc caaccccgag gggacccgac aggcccgaag gaatagaaga    1740
agaaggtgga gagagagaca gagacagatc cattcgatta gtgaacggat ctcgacggta    1800
tcggttaact tttaaaagaa aagggggat  tgggggggtac agtgcagggg aaagaatagt    1860
agacataata gcaacagaca tacaaactaa agaattacaa aaacaaatta caaaaattca    1920
aaattttatc gatcacgaga ctagcctcga gaagcttgat atcgaattcc cacgggttg     1980
gacgcgtagg aacagagaaa caggagaata tgggccaaac aggatatctg tggtaagcag    2040
ttcctgcccc ggctcagggc caagaacagt tggaacagca gaatatgggc caaacaggat    2100
atctgtggta agcagttcct gccccggctc agggccaaga acagatggtc ccagatgcg     2160
gtcccgccct cagcagtttc tagagaacca tcagatgttt ccagggtgcc ccaaggacct    2220
```

```
gaaatgaccc tgtgccttat ttgaactaac caatcagttc gcttctcgct tctgttcgcg    2280
cgcttctgct ccccgagctc tatataagca gagctcgttt agtgaaccgt cagatcgcta    2340
gcaccggtgc cgccaccatg cctctgggcc tgctgtggct gggcctggcc ctgctgggcg    2400
ccctgcacgc ccaggccggc gtgcaggtgg agacaatctc cccaggcgac ggacgcacat    2460
tccctaagcg gggccagacc tgcgtggtgc actatacagg catgctggag gatggcaaga    2520
agtttgacag ctcccgggat agaaacaagc cattcaagtt tatgctgggc aagcaggaag    2580
tgatcagagg ctgggaggag ggcgtggccc agatgtctgt gggccagagg gccaagctga    2640
ccatcagccc agactacgcc tatggagcaa caggccaccc aggaatcatc ccacctcacg    2700
ccaccctggt gttcgatgtg gagctgctga agctgggcga gggcggtagt cagaaccttg    2760
tgataccatg ggccccagaa aatctcacac ttcataaact ttccgaatca caactcgaac    2820
tcaactggaa taaccggttc ctgaatcact gtcttgaaca cctggtacaa tatcggaccg    2880
actgggatca ctcatggaca gaacaatctg tggactatag cacaaattc tcactcccaa    2940 gcgtagacgg ccaaaaaaga tacactttc gcgtacgatc ccgctttaat cctctctgcg    3000
gctctgctca gcactggagt gaatggtccc atcccattca ttggggatcc aacacatcaa    3060
aagagaaccc ctttctgttc gcattggagg ccgtagtcat atctgttgga tccatgggac    3120
ttattatctc cctgttgtgt gtgtacttct ggctggaacg gactatgccc aggatcccca    3180
cgctcaagaa tctggaagat ctcgtcacag aataccatgg taatttcagc gcctggagcg    3240
gagtctctaa gggtctggcc gaatccctcc aacccgatta ttctgaacgg ttgtgcctcg    3300
tatccgaaat accaccaaaa ggcggggctc tgggtgaggg cccaggggcg agtccgtgca    3360
atcaacacag cccgtattgg gcccctcctt gttatacgtt gaagcccgaa actggaagcg    3420
gagctactaa cttcagcctg ctgaagcagg ctggagacgt ggaggagaac cctggaccta    3480
tggcactgcc cgtgaccgcc ctgctgctgc ctctggccct gctgctgcac gcagcccggc    3540
ctatcctgtg gcacgagatg tggcacgagg gcctggagga ggccagcagg ctgtattttg    3600
gcgagcgcaa cgtgaagggc atgttcgagg tgctggagcc tctgcacgcc atgatggaga    3660
gaggcccaca gaccctgaag gagacatcct taaccaggc ctatgacgg gacctgatgg    3720 aggcacagga gtggtgcaga aagtacatga agtctggcaa tgtgaaggac ctgctgcagg    3780
cctgggatct gtactatcac gtgtttcgga gaatctccaa gggaggttca aaaccttttg    3840
agaaccttag actgatggcg cccatctctc tgcaggtagt tcacgttgag acccatagat    3900
gcaatataag ctgggaaatc tcacaagcca gccattactt gaacggcat ttggaattcg    3960 aggcccgaac actttccccc ggtcatacgt gggaagaagc tcctctcttg acgctgaagc    4020
agaagcagga gtgatttgt ctggagactt tgactcctga tactcagtat gagttccaag    4080
ttcgggtgaa accactccaa ggcgagttca cgacgtggtc tccgtggagt caaccgttgg    4140
cgttccgcac gaagcccgct gcccttggca agacacgat tccgtggctt gggcatctgc    4200
tcgttgggct gagtggtgcg tttggttca tcatcttggt ctatctcttg atcaattgca    4260
gaaatacagg cccttggctg aaaaaagtgc tcaagtgtaa tacccccgac ccaagcaagt    4320
tcttctccca gctttcttca gagcatggag gcgatgtgca gaaatggctc tcttcacctt    4380
ttccctcctc aagcttctcc ccgggagggc tggcgcccga gatttcacct cttgaggtac    4440
ttgaacgaga caaggttacc caacttctcc ttcaacagga taaggtaccc gaacctgcga    4500
gccttagctc caaccactct cttacgagct gcttcaccaa tcagggatac ttcttttttcc    4560
```

```
accttcccga tgcgctggaa atcgaagctt gtcaagttta ctttacctat gatccatata    4620
gcgaggaaga tcccgacgaa ggagtcgccg gtgcgcccac gggttcctca ccccaacctc    4680
tccagcctct ctcaggagaa gatgatgctt attgcacttt tcccagtaga gacgatctcc    4740
tcctcttttc tccatctctt ttgggggggac cttcccccc ttctacggca cctggcgggt    4800
ctggtgctgg cgaggagcgg atgccgccgt ccctccagga gcgagtacca cgagattggg    4860
atccccagcc acttggaccc cccaccccg gcgtacctga ccttgtcgat tttcaacctc    4920
cccctgaatt ggtgctgcga gaggctgggg aggaagttcc ggacgctggg ccgagggagg    4980
gcgtgtcctt tccatggagt aggcctccag gtcaaggcga gtttaggggct ctcaacgcgc    5040 ggctgccgtt gaatacagac gcttatctct cactgcagga actgcaaggt caggacccaa    5100
cacatcttgt aggatctggt gctactaatt tttctctttt gaagcaagct ggagatgttg    5160
aagagaaccc tggtccagtg agcaagggcg aggagctgtt caccggggtg gtgcccatcc    5220
tggtcgagct ggacggcgac gtaaacggcc acaagttcag cgtgtccggc gagggcgagg    5280
gcgatgccac ctacggcaag ctgaccctga agttcatctg caccaccggc aagctgcccg    5340
tgccctggcc caccctcgtg accaccctga cctacggcgt gcagtgcttc agccgctacc    5400
ccgaccacat gaagcagcac gacttcttca gtccgccat gcccgaaggc tacgtccagg    5460
agcgcaccat cttcttcaag gacgacggca actacaagac ccgcgccgag gtgaagttcg    5520
agggcgacac cctggtgaac cgcatcgagc tgaagggcat cgacttcaag gaggacggca    5580
acatcctggg gcacaagctg gagtacaact acaacagcca caacgtctat atcatggccg    5640
acaagcagaa gaacggcatc aaggtgaact tcaagatccg ccacaacatc gaggacggca    5700
gcgtgcagct cgccgaccac taccagcaga acacccccat cggcgacggc cccgtgctgc    5760
tgcccgacaa ccactacctg agcacccagt ccgccctgag caaagacccc aacgagaagc    5820
gcgatcacat ggtcctgctg gagttcgtga ccgccgccgg gatcactctc ggcatggacg    5880
agctgtacaa gtaaactagt gtcgacaatc aacctctgga ttacaaaatt tgtgaaagat    5940
tgactggtat tcttaactat gttgctcctt ttacgctatg tggatacgct gctttaatgc    6000
ctttgtatca tgctattgct tcccgtatgg ctttcattt ctcctccttg tataaatcct    6060
ggttgctgtc tctttatgag gagttgtggc ccgttgtcag gcaacgtggc gtggtgtgca    6120
ctgtgtttgc tgacgcaacc cccactggtt ggggcattgc caccacctgt cagctccttt    6180
ccgggacttt cgctttcccc ctccctattg ccacggcgga actcatcgcc gcctgccttg    6240
cccgctgctg gacaggggct cggctgttgg gcactgacaa ttccgtggtg ttgtcgggga    6300
agctgacgtc ctttccatgg ctgctcgcct gtgttgccac ctggattctg cgcgggacgt    6360
ccttctgcta cgtcccttcg gccctcaatc cagcggacct tccttcccgc ggcctgctgc    6420
cggctctgcg gcctcttccg cgtcttcgcc ttcgccctca gacgagtcgg atctcccttt    6480
gggccgcctc cccgcctgga attcgagctc ggtaccttta agaccaatga cttacaaggc    6540
agctgtagat cttagccact ttttaaaaga aaaggggggga ctggaagggc taattcactc    6600
ccaacgaaga caagatctgc ttttttgcttg tactgggtct ctctggttag accagatctg    6660
agcctgggag ctctctggct aactagggaa cccactgctt aagcctcaat aaagcttgcc    6720
ttgagtgctt caagtagtgt gtgcccgtct gttgtgtgac tctggtaact agagatccct    6780
cagacccttt tagtcagtgt ggaaaatctc tagcagtagt agttcatgtc atcttattat    6840
tcagtattta aacttgcaa agaaatgaat atcagagagt gagaggaact tgtttattgc    6900
agcttataat ggttacaaat aaagcaatag catcacaaat ttcacaaata aagcattttt    6960
```

```
ttcactgcat tctagttgtg gtttgtccaa actcatcaat gtatcttatc atgtctggct    7020
ctagctatcc cgcccctaac tccgcccagt tccgcccatt ctccgcccca tggctgacta    7080
atttttttta tttatgcaga ggccgaggcc gcctcggcct ctgagctatt ccagaagtag    7140
tgaggaggct tttttggagg cctaggcttt tgcgtcgaga cgtacccaat tcgccctata    7200
gtgagtcgta ttacgcgcgc tcactggccg tcgttttaca acgtcgtgac tgggaaaacc    7260
ctggcgttac ccaacttaat cgccttgcag cacatccccc tttcgccagc tggcgtaata    7320
gcgaagaggc ccgcaccgat cgcccttccc aacagttgcg cagcctgaat ggcgaatggc    7380
gcgacgcgc ctgtagcggc gcattaagcg cggcgggtgt ggtggttacg cgcagcgtga     7440
ccgctacact tgccagcgcc ctagcgcccg ctcctttcgc tttcttccct cctttctcg     7500
ccacgttcgc cggctttccc cgtcaagctc taaatcgggg gctcccttta gggttccgat    7560
ttagtgcttt acggcacctc gaccccaaaa aacttgatta gggtgatggt tcacgtagtg    7620
ggccatcgcc ctgatagacg gttttttcgcc ctttgacgtt ggagtccacg ttctttaata   7680
gtggactctt gttccaaact ggaacaacac tcaaccctat ctcggtctat tcttttgatt   7740
tataaggat tttgccgatt tcggcctatt ggttaaaaaa tgagctgatt taacaaaaat    7800
ttaacgcgaa ttttaacaaa atattaacgt ttacaatttc ccaggtggca cttttcgggg    7860
aaatgtgcgc ggaacccta tttgtttatt tttctaaata cattcaaata tgtatccgct    7920
catgagacaa taaccctgat aaatgcttca ataatattga aaaggaaga gtatgagtat     7980
tcaacatttc cgtgtcgccc ttattcccttt ttttgcggca ttttgccttc ctgtttttgc   8040
tcacccagaa acgctggtga agtaaaaga tgctgaagat cagttgggtg cacgagtggg    8100
ttacatcgaa ctggatctca acagcggtaa gatccttgag agttttcgcc ccgaagaacg   8160
ttttccaatg atgagcactt ttaaagttct gctatgtggc gcggtattat cccgtattga   8220
cgccgggcaa gagcaactcg gtcgccgcat acactattct cagaatgact tggttgagta   8280
ctcaccagtc acagaaaagc atcttacgga tggcatgaca gtaagagaat tatgcagtgc   8340
tgccataacc atgagtgata acactgcggc caacttactt ctgacaacga tcggaggacc   8400
gaaggagcta accgcttttt tgcacaacat ggggatcat gtaactcgcc ttgatcgttg    8460
ggaaccggag ctgaatgaag ccataccaaa cgacgagcgt gacaccacga tgcctgtagc    8520
aatggcaaca acgttgcgca aactattaac tggcgaacta cttactctag cttcccggca    8580
acaattaata gactggatgg aggcggataa agttgcagga ccacttctgc gctcggccct    8640
tccggctggc tggtttattg ctgataaatc tggagccggt gagcgtgggt ctcgcggtat    8700
cattgcagca ctggggccag atggtaagcc ctcccgtatc gtagttatct acacgacggg    8760
gagtcaggca actatggatg aacgaaatag acagatcgct gagataggtg cctcactgat    8820
taagcattgg taactgtcag accaagttta ctcatatata ctttagattg atttaaaact    8880
tcatttttaa tttaaaagga tctaggtgaa gatccttttt gataatctca tgaccaaaat    8940
cccttaacgt gagttttcgt tccactgagc gtcagacccc gtagaaaaga tcaaaggatc    9000
ttcttgagat cctttttttc tgcgcgtaat ctgctgcttg caaacaaaaa aaccaccgct    9060
accagcggtg gtttgtttgc cggatcaaga gctaccaact cttttccga aggtaactgg     9120
cttcagcaga gcgcagatac caaatactgt ccttctagtg tagccgtagt taggccacca    9180
cttcaagaac tctgtagcac cgcctacata cctcgctctg ctaatcctgt taccagtggc    9240
tgctgccagt ggcgataagt cgtgtcttac cgggttggac tcaagacgat agttaccgga    9300
```

| | | |
|---|---|---|
| taaggcgcag cggtcgggct gaacgggggg ttcgtgcaca cagcccagct ggagcgaac | 9360 |
| gacctacacc gaactgagat acctacagcg tgagctatga gaaagcgcca cgcttcccga | 9420 |
| agggagaaag gcggacaggt atccggtaag cggcagggtc ggaacaggag agcgcacgag | 9480 |
| ggagcttcca gggggaaacg cctggtatct ttatagtcct gtcgggtttc gccacctctg | 9540 |
| acttgagcgt cgattttttgt gatgctcgtc agggggggcgg agcctatgga aaaacgccag | 9600 |
| caacgcggcc ttttttacggt tcctggcctt ttgctggcct tttgctcaca tgttctttcc | 9660 |
| tgcgttatcc cctgattctg tggataaccg tattaccgcc tttgagtgag ctgataccgc | 9720 |
| tcgccgcagc cgaacgaccg agcgcagcga gtcagtgagc gaggaagcgg aagagcgccc | 9780 |
| aatacgcaaa ccgcctctcc ccgcgcgttg gccgattcat taatgcagct ggcacgacag | 9840 |
| gtttcccgac tggaaagcgg gcagtgagcg caacgcaatt aatgtgagtt agctcactca | 9900 |
| ttaggcaccc caggctttac actttatgct tccggctcgt atgttgtgtg gaattgtgag | 9960 |
| cggataacaa tttcacacag gaaacagcta tgaccatgat tacgccaagc gcgcaattaa | 10020 |
| ccctcactaa agggaacaaa agctggagct gca | 10053 |

<210> SEQ ID NO 20
<211> LENGTH: 9405
<212> TYPE: DNA
<213> ORGANISM: Artificial Sequence
<220> FEATURE:
<223> OTHER INFORMATION: IL2Rg upstream of IL2Rb

<400> SEQUENCE: 20

| | | |
|---|---|---|
| agcttaatgt agtcttatgc aatactcttg tagtcttgca acatggtaac gatgagttag | 60 |
| caacatgcct tacaaggaga gaaaaagcac cgtgcatgcc gattggtgga agtaaggtgg | 120 |
| tacgatcgtg ccttattagg aaggcaacag acgggtctga catggattgg acgaaccact | 180 |
| gaattgccgc attgcagaga tattgtattt aagtgcctag ctcgatacaa taaacgggtc | 240 |
| tctctggtta gaccagatct gagcctggga gctctctggc taactaggga acccactgct | 300 |
| taagcctcaa taaagcttgc cttgagtgct tcaagtagtg tgtgcccgtc tgttgtgtga | 360 |
| ctctggtaac tagagatccc tcagaccctt ttagtcagtg tggaaaatct ctagcagtgg | 420 |
| cgcccgaaca gggacttgaa agcgaaaggg aaaccagagg agctctctcg acgcaggact | 480 |
| cggcttgctg aagcgcgcac ggcaagaggc gaggggcggc gactggtgag tacgccaaaa | 540 |
| attttgacta gcggaggcta aaggagaga gatgggtgcg agagcgtcag tattaagcgg | 600 |
| gggagaatta gatcgcgatg ggaaaaaatt cggttaaggc caggggggaaa gaaaaaatat | 660 |
| aaattaaaac atatagtatg ggcaagcagg gagctagaac gattcgcagt taatcctggc | 720 |
| ctgttagaaa catcagaagg ctgtagacaa atactgggac agctacaacc atcccttcag | 780 |
| acaggatcag aagaacttag atcattatat aatacagtag caaccctcta ttgtgtgcat | 840 |
| caaaggatag agataaaaga caccaaggaa gctttagaca agatagagga agagcaaaac | 900 |
| aaaagtaaga ccaccgcaca gcaagcggcc gctgatcttc agacctggag gaggagatat | 960 |
| gagggacaat tggagaagtg aattatataa atataaagta gtaaaaattg aaccattagg | 1020 |
| agtagcaccc accaaggcaa agagaagagt ggtgcagaga gaaaaaagag cagtgggaat | 1080 |
| aggagctttg ttccttgggt tcttgggagc agcaggaagc actatgggcg cagcctcaat | 1140 |
| gacgctgacg gtacaggcca gacaattatt gtctggtata gtgcagcagc agaacaattt | 1200 |
| gctgagggct attgaggcgc aacagcatct gttgcaactc acagtctggg gcatcaagca | 1260 |
| gctccaggca agaatcctgg ctgtggaaag atacctaaag gatcaacagc tcctggggat | 1320 |

```
ttggggttgc tctggaaaac tcatttgcac cactgctgtg ccttggaatg ctagttggag    1380
taataaatct ctggaacaga tttggaatca cacgacctgg atggagtggg acagagaaat    1440
taacaattac acaagcttaa tacactcctt aattgaagaa tcgcaaaacc agcaagaaaa    1500
gaatgaacaa gaattattgg aattagataa atgggcaagt tgtggaatt ggtttaacat     1560 aacaaattgg ctgtggtata taaaattatt cataatgata gtaggaggct tggtaggttt    1620
aagaatagtt tttgctgtac tttctatagt gaatagagtt aggcagggat attcaccatt    1680
atcgtttcag acccacctcc caaccccgag gggacccgac aggcccgaag aatagaaga     1740 agaaggtgga gagagagaca gagacagatc cattcgatta gtgaacggat ctcgacggta    1800
tcggttaact tttaaaagaa aagggggat tgggggtac agtgcagggg aagaatagt       1860 agacataata gcaacagaca tacaaactaa agaattacaa aaacaaatta caaaaattca    1920
aaattttatc gatcacgaga ctagcctcga gaagcttgat atcgaattcc cacggggttg    1980
gacgcgtagg aacagagaaa caggagaata tgggccaaac aggatatctg tggtaagcag    2040
ttcctgcccc ggctcagggc caagaacagt tggaacagca gaatatgggc caaacaggat    2100
atctgtggta agcagttcct gccccggctc agggccaaga acagatggtc ccagatgcg     2160 gtcccgccct cagcagtttc tagagaacca tcagatgttt ccagggtgcc caaggacct     2220 gaaatgaccc tgtgccttat ttgaactaac caatcagttc gcttctcgct tctgttcgcg    2280
cgcttctgct ccccgagctc tatataagca gagctcgttt agtgaaccgt cagatcgcta    2340
gcaccggtgc cgccaccatg cctctgggcc tgctgtggct gggcctggcc ctgctgggcg    2400
ccctgcacgc ccaggccggc gtgcaggtgg agacaatctc cccaggcgac ggacgcacat    2460
tccctaagcg gggccagacc tgcgtggtgc actatacagg catgctggag gatggcaaga    2520
agtttgacag ctcccgggat agaaacaagc cattcaagtt tatgctgggc aagcaggaag    2580
tgatcagagg ctgggaggag ggcgtggccc agatgtctgt gggccagagg ccaagctga    2640 ccatcagccc agactacgcc tatggagcaa caggccaccc aggaatcatc ccacctcacg    2700
ccaccctggt gttcgatgtg gagctgctga agctgggcga gggatccaac acatcaaaag    2760 agaaccccctt tctgttcgca ttggaggccg tagtcatatc tgttggatcc atgggactta    2820
ttatctccct gttgtgtgtg tacttctggc tggaacggac tatgcccagg atccccacgc    2880
tcaagaatct ggaagatctc gtcacagaat accatgtaa tttcagcgcc tggagcggag    2940
tctctaaggg tctggccgaa tccctccaac ccgattattc tgaacggttg tgcctcgtat    3000
ccgaaatacc accaaaaggc ggggctctgg gtgagggccc aggggcgagt ccgtgcaatc    3060
aacacagccc gtattgggcc cctccttgtt atacgttgaa gcccgaaaact ggaagcggag    3120 ctactaactt cagcctgctg aagcaggctg gagacgtgga ggagaaccct ggacctatgg    3180
cactgcccgt gaccgccctg ctgctgcctc tggccctgct gctgcacgca gcccggccta    3240
tcctgtggca cgagatgtgg cacgagggcc tggaggaggc cagcaggctg tattttggcg    3300
agcgcaacgt gaagggcatg ttcgaggtgc tggagcctct gcacgccatg atggagagag    3360
gcccacagac cctgaaggag acatcctta accaggccta tgacgggac ctgatggagg     3420 cacaggagtg gtgcagaaag tacatgaagt ctggcaatgt gaaggacctg ctgcaggcct    3480
gggatctgta ctatcacgtg tttcggagaa tctccaaggg caaagacacg attccgtggc    3540
ttgggcatct gctcgttggg ctgagtggtg cgtttggttt catcatcttg gtctatctct    3600
tgatcaattg cagaaataca ggcccttggc tgaaaaaagt gctcaagtgt aatacccccg    3660
```

-continued

```
acccaagcaa gttcttctcc cagctttctt cagagcatgg aggcgatgtg cagaaatggc    3720
tctcttcacc ttttccctcc tcaagcttct ccccggagg gctggcgccc gagatttcac    3780
ctcttgaggt acttgaacga gacaaggtta cccaacttct ccttcaacag gataaggtac    3840
ccgaacctgc gagccttagc tccaaccact ctcttacgag ctgcttcacc aatcagggat    3900
acttcttttt ccaccttccc gatgcgctgg aaatcgaagc ttgtcaagtt tactttacct    3960
atgatccata tagcgaggaa gatcccgacg aaggagtcgc cggtgcgccc acgggttcct    4020
caccccaacc tctccagcct ctctcaggag aagatgatgc ttattgcact tttcccagta    4080
gagacgatct cctcctcttt tctccatctc ttttggggg accttccccc ccttctacgg    4140
cacctggcgg gtctggtgct ggcgaggagc ggatgccgcc gtccctccag gagcgagtac    4200
cacgagattg ggatccccag ccacttggac cccccacccc cggcgtacct gaccttgtcg    4260
attttcaacc tcccctgaa ttggtgctgc gagaggctgg ggaggaagtt ccggacgctg    4320
ggccgaggga gggcgtgtcc tttccatgga gtaggcctcc aggtcaaggc gagtttaggg    4380
ctctcaacgc gcggctgccg ttgaatacag acgcttatct ctcactgcag gaactgcaag    4440
gtcaggaccc aacacatctt gtaggatctg gtgctactaa ttttctctt ttgaagcaag    4500 ctggagatgt tgaagagaac cctggtccag tgagcaaggg cgaggagctg ttcaccgggg    4560
tggtgcccat cctggtcgag ctggacggcg acgtaaacgg ccacaagttc agcgtgtccg    4620
gcgagggcga gggcgatgcc acctacggca agctgaccct gaagttcatc tgcaccaccg    4680
gcaagctgcc cgtgccctgg cccaccctcg tgaccaccct gacctacggc gtgcagtgct    4740
tcagccgcta ccccgaccac atgaagcagc acgacttctt caagtccgcc atgcccgaag    4800
gctacgtcca ggagcgcacc atcttcttca aggacgacgg caactacaag acccgcgccg    4860
aggtgaagtt cgagggcgac accctggtga accgcatcga gctgaagggc atcgacttca    4920
aggaggacgg caacatcctg ggcacaagc tggagtacaa ctacaacagc cacaacgtct    4980
atatcatggc cgacaagcag aagaacggca tcaaggtgaa cttcaagatc cgccacaaca    5040
tcgaggacgg cagcgtgcag ctcgccgacc actaccagca gaacacccc atcggcgacg    5100 gccccgtgct gctgcccgac aaccactacc tgagcaccca gtccgccctg agcaaagacc    5160
ccaacgagaa gcgcgatcac atggtcctgc tggagttcgt gaccgccgcc gggatcactc    5220
tcggcatgga cgagctgtac aagtaaacta gtgtcgacaa tcaacctctg gattacaaaa    5280
tttgtgaaag attgactggt attcttaact atgttgctcc ttttacgcta tgtggatacg    5340
ctgctttaat gcctttgtat catgctattg cttcccgtat ggctttcatt ttctcctcct    5400
tgtataaatc ctggttgctg tctctttatg aggagttgtg gcccgttgtc aggcaacgtg    5460
gcgtggtgtg cactgtgttt gctgacgcaa ccccactgg ttgggcatt gccaccacct    5520 gtcagctcct ttccgggact ttcgctttcc ccctccctat tgccacggcg gaactcatcg    5580
ccgcctgcct tgcccgctgc tggacagggg ctcggctgtt gggcactgac aattccgtgg    5640
tgttgtcggg gaagctgacg tccttccat ggctgctcgc ctgtgttgcc acctggattc    5700
tgcgcgggac gtccttctgc tacgtccctt cggccctcaa tccagcggac cttccttccc    5760
gcggcctgct gccggtctg cggctcttc gcgtcttcg ccttcgccct cagacgagtc    5820
ggatctccct ttgggccgcc tccccgcctg gaattcgagc tcggtacctt taagaccaat    5880
gacttacaag gcagctgtag atcttagcca ctttttaaaa gaaaggggg gactggaagg    5940 gctaattcac tcccaacgaa gacaagatct gctttttgct tgtactgggt ctctctggtt    6000
agaccagatc tgagcctggg agctctctgg ctaactaggg aacccactgc ttaagcctca    6060
```

```
ataaagcttg ccttgagtgc ttcaagtagt gtgtgcccgt ctgttgtgtg actctggtaa    6120
ctagagatcc ctcagaccct tttagtcagt gtggaaaatc tctagcagta gtagttcatg    6180
tcatcttatt attcagtatt tataacttgc aaagaaatga atatcagaga gtgagaggaa    6240
cttgtttatt gcagcttata atggttacaa ataaagcaat agcatcacaa atttcacaaa    6300
taaagcattt ttttcactgc attctagttg tggtttgtcc aaactcatca atgtatctta    6360
tcatgtctgg ctctagctat cccgcccta actccgccca gttccgccca ttctccgccc    6420
catggctgac taatttttt tatttatgca gaggccgagg ccgcctcggc ctctgagcta    6480
ttccagaagt agtgaggagg cttttttgga ggcctaggct tttgcgtcga gacgtaccca    6540
attcgcccta tagtgagtcg tattacgcgc gctcactggc cgtcgtttta caacgtcgtg    6600
actgggaaaa ccctggcgtt acccaactta atcgccttgc agcacatccc ctttcgccca    6660
gctggcgtaa tagcgaagag gcccgcaccg atcgccttc ccaacagttg cgcagcctga    6720
atggcgaatg gcgcgacgcg ccctgtagcg gcgcattaag cgcggcgggt gtggtggtta    6780
cgcgcagcgt gaccgctaca cttgccagcg ccctagcgcc cgctcctttc gctttcttcc    6840
cttcctttct cgccacgttc gccggctttc cccgtcaagc tctaaatcgg gggctccctt    6900
tagggttccg atttagtgct ttacggcacc tcgacccca aaaacttgat tagggtgatg    6960
gttcacgtag tgggccatcg ccctgataga cggtttttcg ccctttgacg ttggagtcca    7020
cgttctttaa tagtggactc ttgttccaaa ctggaacaac actcaaccct atctcggtct    7080
attcttttga tttataaggg attttgccga tttcggccta ttggttaaaa aatgagctga    7140
tttaacaaaa atttaacgcg aattttaaca aaatattaac gtttacaatt cccaggtgg    7200
cacttttcgg ggaaatgtgc gcggaaccc tatttgttta ttttctaaa tacattcaaa    7260
tatgtatccg ctcatgagac aataaccctg ataaatgctt caataatatt gaaaaggaa    7320
gagtatgagt attcaacatt tccgtgtcgc ccttattccc ttttttgcgg cattttgcct    7380
tcctgttttt gctcacccag aaacgctggt gaaagtaaaa gatgctgaag atcagttggg    7440
tgcacgagtg ggttacatcg aactggatct caacagcggt aagatccttg agagttttcg    7500
ccccgaagaa cgttttccaa tgatgagcac ttttaaagtt ctgctatgtg gcgcggtatt    7560
atcccgtatt gacgccgggc aagagcaact cggtcgccgc atacactatt ctcagaatga    7620
cttggttgag tactcaccag tcacagaaaa gcatcttacg gatggcatga cagtaagaga    7680
attatgcagt gctgccataa ccatgagtga taacactgcg ccaacttac ttctgacaac    7740
gatcggagga ccgaaggagc taaccgcttt tttgcacaac atggggggatc atgtaactcg    7800
ccttgatcgt tgggaaccgg agctgaatga agccatacca aacgacgagc gtgacaccac    7860
gatgcctgta gcaatggcaa caacgttgcg caaactatta actggcgaac tacttactct    7920
agcttcccgg caacaattaa tagactggat ggaggcggat aaagttgcag gaccacttct    7980
gcgctcggcc cttccggctg gctggtttat tgctgataaa tctggagccg gtgagcgtgg    8040
gtctcgcggt atcattgcag cactggggcc agatggtaag ccctcccgta tcgtagttat    8100
ctacacgacg gggagtcagg caactatgga tgaacgaaat agacagatcg ctgagatagg    8160
tgcctcactg attaagcatt ggtaactgtc agaccaagtt tactcatata ctttagat    8220
tgatttaaaa cttcattttt aatttaaaag gatctaggtg aagatccttt ttgataatct    8280
catgaccaaa atcccttaac gtgagttttc gttccactga gcgtcagacc ccgtagaaaa    8340
gatcaaagga tcttcttgag atcctttttt tctgcgcgta atctgctgct tgcaaacaaa    8400
```

-continued

```
aaaaccaccg ctaccagcgg tggtttgttt gccggatcaa gagctaccaa ctcttttcc     8460 gaaggtaact ggcttcagca gagcgcagat accaaatact gtccttctag tgtagccgta    8520
gttaggccac cacttcaaga actctgtagc accgcctaca tacctcgctc tgctaatcct    8580
gttaccagtg gctgctgcca gtggcgataa gtcgtgtctt accgggttgg actcaagacg    8640
atagttaccg gataaggcgc agcggtcggg ctgaacgggg ggttcgtgca cacagcccag    8700
cttggagcga acgacctaca ccgaactgag atacctacag cgtgagctat gagaaagcgc    8760
cacgcttccc gaagggagaa aggcggacag gtatccggta agcggcaggg tcggaacagg    8820
agagcgcacg agggagcttc caggggggaaa cgcctggtat ctttatagtc ctgtcgggtt   8880
tcgccacctc tgacttgagc gtcgattttt gtgatgctcg tcagggggc ggagcctatg     8940 gaaaaacgcc agcaacgcgg ccttttacg gttcctggcc ttttgctggc cttttgctca    9000
catgttcttt cctgcgttat cccctgattc tgtggataac cgtattaccg cctttgagtg    9060
agctgatacc gctcgccgca gccgaacgac cgagcgcagc gagtcagtga gcgaggaagc    9120
ggaagagcgc ccaatacgca aaccgcctct ccccgcgcgt tggccgattc attaatgcag    9180
ctggcacgac aggtttcccg actggaaagc gggcagtgag cgcaacgcaa ttaatgtgag    9240
ttagctcact cattaggcac cccaggcttt cactttatg cttccggctc gtatgttgtg     9300
tggaattgtg agcggataac aatttcacac aggaaacagc tatgaccatg attacgccaa    9360
gcgcgcaatt aaccctcact aaagggaaca aagctggag ctgca                     9405
```